US011927551B2

(12) United States Patent
Couture et al.

(10) Patent No.: US 11,927,551 B2
(45) Date of Patent: Mar. 12, 2024

(54) SYSTEMS AND METHODS FOR USING BACKSCATTER IMAGING IN PRECISION AGRICULTURE

(71) Applicant: American Science and Engineering, Inc., Billerica, MA (US)

(72) Inventors: Aaron Couture, Reading, MA (US); Basak Oztan, Woburn, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 18/057,547

(22) Filed: Nov. 21, 2022

(65) Prior Publication Data
US 2023/0152249 A1 May 18, 2023

Related U.S. Application Data

(63) Continuation of application No. 17/125,717, filed on Dec. 17, 2020, now Pat. No. 11,536,672, which is a
(Continued)

(51) Int. Cl.
*G01N 23/00* (2006.01)
*G01N 23/083* (2018.01)
(Continued)

(52) U.S. Cl.
CPC ......... *G01N 23/203* (2013.01); *G01N 23/083* (2013.01); *G01N 33/0098* (2013.01)

(58) Field of Classification Search
CPC ....... G01N 2223/612; G01N 2223/613; G01N 23/203; G01N 33/0098
See application file for complete search history.

(56) References Cited

U.S. PATENT DOCUMENTS 3,904,923 A 9/1975 Schwartz
5,014,293 A 5/1991 Boyd
(Continued)

FOREIGN PATENT DOCUMENTS

CN 1556921 A 12/2004
CN 101287985 A 10/2008
(Continued)

OTHER PUBLICATIONS

"Mobile X-Ray Inspection Systems" Internet citation Feb. 12, 2007, pp. 1-2, XP007911046 Retrieved from the Internet: URL:http://web.archive.org/web/20070212000928/http://www.bombdetection.co-m/cat.sub.--details.php?catid=20> [retrieved on Jan. 6, 2010].
(Continued)

*Primary Examiner* — Dani Fox
(74) *Attorney, Agent, or Firm* — Novel IP

(57) ABSTRACT

Systems and methods for determining a mass of a crop by using at least one X-ray scanner is provided. The method includes obtaining at least two scan images of the crop, where a first of the at least two images is obtained along a first plane relative to the crop and a second of the at least two images is obtained along a second plane relative to the crop, and where the first plane is angularly displaced relative to the second plane, registering the first image and the second image, correcting the registered first and second images, and determining the mass of the crop from the corrected first and second images.

32 Claims, 33 Drawing Sheets

Related U.S. Application Data continuation-in-part of application No. 15/758,134, filed as application No. PCT/US2016/050545 on Sep. 7, 2016, now Pat. No. 10,955,367.

(60) Provisional application No. 62/337,971, filed on May 18, 2016, provisional application No. 62/215,456, filed on Sep. 8, 2015.

(51) Int. Cl.
*G01N 23/203* (2006.01)
*G01N 33/00* (2006.01)

(56) References Cited

U.S. PATENT DOCUMENTS

| | | | |
|---|---|---|---|
| 5,363,940 A | 11/1994 | Fahrion | |
| 5,692,029 A | 11/1997 | Husseiny | |
| 6,220,099 B1 | 4/2001 | Marti | |
| 6,292,533 B1 | 9/2001 | Swift | |
| 6,526,120 B1 | 2/2003 | Gray | |
| 6,614,872 B2 | 9/2003 | Bueno | |
| 6,636,581 B2 | 10/2003 | Sorenson | |
| 6,637,266 B1 | 10/2003 | Froom | |
| 6,763,635 B1 | 7/2004 | Lowman | |
| 6,888,640 B2 | 5/2005 | Spina | |
| 6,950,495 B2 | 9/2005 | Nelson | |
| 6,950,719 B2 | 9/2005 | Landers | |
| 6,973,158 B2 | 12/2005 | Besson | |
| 7,024,272 B2 | 4/2006 | Thomas | |
| 7,069,192 B1 | 6/2006 | Freitag | |
| 7,086,028 B1 | 8/2006 | Davis | |
| 7,092,106 B2 | 8/2006 | Cox | |
| 7,099,434 B2 | 8/2006 | Adams | |
| 7,103,434 B2 | 9/2006 | Chernyak | |
| RE39,396 E | 11/2006 | Swift | |
| 7,151,447 B1 | 12/2006 | Willms | |
| 7,203,276 B2 | 4/2007 | Arsenault | |
| 7,218,704 B1 | 5/2007 | Adams | |
| 7,224,772 B2 | 5/2007 | Jacobs | |
| 7,280,990 B2 | 10/2007 | Turner | |
| 7,305,063 B2 | 12/2007 | Heuscher | |
| 7,319,738 B2 | 1/2008 | Lasiuk | |
| 7,508,910 B2 | 3/2009 | Safai | |
| 7,623,626 B2 | 11/2009 | Safai | |
| 7,636,417 B2 | 12/2009 | Bjorkholm | |
| 7,649,976 B2 | 1/2010 | Georgeson | |
| 7,798,710 B1 | 9/2010 | Barnes | |
| 7,817,776 B2 | 10/2010 | Agrawal | |
| 7,860,213 B2 | 12/2010 | Akery | |
| 7,860,214 B1 | 12/2010 | Haff | |
| 7,991,113 B2 | 8/2011 | Carver | |
| 8,033,724 B2 | 10/2011 | Edwards | |
| 8,054,937 B2 | 11/2011 | Langeveld | |
| 8,148,693 B2 | 4/2012 | Ryge | |
| 8,173,970 B2 | 5/2012 | Inbar | |
| 8,389,942 B2 | 3/2013 | Morton | |
| 8,401,147 B2 | 3/2013 | Ryge | |
| 8,483,356 B2 | 7/2013 | Bendahan | |
| 8,532,823 B2 | 9/2013 | McElroy | |
| 8,923,481 B2 | 12/2014 | Schubert | |
| 11,536,672 B2* | 12/2022 | Couture | G01N 23/083 |
| 2001/0016803 A1 | 8/2001 | Sartiono | |
| 2003/0043964 A1 | 3/2003 | Sorenson | |
| 2004/0141584 A1 | 7/2004 | Bernardi | |
| 2004/0264626 A1 | 12/2004 | Besson | |
| 2005/0157842 A1 | 7/2005 | Agrawal | |
| 2006/0043310 A1 | 3/2006 | Arsenault | |
| 2006/0114477 A1 | 6/2006 | Cox | |
| 2006/0198498 A1 | 9/2006 | Birdwell | |
| 2007/0025505 A1 | 2/2007 | Bjorkholm | |
| 2007/0098142 A1 | 5/2007 | Rothschild | |
| 2007/0189454 A1 | 8/2007 | Georgeson | |
| 2007/0269006 A1 | 11/2007 | Safai | |
| 2007/0269007 A1 | 11/2007 | Akery | |
| 2008/0152081 A1 | 6/2008 | Cason | |
| 2008/0205594 A1 | 8/2008 | Bjorkholm | |
| 2008/0253524 A1 | 10/2008 | Boyden | |
| 2009/0110148 A1 | 4/2009 | Zhang | |
| 2009/0168964 A1 | 7/2009 | Safai | |
| 2009/0238336 A1 | 9/2009 | Akery | |
| 2009/0245462 A1 | 10/2009 | Agrawal | |
| 2009/0296887 A1 | 12/2009 | Boyden | |
| 2010/0034355 A1 | 2/2010 | Langeveld | |
| 2010/0061509 A1 | 3/2010 | D Ambrosio | |
| 2010/0295689 A1 | 11/2010 | Armistead | |
| 2010/0327174 A1 | 12/2010 | Edwards | |
| 2011/0064192 A1 | 3/2011 | Morton | |
| 2011/0075808 A1 | 3/2011 | Rothschild | |
| 2011/0103548 A1 | 5/2011 | Bendahan | |
| 2012/0314834 A1 | 12/2012 | Yao | |
| 2013/0299703 A1 | 11/2013 | Morton | |
| 2013/0325346 A1 | 12/2013 | McPeek | |
| 2014/0133629 A1 | 5/2014 | Morton | |
| 2015/0015697 A1* | 1/2015 | Redden | G06V 10/751 382/110 |
| 2016/0223507 A1 | 8/2016 | Li | |
| 2020/0049635 A1 | 2/2020 | Couture | |

FOREIGN PATENT DOCUMENTS

| | | |
|---|---|---|
| CN | 101501477 A | 8/2009 |
| CN | 101592623 A | 12/2009 |
| CN | 102435620 A | 5/2012 |
| CN | 102549413 A | 7/2012 |
| CN | 102596039 A | 7/2012 |
| CN | 103597343 A | 2/2014 |
| EP | 1701153 A1 | 9/2006 |
| EP | 2377467 A1 | 10/2011 |
| GB | 2255634 A | 11/1992 |
| JP | 6243545 A | 9/2017 |
| WO | 1998055851 A1 | 12/1998 |
| WO | 0218958 A2 | 3/2002 |
| WO | 2004092768 A2 | 10/2004 |
| WO | 2009150416 A2 | 12/2009 |
| WO | 2011059838 A1 | 5/2011 |

OTHER PUBLICATIONS

Molchanov P A et al: 'Nanosecond gated optical sensors for ocean optic applications' Sensors Applications Symposium, 2006. Proceedings of The 2006 IEEE Houston, Texas, USA Feb. 7-9, 2006, Piscataway, NJ, USA, IEEE, Feb. 7, 2006 (Feb. 7, 2006), pp. 147-150, XP010917671 ISBN: 978-0-7803-9580-0.

International Search Report and Written Opinion of the International Searching Authority for PCT/US16/50545, dated Dec. 23, 2016.

Cruvinel, Paulo E. and Balogun, Fatai A. "Compton scattering tomography for agricultural measurements" Eng. Agric. [online]. 2006, vol. 26, n.1 [cited Sep. 3, 2018], pp. 151-160.

Cruvinel P E et al: "Minitomography scanner for agriculture based on dual-energy Compton scattering", Computer Graphics and Image Processing, 2000. Proceedings XIII Brazili an Symposium on Gramado, Brazil Oct. 17-20, 2000, Los Alamitos, CA USA, IEEE Comput. Soc. US, Oct. 17, 2000, pp. 193-199, XP010521945, DOI: 10.1109/SIGBRA.2000.883913, ISBN: 978-0-7695-0878-8.

John Buglione: "Use of Compton Backscatter X-ray Imaing in Agriculture", May 2016, XP055580377, Retrieved from the Internet: URL:http://www.jakebuglione.com/thesis.pdf [retrieved on Apr. 11, 2019].

"Application of Multi-spectrum Reflectance Vision Technique for Harvesting Robot", Lin, Weimin et al., "Agricultural Equipment and Technology", vol. 30, No. 6, pp. 15-18, 2004.

International Search Report for PCT/US20/65704, dated Apr. 22, 2021.

Written Opinion of the International Searching Authority for PCT/US20/65704, dated Apr. 22, 2021.

* cited by examiner

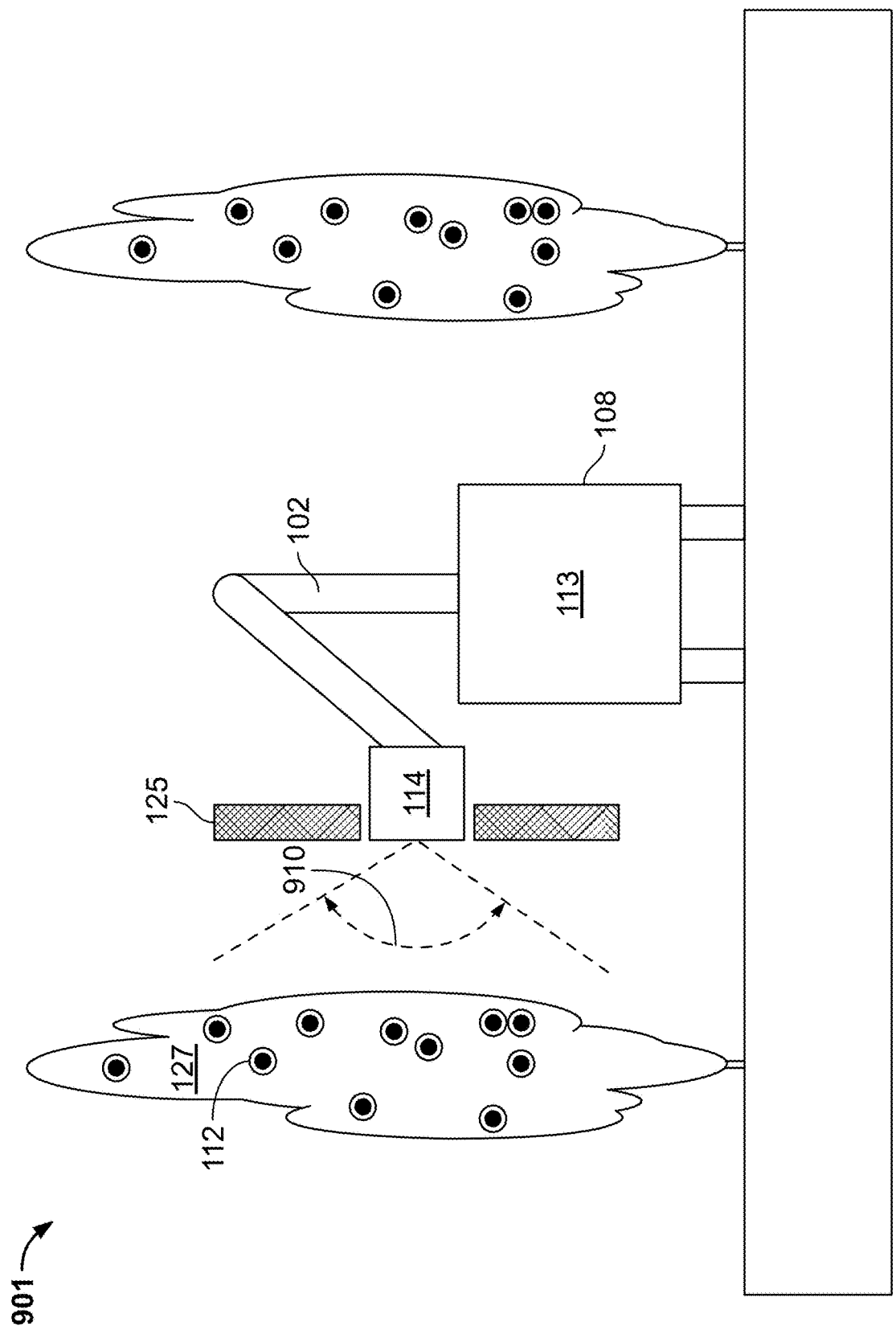

| Crop | Annual/ Perennial | Plant Support | Crop Type | Height (ft) | Width (ft) | Imaging Orientation | Imaging Stand off (ft) | Power (w) | Energy (keV) |
|---|---|---|---|---|---|---|---|---|---|
| Apples - managed | Perennial | Wire trellis | Isolated | 10 | 6 | Horizontal | 6 | 1000 | 140 |
| Apples - unmanaged | Perennial | Tree | Isolated | 15 | 15 | Horizontal | 9 | 2000 | 140 |
| Grapes | Perennial | Wire trellis | Cluster | 6 | 4 | Horizontal | | | |
| Strawberries | Perennial | Ground | Isolated | 0.5 | 1.5 | Top down | 2 | 120 | 70-120 |
| Squash/ melons | Perennial | Ground | Isolated | 1.5 | 2 | Top down | 3 | 120 | 70-120 |
| Tomatoes | Annual | Bush | Isolated | 3-4 | 2-3 | Horizontal or top down | 3-4 | 120-300 | 70-120 |
| Nuts | Annual | Tree | Cluster | 15 | 6 | Horizontal | 9 | 2000 | 140 |
| Cotton | Perennial/ Annual depends on breed | Bush/shrub | Isolated | <9, 2-4 ft typical | 3 | Horizontal or top down | 6 Horizontal or top down | 120-300 | 70-120 |

FIG. 11

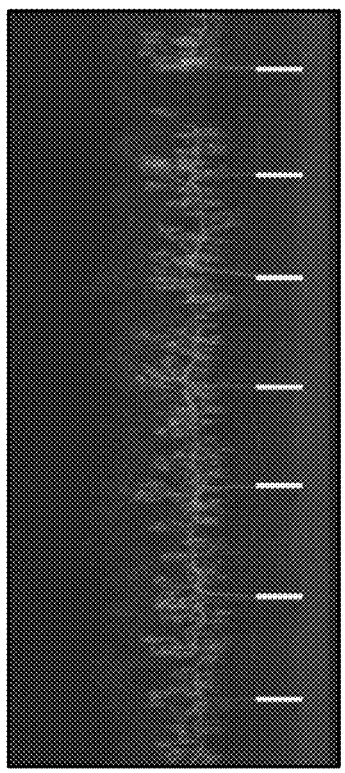
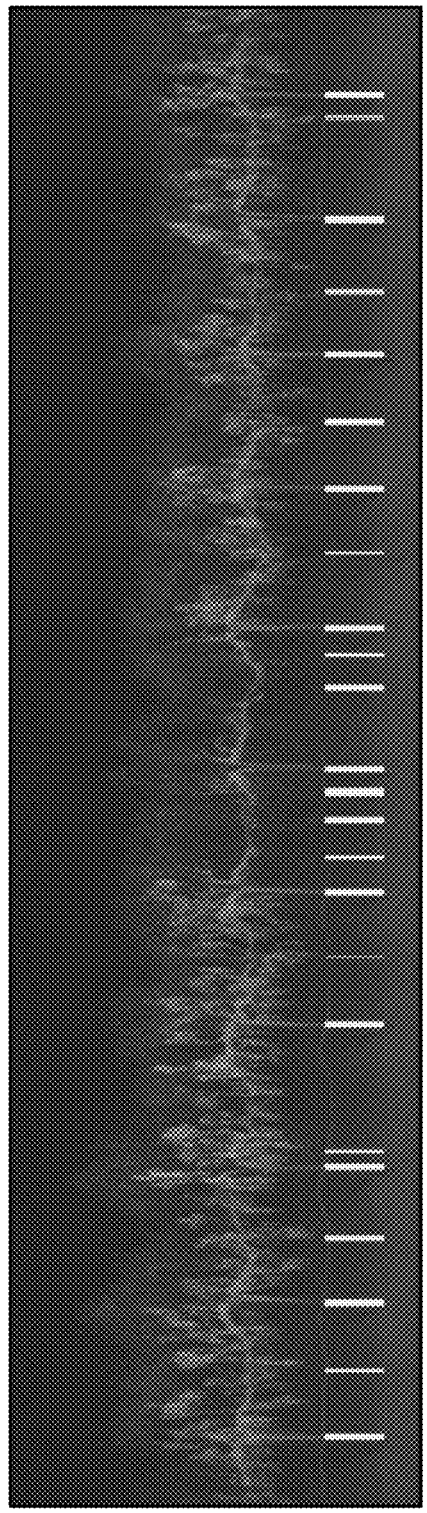
FIG. 15A
FIG. 15B

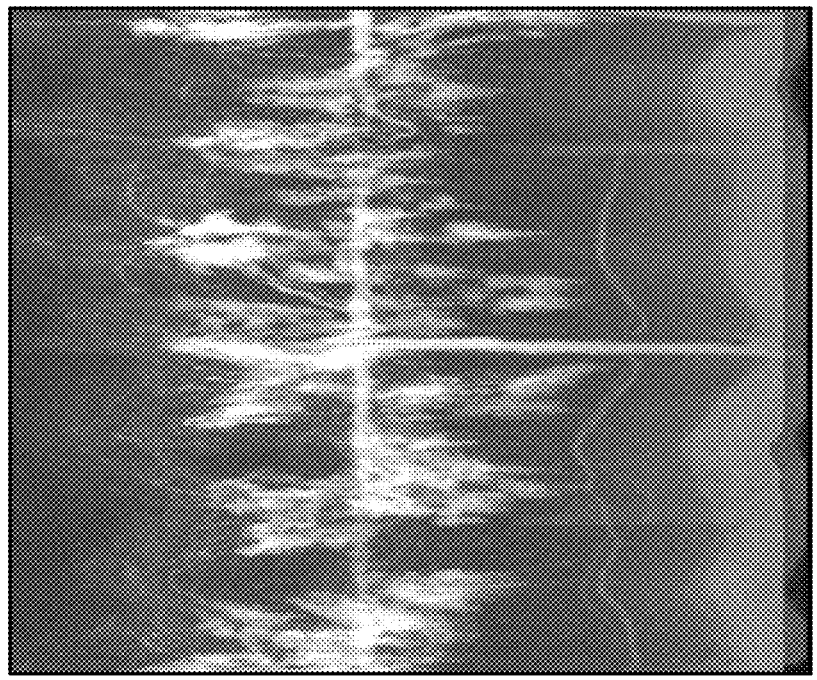
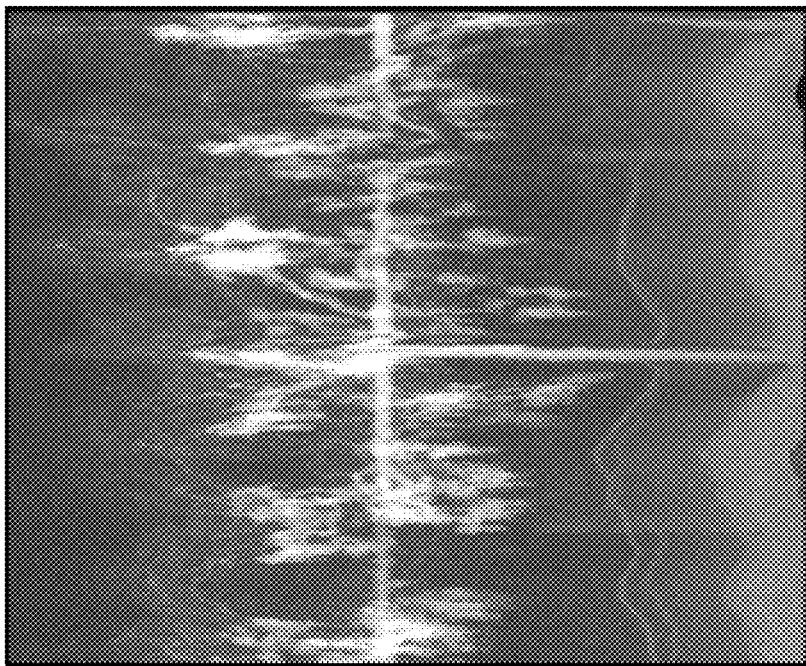
FIG. 16C

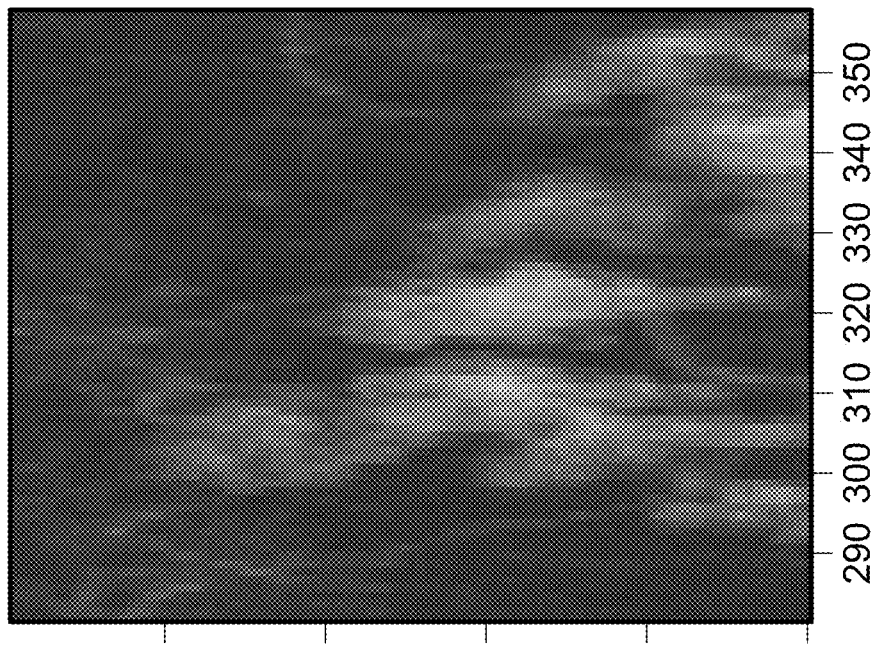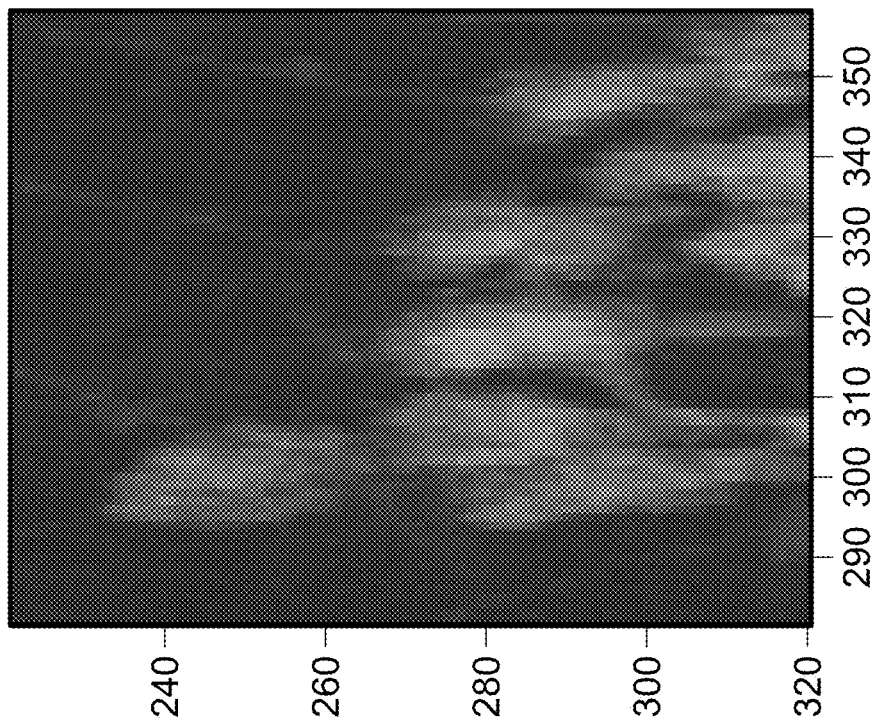
FIG. 16D

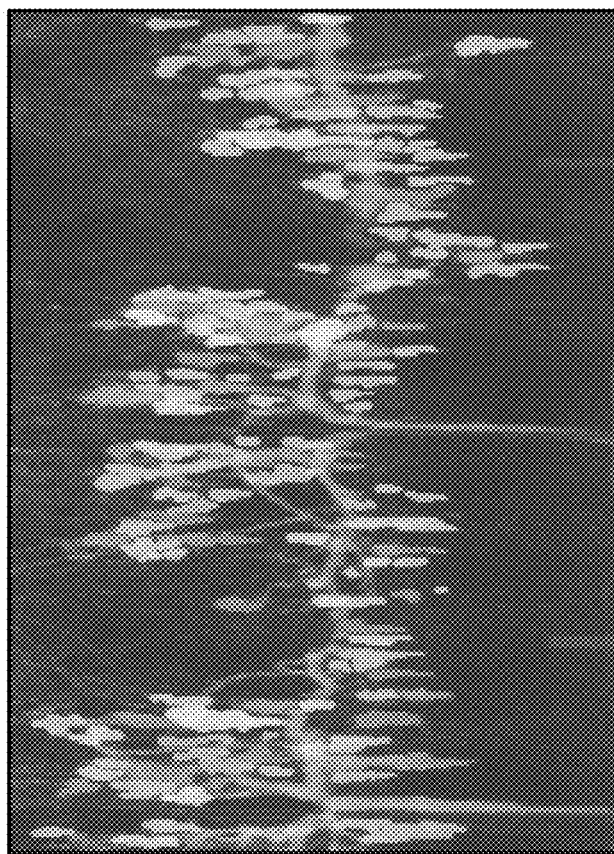
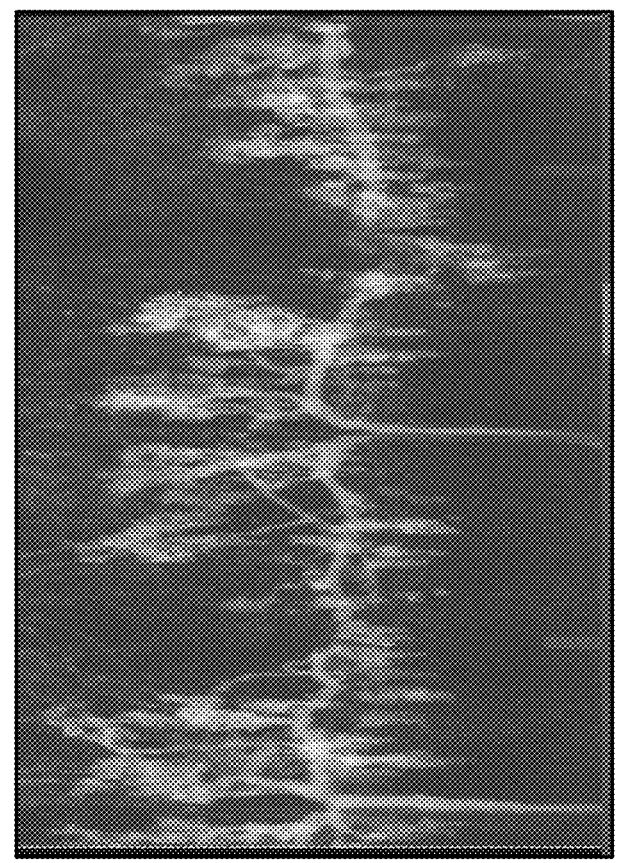
FIG. 17A

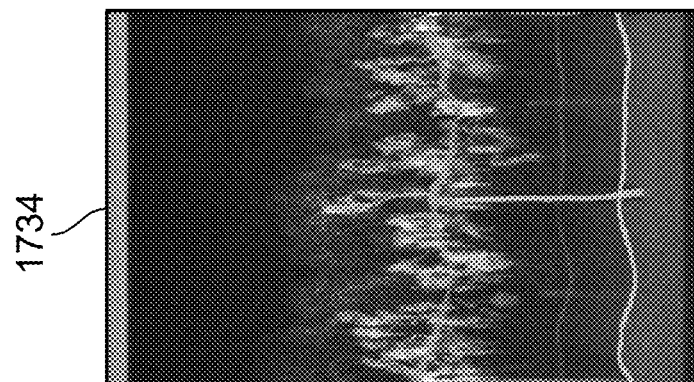
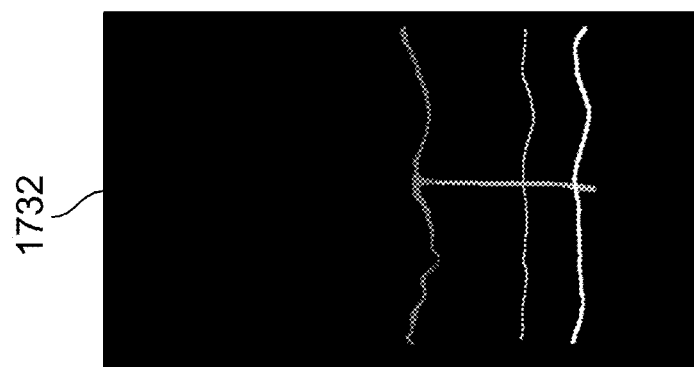
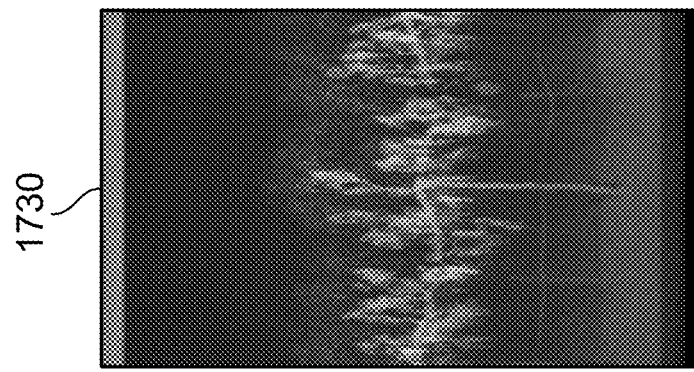
FIG. 17B

| Date | Stage | Avg Weight (lbs) | Correlation with harvest |
|------|-------|------------------|--------------------------|
| 5/24 | Fruit set | 30.0 | 0.64 |
| 6/7 | Fruit set +2 Wk | 52.0 | 0.52 |
| 7/22 | Verasion | 82 | 0.63 |
| 10/11 | Harvest | 97 | 0.80 |

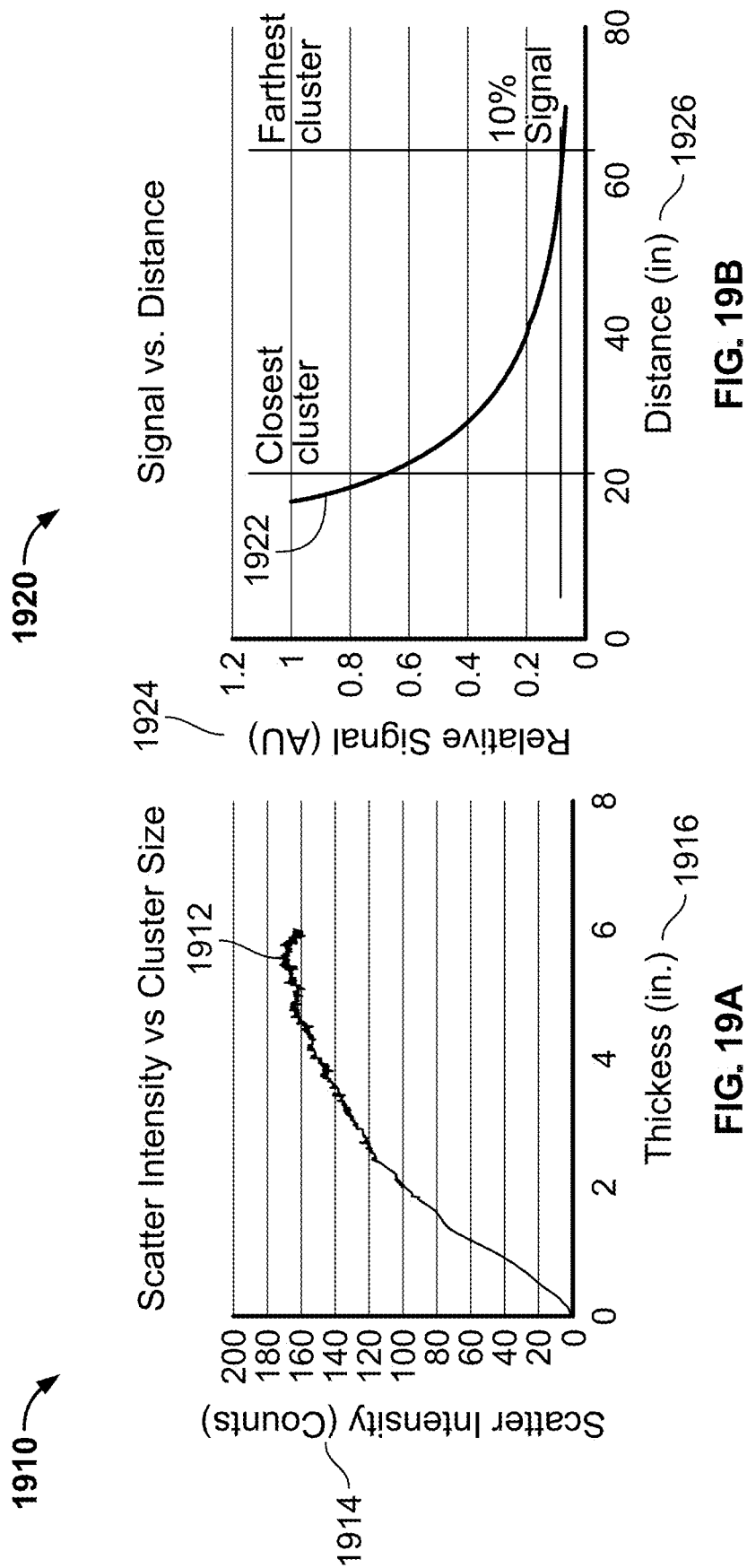

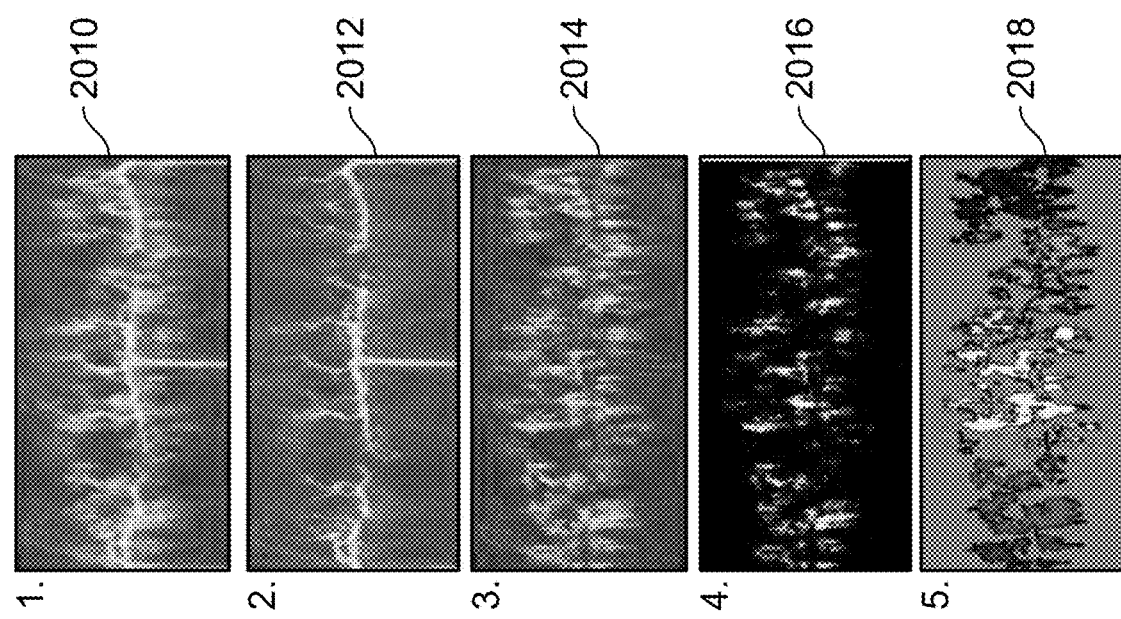

SYSTEMS AND METHODS FOR USING BACKSCATTER IMAGING IN PRECISION AGRICULTURE

CROSS-REFERENCE

The present application is a continuation application of U.S. patent application Ser. No. 17/125,717, entitled "Systems and Methods for Using Backscatter Imaging in Precision Agriculture" and filed on Dec. 17, 2020, which is a continuation-in-part application of U.S. patent application Ser. No. 15/758,134, entitled "Backscatter Imaging for Precision Agriculture", filed on Mar. 7, 2018, and issued as U.S. Pat. No. 10,955,367 on Mar. 23, 2021, which is a 371 National Stage application of PCT/US2016/050545, of the same title and filed on Sep. 7, 2016, which, in turn, relies on, for priority, U.S. Patent Provisional Application No. 62/337,971, filed on May 18, 2016, and U.S. Patent Provisional Application No. 62/215,456, filed on Sep. 8, 2015.

In addition, the present application relates to U.S. patent application Ser. No. 16/656,965, entitled "Backscatter Imaging for Precision Agriculture", filed on Oct. 18, 2019, and issued as U.S. Pat. No. 10,712,293 on Jul. 14, 2020, which is a continuation application of U.S. patent application Ser. No. 15/758,134, of the same title and filed on Mar. 7, 2018, which is a 371 National Stage application of PCT/US2016/050545, of the same title and filed on Sep. 7, 2016, which relies on, for priority, U.S. Patent Provisional Application No. 62/337,971, filed on May 18, 2016, and U.S. Patent Provisional Application No. 62/215,456, filed on Sep. 8, 2015.

The contents of all of the above referenced applications are incorporated herein by reference, including the attachments thereto.

FIELD

The present invention relates to devices and methods for deriving agriculturally significant crop data from X-ray backscatter imaging and characterization.

BACKGROUND

For the last 10,000 years, crops have been cultivated on the basis of unsystematically collected data. Now that humankind has harnessed electromagnetic radiation that penetrates vegetation, more systematic assessment of the condition of crops in vivo should have become possible, however hurdles described below have precluded their application to date.

Precision agriculture describes a management technique based on crop and soil data measured in the field as a function of position and time. The correlation of data with its position in the field over time is used to make farm management decisions that can maximize overall returns. Data collection can include information about four main areas: farm environment, soil, plants or the final crops. Much value, in terms of crop yield and quality would be attainable if there were only some way to provide specific and accurate data for a number of these key areas across a wide variety of different crops, especially in the area of specialty crops. Specialty crops include high value fruits, vegetables and nuts which are used for food or medicine which are marketed directly to customers and thus require exceptionally high esthetic quality. For these crops, a high value is placed both on accurate yield prediction as well as plant health. Early and accurate measurement of crop yields enables staging of equipment and resources for harvest, packaging and storage as well as the capability to accurately price crops. For tree and vine based specialty crops, the maintenance and health of the plant year over year is also critical. Collection of yield data and plant health year after year would enable predictive tools to be used for fertilization and watering as well as harvest planning.

Crop yield estimation is an important task in the management of a variety of agricultural crops, including fruit orchards such as apples. Fruit crops, such as apples, citrus fruits, grapes, and others, are composed of the plant, which is starch rich and relatively low density (leaves, branches, and stems), as well as the fruit, which is compact and water saturated. Current techniques for estimation rely on statistical sampling using humans to provide yield estimation, which is time-consuming, labor intensive, and inaccurate.

According to Wang, et al., "Automated Crop Yield Estimation for Apple Orchards," 13th International Symposium on Experimental Robotics (ISER 2012), which is incorporated herein by reference, Accurate yield prediction helps growers improve fruit quality and reduce operating costs by making better decisions on the intensity of fruit thinning and size of the harvest labor force. It benefits the packing industry as well, because managers can use estimation results to optimize packing and storing capacity. Typical yield estimation is performed based on historical data, weather conditions, and workers manually counting yield of fruit, such as apples, in multiple sampling locations. This process is time-consuming and labor intensive, and the limited sample size is usually not enough to reflect the yield distribution across the orchard, especially in those with high spatial variability. Therefore, the current yield estimation practice is inaccurate and inefficient, and improving current practices would be a significant result to the industry. Ibid, p. 1.

While X-ray scattering had been observed for some time, the mechanism whereby X-ray quanta are scattered by electrons was first described by Compton, "On the Mechanism of X-Ray Scattering," *Proc. Nat. Acad. Sci.*, vol. 11, pp. 303-06 (1925), incorporated herein by reference, and has since been referred to as "Compton scattering." Prior suggestions to use X-ray backscatter in characterizing plant material have been limited to applications in which agricultural produce has already been picked and is being handled under controlled conditions. These include actual handling of food during processing, as discussed by Cruvinel et al., "Compton Scatter Tomography for Agricultural Measurements," *Eng. Aric. Jaboticabal*, vol. 26, pp. 151-60 (2006), and U.S. Pat. No. 7,734,012 (to Boyden et al.), both of which are incorporated herein by reference.

Fruit growers desire an automated system for conducting crop yield estimates. Current techniques focus on visual imaging systems. Estimation based on the visual environment is challenging due to variable illumination, occlusion due to foliage, and multiple counts. Occlusion by foliage may result in multiple counts, based on difficulty viewing the entire crop. Visual imaging processing may advantageously also be computationally intensive.

Application of X-ray backscatter to crops that have not been harvested and that are alive in the field offers particular benefits, but would require specialized techniques not hitherto known in the art. Those specialized techniques and benefits are described in detail below, in accordance with the present invention.

SUMMARY

The following embodiments and aspects thereof are described and illustrated in conjunction with systems, tools and methods, which are meant to be exemplary and illustrative, and not limiting in scope. The present application discloses numerous embodiments.

In some embodiments, the present specification discloses a method for estimating weight of crop, wherein the crop comprises at least one row of plants and wherein the at least one row of plants comprises at least one vine and/or branch bearing fruit, the method comprising: irradiating a predefined area of the crop with X-rays from at least two sides; obtaining scan images of the at least one row of plants; performing contrast enhancement and de-noising with respect to each of the collected scan images; performing a global registration of all the contrast enhanced, de-noised images; obtaining split images representing individual vines and/or branches by separating and discarding edges of the at least one vine and/or branch bearing fruit in the at least one row of plants; performing a local registration of the obtained split images; performing a cluster segmentation function on each of the split images; processing the resultant segmented images using distance calibration; and, estimating a weight of the crop by using the distance calibrated images.

The present specification discloses a method for estimating weight of crop, wherein the crop comprises at least one row of plants and wherein the at least one row of plants comprises at least one vine and/or branch bearing fruit, the method comprising: irradiating a predefined area of the crop with X-rays from at least two sides; obtaining scan images of the at least one row of plants; performing contrast enhancement and de-noising with respect to each of the collected scan images; performing a global registration of all the contrast enhanced, de-noised images; obtaining split images representing individual vines and/or branches by separating vines and/or branches from said images; performing a local registration of the obtained split images; performing a cluster segmentation function on each of the split images; processing the resultant segmented images using distance calibration; and, estimating a weight of the crop by using the distance calibrated images.

Optionally, the step of collecting scan image data of at least one row of plants comprises flipping scan images, generated by irradiating the predefined area of the crop with X-rays, in a same predefined direction.

Optionally, separating vines and/or branches from said images comprises cutting out separate vines and/or branches from said images by discarding edges of at least one vine and/or branch bearing fruit in the at least one row of plants.

Optionally, performing local registration comprises obtaining alignment between pairs of images showing different views of a same vine and/or branch.

Optionally, the method further comprises predicting a yield of the crop using the distance calibrated images.

Optionally, obtaining scan images of at least one row of plants comprises: extracting image data from a raw data file; creating a schematic map of each predefined area; plotting a movement of a vehicle carrying a scanning apparatus being used for irradiating the crop with X-rays on the schematic map; and determining a GPS coordinate of a point on the schematic map by correlating at least one timestamp of one or more GPS coordinates with at least one timestamp of when points on the schematic map were captured. Optionally, the method further comprises locating rows of plants along with corresponding direction based on a direction of movement of the vehicle and flipping the located rows of plants in a predefined direction for obtaining a consistent sequence of plants in a row in each obtained scan image. Optionally, the method further comprises normalizing each obtained scan image by using a predefined normalization bar. Optionally, the method further comprises scanning GPS coordinates of each predefined area for obtaining distance between rows of plants in said areas.

Optionally, the method further comprises identifying and annotating the segmented images.

Optionally, the method further comprises determining a cluster processing technique for processing each of the split images.

Optionally, the method further comprises processing the split images by using a coarse cluster segmentation method.

Optionally, the cluster segmentation function is either a classical cluster segmentation function or a deep learning cluster segmentation function.

Optionally, an estimated weight of fruit hanging from plants is determined by determining a change in an X-ray signal backscattered by the fruit over a predefined period of time. Optionally, the fruit comprises one of: grapes, berries, citrus fruits, apples, melons, and tomatoes. Optionally, the X-ray signal backscattered from the fruit is proportional to a mass of the fruit and a distance of the fruit from a scanning system generating the X-rays for irradiating the fruit. Optionally, the X-ray signal backscattered from the fruit is proportional to the square of the distance of the fruit from the scanning system. Optionally, a total mass of the fruit is determined by integrating a signal intensity of the X-ray signal backscattered from the fruit across the crop. Optionally, the method further comprises performing dual view data acquisition by scanning the fruit using two X-ray scanners simultaneously. Optionally, the method further comprises performing dual view data acquisition by scanning the fruit using a single X-ray scanner with multiple acquisitions. Optionally, X-ray scanners are positioned outside of a fruiting region of a field, the scanners being positioned on opposite sides of a row of fruit plants. Optionally, the method further comprises collecting images of the fruit and analyzing said images by using a distance normalization process at a pixel or feature level.

The present specification also discloses a method for determining a mass of a crop by using at least one X-ray scanner, the method comprising: obtaining at least two scan images of the crop, wherein a first of the at least two scan images is obtained along a first plane relative to the crop and a second of the at least two scan images is obtained along a second plane relative to the crop, and wherein the first plane is angularly displaced relative to the second plane; registering the first scan image and the second scan image; correcting the registered first and second scan images; and determining the mass of the crop from the corrected first and second scan images.

Optionally, the first plane is angularly displaced relative to the second plane by an angle ranging between 90 degrees and 270 degrees.

Optionally, the first plane and the second plane are parallel to each other.

Optionally, registering the first scan image and the second scan image comprises matching the first scan image and the second scan image by flipping and translating at least one of the first scan image and the second scan image relative to the other.

Optionally, obtaining at least two scan images of the crop comprises scanning the crop using two X-ray scanners simultaneously.

Optionally, obtaining at least two scan images of the crop comprises scanning the crop using a single X-ray scanner and executing multiple scans.

Optionally, correcting the registered first scan images and second scan image comprises correcting said scan images for a plurality of predefined parameters.

Optionally, correcting the registered first scan images and second scan images comprises correcting said scan images for one or more of contrast, brightness, intensity, or scale.

Optionally, determining the mass of the crop from the corrected first and second scan images comprises identifying one or more clusters of fruit in the scan images and analyzing an intensity of the clusters on a pixel by pixel basis. Optionally, the method further comprises summing and correlating the analyzed intensity of the clusters over a predefined period of time.

The present specification also discloses a system for determining a mass of a crop comprising: at least one X-ray scanner for obtaining at least two scan images of the crop, wherein a first of the at least two scan images is obtained along a first plane relative to the crop and a second of the at least two scan images is obtained along a second plane relative to the crop, and wherein the first plane is angularly displaced relative to the second plane; and a controller coupled with the X-ray scanner, wherein the controller is adapted to: register the first and second images; correct the registered first and second images; and determine the mass of the crop from the corrected first and second scan images.

Optionally, the first plane is angularly displaced relative to the second plane by an angle ranging between 90 degrees and 270 degrees.

Optionally, the first plane and the second plane are parallel to each other.

Optionally, registering the first scan image and the second scan image comprises matching the first image and the second image by flipping and translating at least one of the first image and the second image relative to the other.

Optionally, the system comprises two X-ray scanners for obtaining the at least two scan images of the crop simultaneously.

Optionally, the at least one X-ray scanner is used to scan the crop at least two times to obtain the at least two scan images of the crop.

Optionally, correcting the registered first and second scan images comprises correcting said images for a plurality of predefined parameters.

Optionally, correcting the registered first and second scan images comprises correcting said images for one or more of contrast, brightness, intensity, or scale.

Optionally, determining the mass of the crop from the corrected first and second scan images comprises identifying one or more clusters of fruit in the images and analyzing an intensity of the clusters on a pixel by pixel basis.

Optionally, the system further comprises summing and correlating the analyzed intensity of the clusters over a predefined period of time.

The present specification also discloses a system for estimating a weight of crop, wherein the crop comprises at least one row of plants and wherein the at least one row of plants comprises vines and/or branches bearing fruit, the system comprising: at least one X-ray scanner for irradiating a predefined area of the crop with X-rays from at least two sides; and a controller coupled with the at least one X-ray scanner, wherein the controller is adapted to: obtain scan images of the at least one row of plants; perform contrast enhancement and de-noising with respect to each of the collected scan images; perform a global registration of the contrast enhanced, de-noised images; obtain split images by separating vines and/or branches from said images; perform a local registration of the obtained split images; perform a cluster segmentation function on a predefined group of the split images; process the segmented images using distance calibration; and estimate a weight of the crop by using the distance calibrated images.

Optionally, collecting scan image data of at least one row of plants comprises flipping scan images, generated by irradiating the predefined area of the crop with X-rays, in a same predefined direction.

Optionally, obtaining split images comprises cutting out separate vines and/or branches from said images by discarding edges of the vines and/or branches from the images.

Optionally, performing local registration comprises obtaining alignment between pairs of images showing different views of a same plant.

Optionally, the system is used for predicting a yield of the crop using the distance calibrated images.

Optionally, obtaining scan images of at least one row of plants comprises: extracting image data from a raw data file; creating a schematic map of each predefined area; plotting a movement of a vehicle carrying a scanning apparatus being used for irradiating the crop with X-rays on the schematic map; and determining a GPS coordinate of a point on the schematic map by correlating at least one timestamp of one or more GPS coordinates with at least one timestamp of when points on the schematic map were captured.

Optionally, the controller locates rows of plants along with corresponding direction based on a direction of movement of the vehicle; and flips all the located rows of plant in a predefined direction for obtaining a consistent sequence of plants in a row in each obtained scan image.

Optionally, the controller normalizes each obtained scan image by using a predefined normalization bar.

Optionally, the controller directs the X-ray scanner to scan GPS coordinates of each predefined area for obtaining distance between rows of plants in said areas.

Optionally, the controller identifies and annotates the segmented images.

Optionally, the controller processes the split images by using a coarse cluster segmentation method.

Optionally, the controller performs the cluster segmentation function as either a classical cluster segmentation function or a deep learning cluster segmentation function.

Optionally, the controller determines a cluster processing technique for processing each of the split images.

Optionally, the controller determines weight of fruit hanging from plants by determining a change in an X-ray signal backscattered by the fruit over a predefined period of time.

Optionally, the fruit comprises one of: grapes, berries, citrus fruits, apples, melons, and tomatoes.

Optionally, the X-ray signal backscattered from the fruit is proportional to a mass of the fruit and a distance of the fruit from a scanning system generating the X-rays for irradiating the fruit. Optionally, the X-ray signal backscattered from the fruit is proportional to the square of the distance of the fruit from the scanning system.

Optionally, a total mass of the fruit is determined by integrating a signal intensity of X-ray signal backscattered from the fruit across the crop.

In accordance with an embodiment of the present invention, a method is provided for remotely characterizing a living plant. The method has steps of a) generating a first beam of penetrating radiation; b) scanning the beam across the living plant; c) detecting Compton scatter from the living plant derived from the first beam of penetrating radiation to generate a first scatter signal; and d) processing the scatter signal to derive one or more characteristics of the living plant.

In embodiments, it should be noted that Compton backscatter x-ray characterization, and imaging in particular, are sensitive to materials of low effective atomic number, such as water and organic materials.

Some embodiments of the present invention may use a beam where the beam is collimated in one dimension. Other embodiments may use a beam wherein the beam is collimated in two dimensions, referred to as a pencil beam. Some embodiments of the invention may derive a characteristic, such as water content, root structure, branch structure, xylem size, fruit size, fruit shape, fruit aggregate volume, cluster size and shape, fruit maturity and an image of a part of a living plant. In some embodiments, the penetrating radiation may include x-rays. In other embodiments, x-rays may include photons in a range between 50 keV and 220 keV.

Further embodiments of the current invention may acquire data using a concurrent sensing modality. In some embodiments, the sensing modality may include at least one of visible, microwave, terahertz and ultrasound. Other embodiments may use data acquired using a concurrent sensing modality for registration of an image of the living plant with respect to a frame of reference of the living plant. In some embodiments of the invention, the living plant may be irradiated with a pencil beam emitted from a conveyance. In other embodiments, the living plant may be irradiated from above the living plant. Further embodiments may include irradiating the living plant from a position horizontally displaced with respect to the living plant. In other embodiments, the beam may be generated in a scanner head deployed on an articulated arm. Other embodiments may further have a gripper and an x-ray source with pencil beam collimation disposed on a robotic arm. Further embodiments may include deriving a characteristic of a root of the living plant. In other embodiments of the invention, the penetrating radiation may be emitted concurrently into two half spaces. In other embodiments, scanning may include directing the beam of penetrating radiation electronically.

In other embodiments of the invention, the radiation may be passed through a defining aperture. In further embodiments, the defining aperture may be adjusted during the course of scanning the beam. In other embodiments, the scatter may be spectrally resolved. This resolution may be achieved by modulating spectral content of the first beam of penetrating radiation or detection differentially sensitive to distinct spectral features.

In other embodiments of the invention, organic features may be distinguished on the basis of distinctive spectral signatures. In further embodiments of the invention, at least one of position and orientation of a pencil beam in a frame of reference of the living plant may be monitored and the pencil beam may be steered in a closed loop to maintain a specified path of the pencil beam in the frame of reference of the living plant. In other embodiments of the invention, an image of the scatter signal may be registered with respect to the frame of reference of the living plant. In other embodiments of the invention, both a first and second beam of penetrating radiation may be used to generate a second scatter signal and the second scatter signal may be processed to derive a second characteristic of the living plant. In other embodiments of the invention, at least one derived characteristic is associated with water uptake. In further embodiments of the invention, the first and second scatter signals may be used to derive a three-dimensional characteristic of the plant. This derived three-dimensional characteristic may be a stereoscopic image. In other embodiments of the invention, the first and second scatter signals may be used to generate spatial coordinates of the living plant with respect to an ensemble of other living plants, spatial coordinates of the living plant with respect to a base of the living plant, or spatial coordinates of a fruit with respect to another portion of the living plant. In further embodiments, a gripper may be mounted on a robotic arm and a closed loop feedback control system may be used for positioning the gripper. In certain embodiments of the invention, the first and second beams may be scanned from a conveyance. In other embodiments of the invention, the first and second beams may be each scanned relative to respective first and second central rays and may be relatively displaced by an angle. This angle may be in a range between 45 and 135 degrees. In further embodiments of the invention, the first and second scatter signals may be used to generate spatial coordinates of at least one object, other than the living plant, located between the conveyance and the living plant and, using these coordinates, a topographical map may be generated.

In accordance with another embodiment of the present invention, a method is provided for measuring ground water content. The method has the steps of: a) generating a beam of penetrating radiation; b) scanning the beam across the ground; c) detecting Compton scatter from the ground derived from the beam of penetrating radiation; and d) processing a scatter signal from the Compton scatter relative to a reference sample to derive a moisture content of the ground.

In accordance with yet another embodiment of the present invention, a method is provided for guiding motion of a robot. The method has the steps of: a) generating a first beam of penetrating radiation; b) scanning the first beam across a living plant; c) detecting Compton scatter from the living plant derived from the first beam of penetrating radiation to generate a scatter signal; d) processing the scatter signal to derive a characteristic of the living plant; and e) using the derived characteristic of the plant to guide a gripper of the robot to grasp a portion of the living plant.

Further embodiments may include harvesting the plant with the gripper. In other embodiments of the invention, the gripper may be mounted on a robotic arm and the system may use a closed loop feedback control system for positioning the gripper.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 9 shows a fan beam scanning apparatus using fan beam illumination, in accordance with an embodiment of the present specification;

FIG. 11 is a table listing exemplary types of specialty crops where backscatter imaging may be applied, in accordance with embodiments of the present specification;

FIG. 15A illustrates a successful split image, in accordance with an embodiment of the present specification;

FIG. 15B illustrates a split image showing false positives, in accordance with an embodiment of the present specification;

FIG. 16C illustrates a registration of split images by using coarse feature annotation, in accordance with an embodiment of the present specification;

FIG. 16D illustrates a close-up illustration of sides of split images by using coarse feature annotation, in accordance with an embodiment of the present specification;

FIG. 17A illustrates a cluster annotated image, in accordance with an embodiment of the present specification;

FIG. 17B illustrates a coarse segment network, in accordance with an embodiment of the present specification;

FIG. 19A is a graph illustrating a relationship between scatter intensity and cluster size, in accordance with an embodiment of the present specification;

FIG. 19B is a graph illustrating a relationship between scatter signal and distance between scanner and fruit, in accordance with an embodiment of the present specification;

FIG. 20A illustrates a region analysis method, in accordance with an embodiment of the present specification;

DETAILED DESCRIPTION

Figure 1:
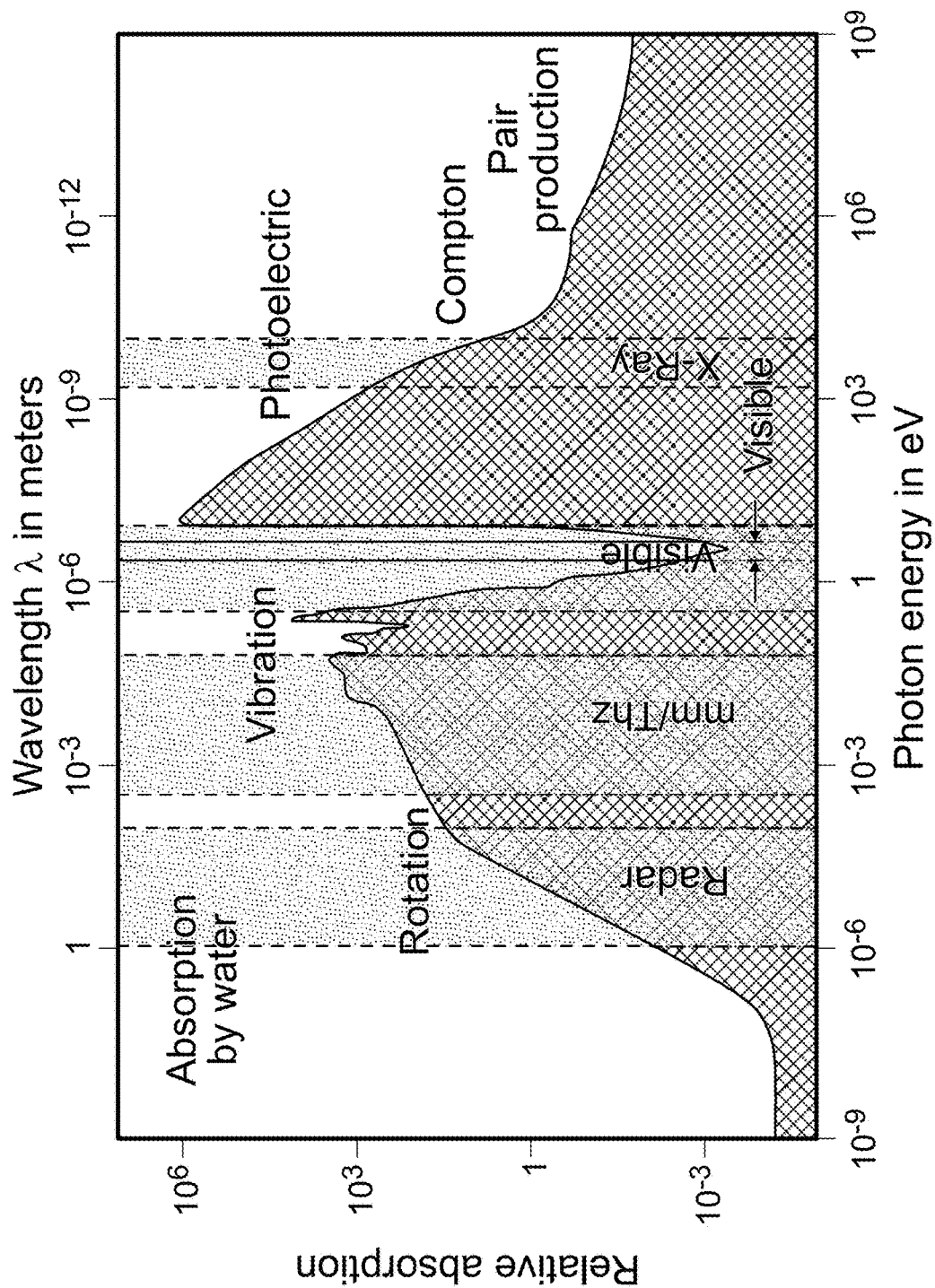
FIG. 1 shows a chart of the relative absorption by water of electromagnetic radiation as a function of wavelength or photon energy.

As recognized for the first time by the present inventors, Compton scattered X-ray radiation in the ~50-220 keV energy range is an ideal probe of both crop size and yield, as this radiation efficiently scatters from water, and appears in bright contrast in Compton X-ray backscatter imaging. X-rays penetrate low density objects such as leaves or branches, and show correspondingly less backscatter signal. The capability to penetrate foliage and generate a signal which is sensitive to water content enables backscatter X-ray imaging to provide highly accurate data over other techniques such as visible, infrared or radar imaging.

The description below provides a detailed teaching as to the application of backscatter imaging to a wide variety of challenges in the area of precision agriculture including yield estimation, development of both crops and plants during the season and year over year, water management, robotic harvesting, and data fusion and management.

It should be noted herein that backscatter imaging for crop yield may advantageously be applied to any crop which has isolated or clustered fruits, including trees, vines, or plants. Crops can vary in types, size, and shape but the scanning method may stay the same, including a linear translation of the imager across the plant according to some embodiments of the invention.

Larger apple and citrus trees are typically grown outdoors, while smaller plants like tomatoes, squash, melons, etc. can be grown in greenhouses or outdoors. In embodiments of this invention, the same base backscatter system may be used for multiple applications, with parameters such as beam spectral content or dwell time modified for a particular application. Further, crop type applications typically differ with respect to how much scan time and power is required. For instance, scanning an unmanaged apple or citrus tree may require much more power and slower scan speed than a managed tree would require. The unmanaged trees have a larger height and diameter that requires imaging of a larger tree height and diameter than managed trees, requiring higher power and energy. This corresponds to higher power and energy. Managed orchards have managed trees where the branches are attached to a trellis. Unmanaged orchards have unmanaged trees which have no trellis structure.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

While X-ray backscatter has been used for the characterization of many materials, it has always been considered impossible to characterize crops in vivo using backscatter techniques, because backscatter techniques are prone to motion-induced geometrical irregularity and variation that is unacceptable in the current application in that a user lacks control over the position and stability of the sample. Without control and regularity in scattering technique, proper crop yield estimations may not be obtained. Crop yield estimation is an important task in the management of a variety of agricultural crops, such as apples, grapes, and cucumbers. Accurate yield prediction helps growers improve the fruit quality and reduce operating costs by making better decisions on intensity of fruit thinning and size of the harvest labor force. Managers may use estimation results to optimize packing and storage capacity. A scanner that is capable of assessing the size and number of produce is applicable to overall crop yield estimation; spatial distribution mapping for watering, fertilizer, and pesticides; detection and damage assessment and mapping for diseases, insects, or other causes of crop loss; temporal analysis of growth rate and development of crops; and testing the efficacy of fertilizers or pesticides.

Fruit crops such as apples, citrus fruits, grapes, and others are composed of starch rich, low density features (leaves, branches, and stems) and fruit which is compact and water saturated. X-ray radiation in the ~100 keV energy range efficiently scatters from water, and appears as a bright contrast in Compton X-ray backscatter imaging. X-rays penetrate low density objects such as leaves or branches, and show correspondingly less backscatter signal.

In addition to the number of crop in the images, a 3D location is also useful in preventing double counting, as well as providing better understanding of the location to target for pesticides and fertilizers. The 3D location may be estimated provided by including multiple X-ray illumination angles. In addition the exact position of the X-ray source may be recorded. In order to correct for non-uniformity in the level of the ground, sensing of the position as well as the orientation of the source is preferably recorded. A Global Positioning System (GPS) may also be used in certain embodiments for positioning in the field, optionally in conjunction with use the use of GPS for fertilization and application of pesticides.

Embodiments of the invention may combine multiple sensing systems onto a mobile conveyance to enable an accurate, rapid, automated detection system for crop yield estimation. Embodiments may include the combination of an X-ray system and position and orientation sensing, which prevents double counting when scanning from both sides of a crop row.

Further embodiments may include an X-ray system which includes multiple viewing angles which may be used to calculate a 3D location of crop. In some embodiments, the X-ray imaging system is optimized in design of source and detectors in order to maximize sensitivity and thus increase the speed of inspection. Specifically, a rapid scan rate may be enabled using a coded-aperture configuration of source and area detector. A complete description of the use of coded aperture X-ray backscatter detection techniques may be found in U.S. Pat. No. 5,940,469, to Huang et al., which is incorporated herein by reference.

Determining the yield in a crop requires measuring the scatter intensity, over a specified spectral range, with a specified spatial resolution, all varying with the crop involved. An example is viticulture, the yield of which may be determined by measuring a variation in scatter in the range of 140 to 220 keV with a resolution of 1-4 mm. In order to screen a growing crop from a distance on the order of 1 meter at a rate of 1 kilometer per hour, one needs a detection sensitivity of 500-600 photons per steradian per second per root Hz. That was considered impossible, prior to the present inventors realizing that a pencil beam X-ray source used to generate Compton back-scatter signal from a moving inspection platform enabled the requisite sensitivity, as did the unique capability of the present invention to penetrate through intervening growth between the fruit and the scanner, as described in detail below.

For the large areas that typically need to be covered (often square miles of scanning), it may not be feasible to scan a pencil beam. For example, to achieve a resolution of 1 mm$^2$ from a standoff distance of 1 m implies an angular resolution of $10^{-6}$ sr, or 0.06° of aperture in a rotating hoop. A calculation of signal-to-noise based on an incident flux of 5×108 photons/sec/cm$^2$/mA, a standoff distance of 1 m, and a representative beam spectrum, suggests a dwell time of at least 2.5 μs per pixel for a pencil beam produced by a rotating aperture. This implies a rotation rate of 3,000 revolutions per second of an aperture hoop.

A scene including fruit that are 1 m high filling a square of 10 acres in rows spaced 3 m apart would encompass ~1010 pixels, thus requiring 24 hours to scan such a field with a pencil beam. Under many circumstances, such a scan could not provide data on a timescale useful for agricultural insight. A fan beam, or, alternatively, a cone beam using coded aperture techniques, may be used advantageously to increase the flux and thus the scan rate by a factor of over 100 times. In the case of a fan beam, this simply derives from the concurrent detection of ~100 collinear pixels.

For example, in the field of viticulture, a square vineyard of 1 acre with a row spacing of 130 in may be scanned in 0.3 hours, based on a 160 keV X-ray source at 1000 W dissipation, employing a chopper wheel with 8 spokes rotating at 1800 rpm, scanning simultaneously in both directions to acquire bilateral data, with motion along the rows at a speed of 2.18 mph.

Definitions: A "conveyance" shall be any device characterized by a platform borne on ground-contacting members such as wheels, tracks, treads, skids, etc., used for transporting equipment from one location to another.

The word "trailer," as used herein and in any appended claims, shall refer to a conveyance adapted to be drawn over an underlying surface by a motorized vehicle or conveyance that may be referred to herein as a "tractor."

The word "image," as used herein and in any appended claims, shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one there onto. Thus, for example, the graphic display of the spatial distribution of some field, either scalar or vectorial, such as brightness or color, or X-ray scatter intensity, etc., constitutes an image. So, also, does an array of numbers, such as a 3D holographic dataset, in a computer memory or holographic medium. Similarly, "imaging" refers to the rendering of a stated physical characteristic in terms of one or more images.

The term "X-ray source" shall signify a device that produces X-rays, including, without limitation, X-ray tubes, or Bremsstrahlung targets impinged upon by energetic particles, without regard for the mechanism used to generate the X-rays, including, without limitation, linacs, etc.

A "half space" shall refer to each of the two parts into which an imaginary plane divides three-dimensional space.

A "living plant" shall refer to an unharvested plant, which is to say that a living plant remains attached to the source of nutrient that provides for its growth. Further, for purposes of the present description, plant matter shall be said to be "living" if it is consuming energy in a process of growth.

A "gripper," otherwise referred to in the art as "end of arm tooling," is a remotely operated device for holding and manipulating objects. It may be a claw, a bag, a suction device, etc., as well known in the art, and as encompassed within the scope of the present invention.

A "robotic arm" is an actuated mechanical linkage coupling a gripper to a base, where the base may be vehicle or other conveyance.

As used herein, the term "part," referring to an object, shall encompass a portion or the entirety of the object.

A "scanner" is a device for moving the direction of propagation of a beam. Examples of scanners that may be used with X-ray beams are described, for example, in U.S. Pat. No. 9,014,339 ("Versatile X-Ray Beam Scanner," to Grodzins et al.), and include mechanical scanners, such as rotating hoops, X-ray tubes with rotating anode apertures, as described in U.S. Pat. No. 9,099,279 (X-Ray Tube with Rotating Anode Aperture," to Rommel et al.) or electronic scanners, as described, for example, in U.S. Pat. No. 6,282, 260 ("Unilateral Hand-held X-Ray Inspection Apparatus," to Grodzins). All such scanners are within the scope of the present invention.

The term "scanning head" is used to refer, more generally, to hardware that directs a beam, and, for example, may include the source of radiation that is scanned by the scanner.

A "scanning apparatus" shall refer to a system for characterizing a scanned object or scene on the basis of radiation (such as X-rays) that is scanned across the scene. The scanning apparatus may include detectors for detecting scattered radiation, and may also include a conveyance for transporting the scanning head and detectors as well as ancillary equipment such as power supplies, sensors, etc.

A "fan beam" is a beam that is collimated in one dimension transverse to a propagation direction of the beam.

A "pencil beam" is a beam that is collimated in two dimensions transverse to a propagation direction of the beam.

An "organic feature" is a feature of organic matter, such as a plant, that distinguishes the matter from inorganic matter. Organic features may include, but are not limited to water content, root structure, branch structure, xylem size, fruit size, fruit shape, fruit aggregate volume, cluster size, cluster shape, and fruit maturity.

A "ground truth vine" is a vine which is monitored over a predefined period of time, imaged before and after harvesting and weighing.

In various embodiments, the system of the present specification includes a computing device having one or more processors or central processing unit, one or more computer-readable storage media such as RAM, hard disk, or any other optical or magnetic media, a controller such as an input/output controller, at least one communication interface and a system memory. The system memory includes at least one random access memory (RAM) and at least one read-only memory (ROM). In embodiments, the memory includes a database for storing raw X-ray data, scan images, and processed images and data related to these images. The plurality of functional and operational elements is in communication with the central processing unit (CPU) to enable operation of the computing device. In various embodiments, the computing device may be a conventional standalone computer or alternatively, the functions of the computing device may be distributed across a network of multiple computer systems and architectures and/or a cloud computing system. In some embodiments, execution of a plurality of sequences of programmatic instructions or code, which are stored in one or more non-volatile memories, enable or cause the CPU of the computing device to perform various functions and processes such as, for example, receiving raw X-ray data, such as image data, and applying various processing steps (such as, but not limited to contrast enhancement, de-noising, global registration, local registration, cluster processing, cluster segmentation, deep learning processes, calibration, and weight estimation) for providing images and other data, such as but not limited to crop weight or yield information, for display on a screen. In alternate embodiments, hard-wired circuitry may be used in place of, or in combination with, software instructions for implementation of the processes of systems and methods described in this application. Thus, the systems and methods described are not limited to any specific combination of hardware and software.

Backscatter imaging utilizes a pencil beam of X-ray radiation which irradiates an object and detection of Compton scattered radiation from the object. The contrast in back-scatter imaging is dependent on the composition of the material. Biological materials, which are composed of low atomic number materials including hydrogen, carbon, nitrogen, and oxygen have a strong contrast in backscatter X-ray imaging due to two competing effects of Compton scatter generation and X-ray absorption. The Compton scatter cross section rises in direct proportion with atomic number (Z), so higher Z materials scatter more. However, photoelectric absorption is proportional to $Z4/E3$, so for higher Z, particularly at lower energies, photoelectric absorption prevents the Compton scattered X-rays from leaving the target material. Compton scattered X-ray radiation in the ~50-220 keV energy range is an ideal probe of both crop size and yield, as this radiation efficiently scatters from water, and appears as a bright contrast in Compton X-ray backscatter imaging. This energy is used for depth penetration of the soil and/or imaging the root of the plant. While operation in the ~50-220 keV range is described, the range is provided by way of example and is provided for no limiting intent.

The absorption spectrum of water vapor, plotted in FIG. 1 as a function of wavelength (in meters) or photon energy (in eV), highlights significant attenuation in the region shortward of the visible spectrum, dominated in the X-ray region by the photoelectric effect. Thus, shorter wavelength radiation would not suggest itself for detection, imaging, or any characterization of crops from any substantial standoff distance, as required in an agricultural context. Because at shorter wavelengths imaging performance gets progressively worse, it is counter-intuitive that radiation penetration, scattering, and imaging performance for Compton scattered X-ray imaging meet all criteria required to achieve good performance for yield estimation.

Backscatter imaging for crop yield may advantageously be applied to any crop which has isolated or clustered fruits, including trees, vines, or plants. Crops can vary in types, size, and shape but the scanning method may stay the same, including a linear translation of the imager across the plant according to some embodiments of the invention.

Larger apple and citrus trees are typically grown outdoors, while smaller plants like tomatoes, squash, melons, etc. can be grown in greenhouses or outdoors. In embodiments of this invention, the same base backscatter system may be used for multiple applications, with parameters such as beam spectral content or dwell time modified for a particular application.

Figure 2:
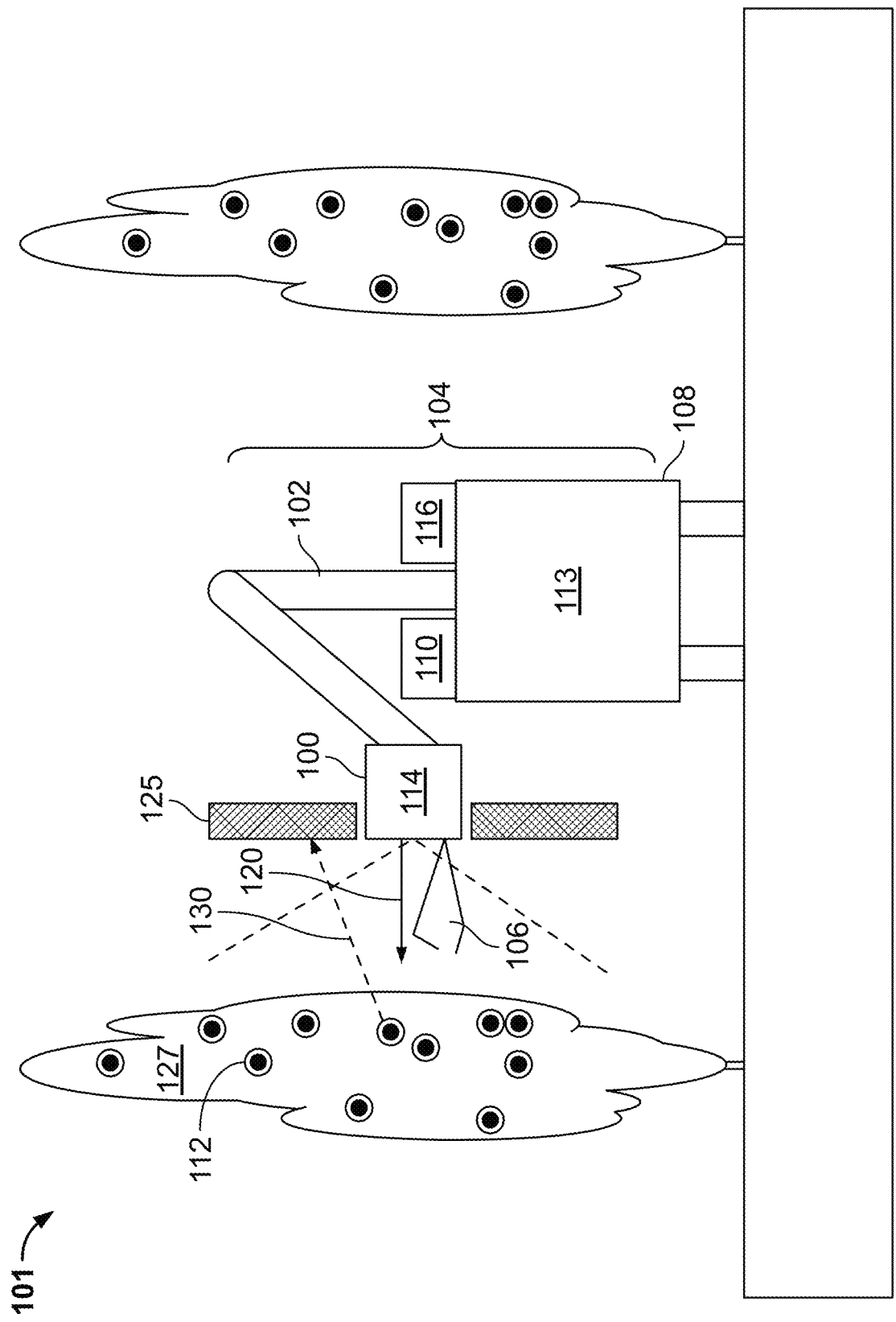
FIG. 2 shows a rear view of a horizontal backscatter scanning apparatus, in accordance with an embodiment of the present specification.

In accordance with certain embodiments of the present invention, a scanning apparatus, designated generally by numeral 101 in FIG. 2, has a scan heads that sits at the end of an arm assembly. Scanning apparatus 101 may be used in horizontal scanning or top down scanning.

FIG. 2 shows a rear view of a horizontal backscatter scanning apparatus 101, in accordance with an embodiment of the present invention. In this embodiment, a scanner head 100 is mounted on an arm 102 of a robot 104. Furthermore, a gripper 106 is also coupled to an arm 102 of robot 104. Robot 104 may be carried on a conveyance 108, be self-propelled, or may be autonomous or guided. In some embodiments of the invention, the conveyance 108, as defined above, is a tractor, truck, or motorized cart. Additionally, the conveyance may have scanning electronics 113 and one or more sensors 110. In some embodiments, the horizontal backscatter scanning apparatus 101 may advantageously use Compton backscatter X-ray imaging, which is sensitive to low atomic number, including water and organic materials. Compton backscatter X-ray imaging may advantageously be used to detect fruit 112, which generally contain concentrated amounts of water.

To perform position sensing in some embodiments, the location of multiple data streams, such as X-ray, visible, microwave, submillimeter, and infrared, for example, may be co-registered. In some embodiments, a position sensing apparatus 116 may determine the location of the conveyance 108 at any given time. The position is preferably determined with accuracy of up to ⅕ the size of the smallest feature required to image. The orientation of the conveyance 108 may also be recorded in some embodiments to preserve the relative illumination angle and position of the X-ray source 114 with respect to the crop.

In some embodiments of the invention, image resolution is proportional to X-ray source power and inversely proportional to scan speed. Crop type applications typically differ with respect to how much scan time and power is required. For instance, scanning an unmanaged apple or citrus tree may require much more power and slower scan speed than a managed tree would require. The unmanaged trees have a larger height and diameter that requires imaging of a larger tree height and diameter than managed trees, requiring higher power and energy. This corresponds to higher power and energy. Managed orchards have managed trees where the branches are attached to a trellis. Unmanaged orchards have unmanaged trees which have no trellis structure.

An X-ray beam produced by Bremsstrahlung contains photons of energies up to an end-point energy that is equal to the energy of the highest-energy electron hitting the Bremsstrahlung target. When an X-ray beam is characterized herein simply by an energy, that energy shall refer to the end-point energy of the beam. Thus, a first X-ray beam will be said to be of a higher energy than a second X-ray beam if the end-point energy of the first X-ray beam exceeds that of the second X-ray beam.

Ripened crops are composed of relatively high concentration of water, carbon and nitrogen, relative to the surrounding branch and foliage materials, referred to herein as "intervening material." Referring further to FIG. 2, for a pencil beam 120 striking fruit 112, the Compton scatter signal will increase with the radius of the fruit for some, but not for all, spectra of incident X-rays, because of multiple processes of scatter and absorption which occur in the crop, as readily calculated. Pencil beam 120 may also be referred to herein as an "input beam" or as a "scanning beam." As the scanning 120 beam passes through the thickness of plant 127, constituting the crop, a portion of the input beam 120 is scattered from the plant 127. Plant 127, insofar as it scatters X-rays, may also be referred to herein as an "object" and, insofar as input beam 120 traverses plant 127, it may also be referred to as "material."

Radiation for input beam 120 that is scattered by fruit 112, also referred to herein as scatter radiation 130 (or as "backscattered X-rays"), now has to pass back through that same intervening material in order to return to detector 125. Each photon of the backscattered X-rays 130 has a lower energy than that of the photon of incident beam 120 giving rise to the scatter, and will be attenuated by the outgoing intervening material. "Outgoing intervening material" refers to the path through plant 127 traversed by scattered radiation 130 en route to detector 125. The effect of energy transfer due to Compton scatter is a function of both scatter angle and energy. For foliage and small diameter crops such as citrus or apple, the scattered radiation is not strongly attenuated through the thickness of the fruit itself, however, for very large crops such as melons, significant attenuation of the backscattered X-rays may occur within the fruit itself. In either case, the high scatter of the fruit relative to the low scatter of the intervening material emphasizes the fruit in the detected scatter signal.

In some embodiments, a horizontal backscatter scanning apparatus 101 can scan the plants, fruits, or trees by scanning out of the side of the conveyance 108. This configuration can either have one scanner 100 or dual scanners, as in FIG. 3.

Figure 3:
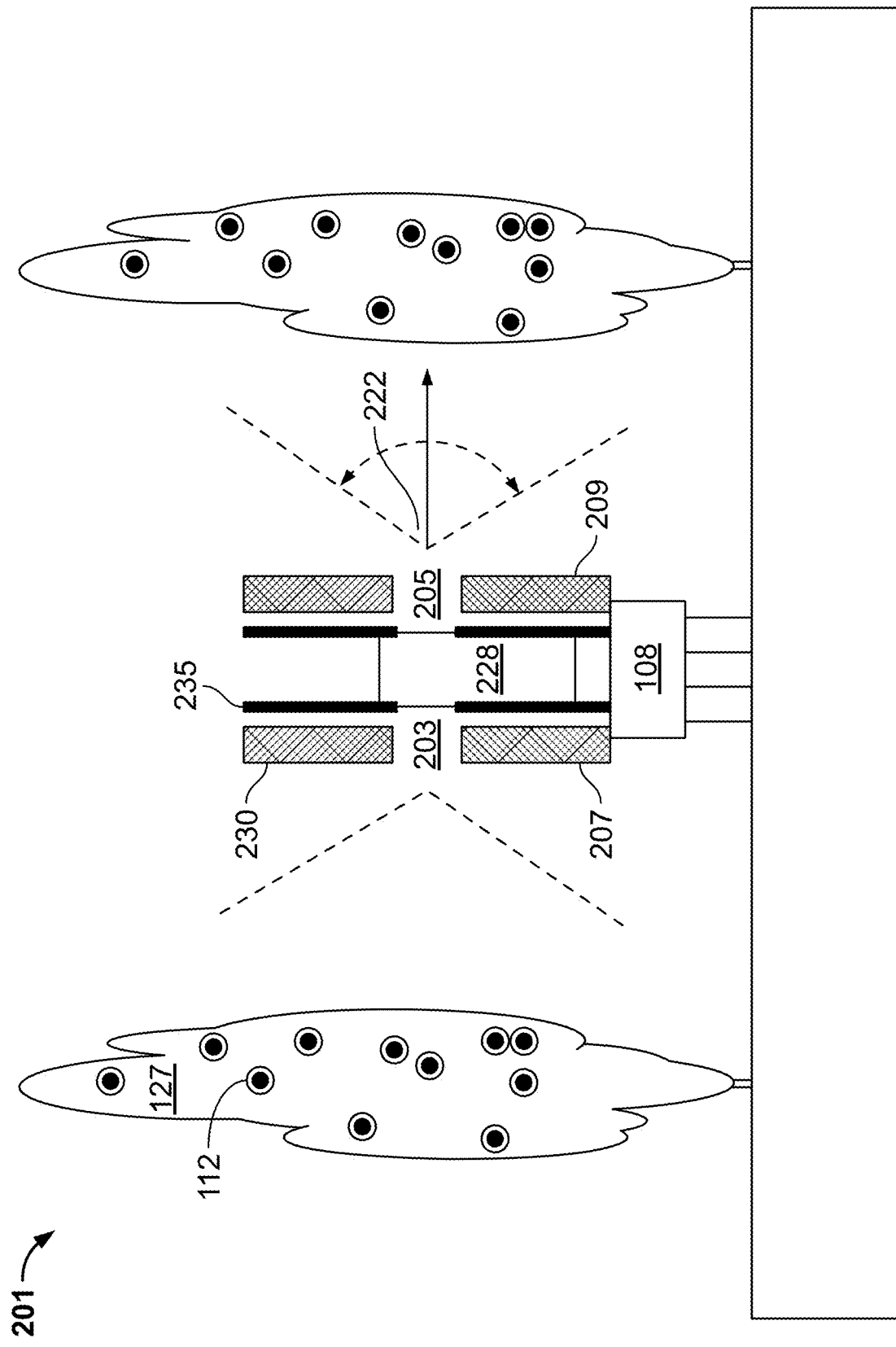
FIG. 3 shows a dual-sided scanning apparatus, in accordance with an embodiment of the present specification.

FIG. 3 depicts a dual sided horizontal backscatter scanning apparatus, designated generally by number 201, in accordance with an embodiment of the present invention. In some embodiments of the invention, multiple backscatter X-ray scanner heads 203, 205 are positioned in close proximity to the plant 127 and allow a full view of the region where the crop can grow. X-ray source 228 produces X-rays scanned by scanners 203 and 205 to create scanned beams 222 for scanning a plurality of rows at a time (e.g., each side of the scanner). Where multiply-directed beams are employed, shielding 235 prevents detection of scatter by oppositely directed detectors 203.

A scanning apparatus (such as dual-sided horizontal backscatter scanning apparatus 201) that is used for X-ray imaging may also be referred to herein as an "X-ray imager." X-ray imager 201 may operate continuously or intermittently when conveyance 108 is in motion. Imaging systems may employ a flying spot/pencil beam 222, fan beam imaging, or coded-aperture imaging, for example, within the scope of the present. In accordance with various embodiments of the present invention, three-dimensional information may be gathered in a dual-scanner configuration 201. In other embodiments, three-dimensional information may be gathered by including a single system which acquires images at variable angles by rotation of the imaging system 201 at periodic intervals. In some embodiments, inclusion of multiple imaging scanners 203, 205 on the conveyance 108 with different view angles, wherein the conveyance 108 continuously records backscatter signal or coded aperture imaging for multiple angles, may be used to acquire 3D information. In addition to X-ray detectors 230 (also referred to herein as X-ray sensors), additional sensing in certain embodiments may be included to provide accurate information as to the position and orientation of conveyance 108 within the frame of reference of crop 127. This provides for governing the orientation of beam 222 or for using a tracked position to register a backscatter signal within an acquired image (shown in FIG. 6). This may advantageously improve the capability for measuring the size of the crop 127 and/or the volume of the crop 127. Ghz/Thz radiation, thermal/IR, and ultra-sound technologies may also be combined with X-ray data to produce a 3D image of the scanned scene.

Figure 4:
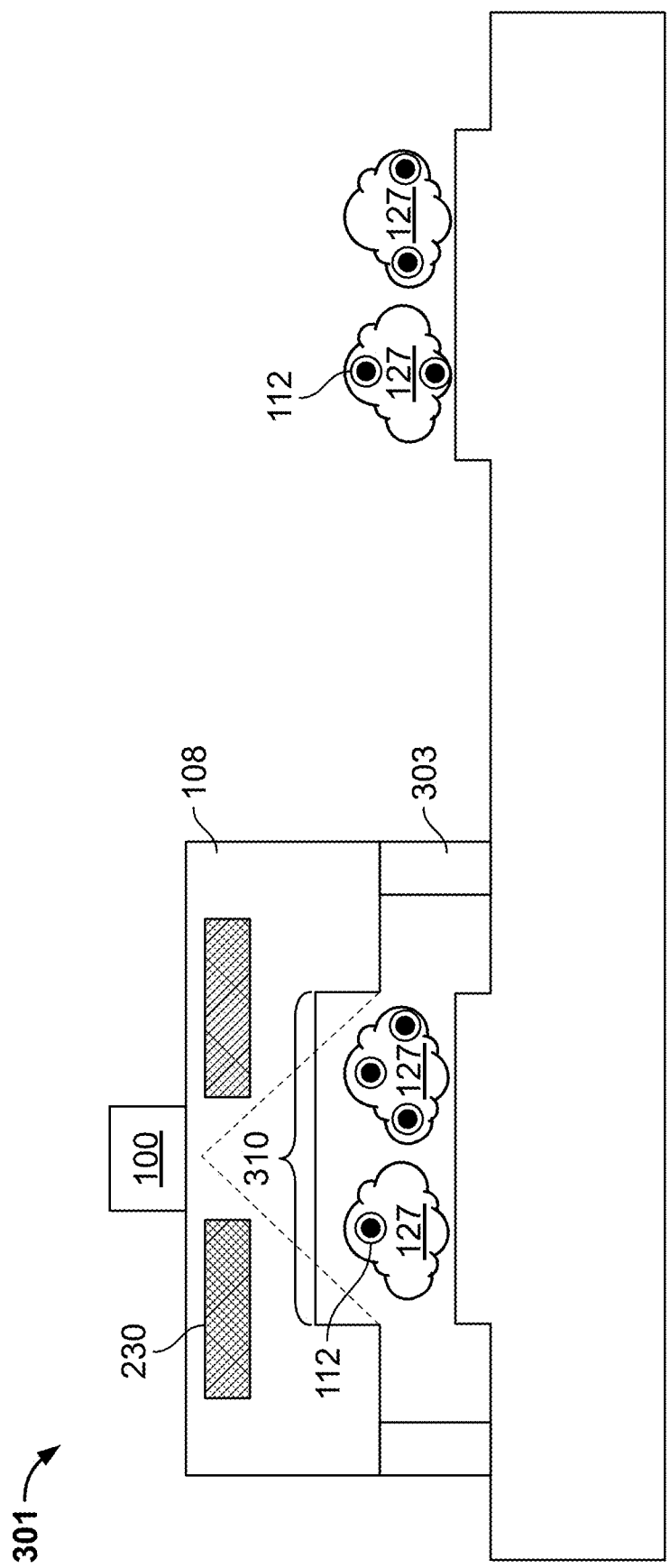
FIG. 4 shows a view of a top-down backscatter scanning apparatus, in accordance with an embodiment of the present specification.

FIG. 4 shows a view of a top down backscatter scanning apparatus designated generally by numeral 301, in accordance with an embodiment of the present invention. Top down backscatter scanning apparatus 301 has a field of view 310 including crop 127. In some embodiments, an adjustable height gantry 303 can be provided for crops with multiple heights. Top down scanning can be used for plants such as strawberries. If the height of the scanning apparatus 301 is increased, multiple results may be obtained at a time in accordance with embodiments of the invention. In some embodiments of the invention, a scan head 305 coupled to the conveyance 108 is coupled to existing sprayer equipment to reduce the grower's implementation costs.

Scanner head 100 may emit X-rays covering a width approximately 4-5 ft. A large detection area of X-ray detectors 230 will increase the flux detected and thus increase the rate of scanning. Where crops such as cotton, melons, etc., may not allow enough space for side illumination from the top is preferred. X-ray flux may be increased to increase the rate of scanning, however if additional flux is achieved by increasing the aperture size, it is at the cost of image resolution. For a typical apparatus 301, beam apertures of up to 4 mm in size can be utilized. In some embodiments, for imaging of point objects which have a repetitive shape, a coded aperture imaging system may allow for more efficient imaging. In the case of fruit crops where the objects are identical in shape, but change in size and location, a coded aperture X-ray imaging system may be used to efficiently determine the location and size of the objects in the field of view. Because the imaging system allows illumination of the full area, the flux delivered to the crop in coded aperture systems can be significantly higher. This may advantageously increase the rate of scanning of the system.

Figure 5:
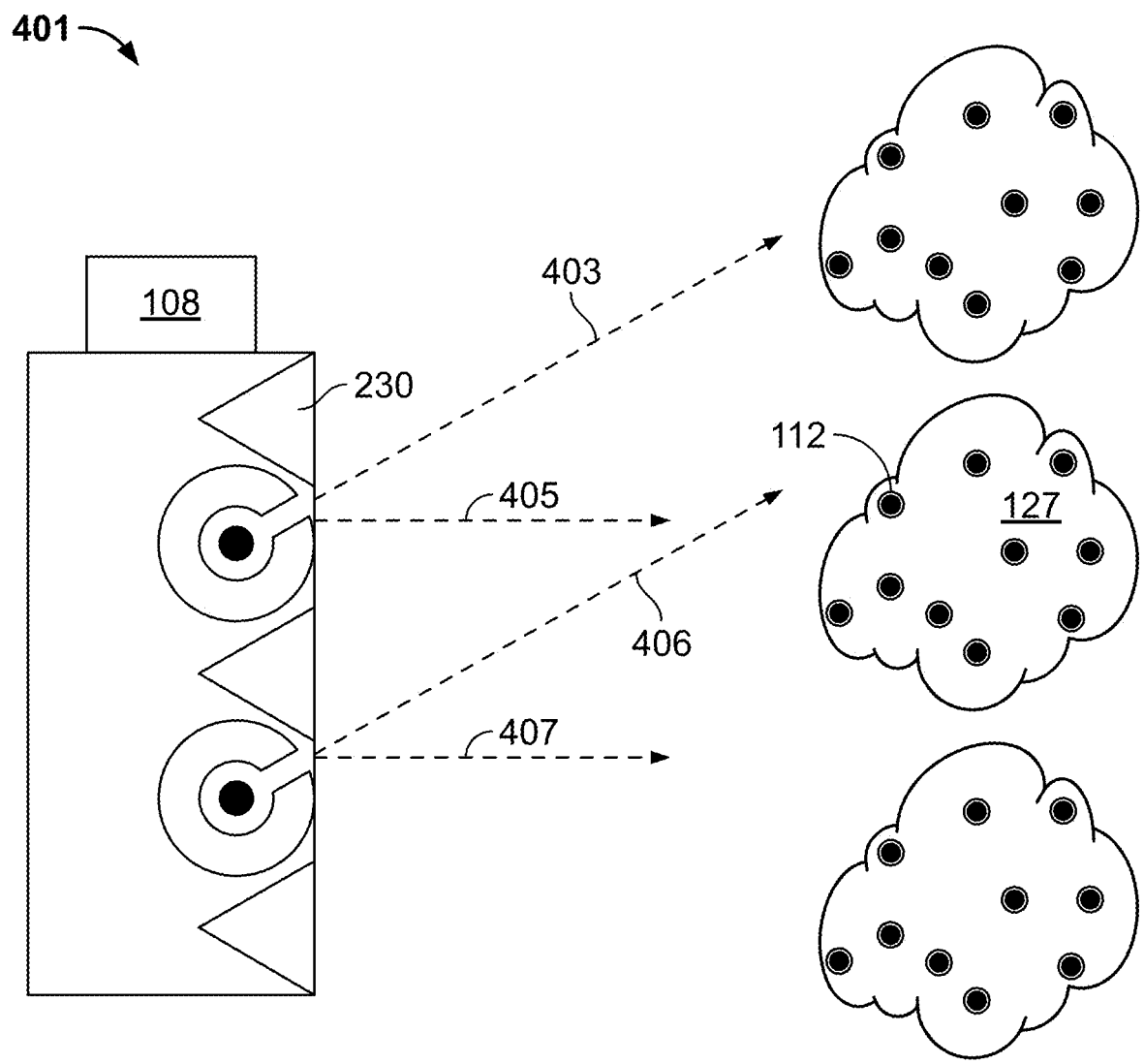
FIG. 5 shows an exemplary dual energy detector scanning apparatus, in accordance with an embodiment of the present specification.

FIG. 5 shows an exemplary dual-scanner scanning apparatus, designated generally by numeral 401, in accordance with an embodiment of the present invention. First and second beams 403 and 406 may be scanned from a conveyance 108. In other embodiments of the invention, the first and second beams may be each scanned relative to respective first and second central rays 405 and 407 and may be relatively displaced by an angle. While first and second central rays 405 and 407 are parallel in the embodiment shown, the angle between first and second central rays 405 and 407 may be in a range between 45 and 135 degrees in other embodiments. Emission of beams 403 and 406 is suitably phased so that the origin of a scattered photon reaching detector 230 is unambiguous.

Figure 6:
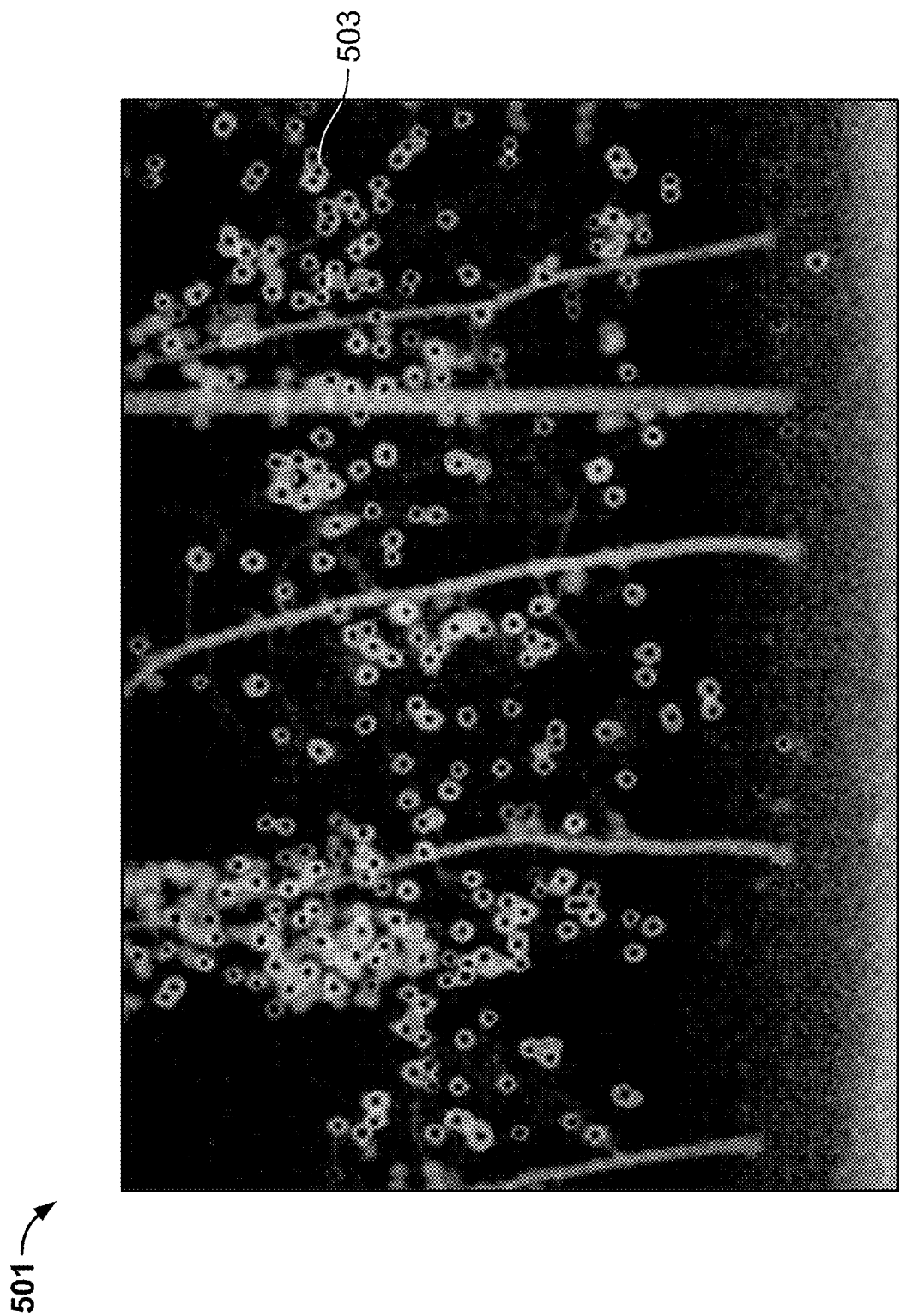
FIG. 6 shows an exemplary X-ray backscatter image of an agricultural scene, in accordance with an embodiment of the present specification.

FIG. 6 shows an exemplary X-ray backscatter image of an agricultural scene, as designated generally by numeral 501, produced in accordance with an embodiment of the present invention. In some embodiments of the invention, crop yield mapping may consist of four pieces of information; fruit size, fruit count, plant location and date/time. Fruit 503 may be highlighted in image 501 to aid in acquiring the characterizing data discussed above. To help aid in historical data, in some embodiments, a scanning apparatus may be coupled to a GPS unit to monitor the location of a fruit or plant. The data may be collected, correlated and stored in a database. Reporting may be generated for the grower to reflect the collected data to the grower. With historical data for the same plants/trees, crop health may be advantageously tracked from year to year, in accordance with an embodiment of the invention.

In addition to backscatter imaging data for yield and plant health, other sources of data may be combined to build a full understanding of the local environment in accordance with certain embodiments. These may advantageously include temperature, humidity, soil conditions and more.

In some embodiments, software may have an easy-to-understand graphical user interface that allows the grower to access and display various pieces of information into an easy to read interface. In certain embodiments, reports and graphical representation of the historical data for a plant, and for the crop, may be included. This data may include plant health, crop health, crop yield, individual plant health and growth and a variety of other data.

Figure 7:
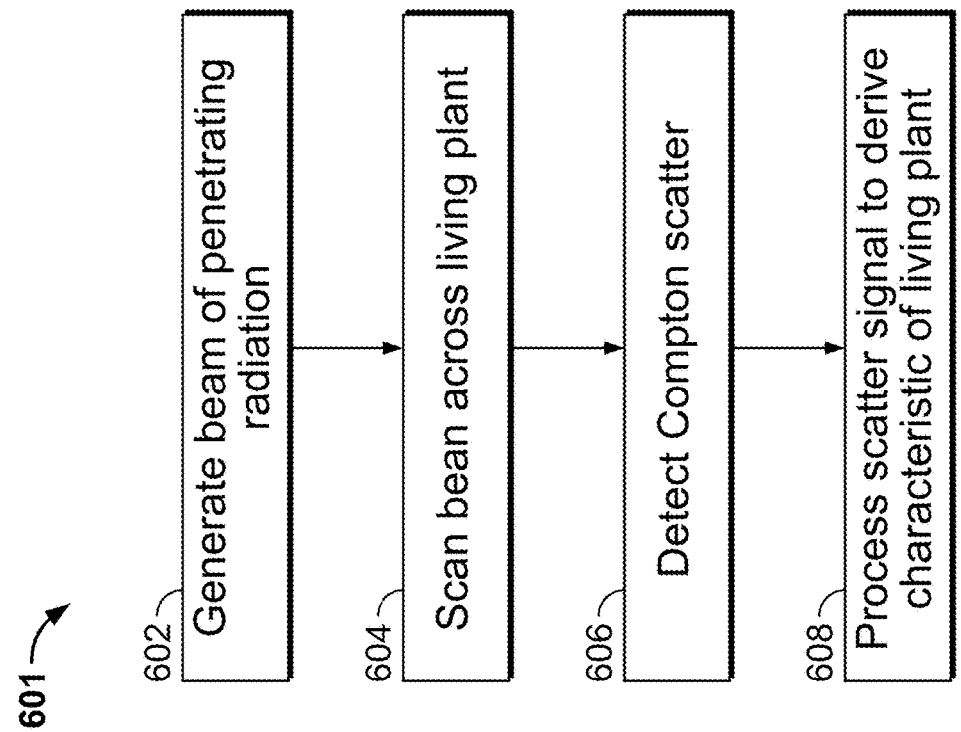
FIG. 7 shows a flow chart depicting steps of a method of scanning, in accordance with an embodiment of the present specification.

Methods in accordance with embodiments of the present invention are now described with reference to the flowcharts of FIGS. 7 and 8. FIG. 7 shows a flow chart depicting steps of a method for scanning living plants, designated generally by numeral 601, in accordance with an embodiment of the present invention. Specifically, the method for scanning 601 may identify a characteristic of a living plant, such as an organic feature, where features that are considered to be organic are defined above. In some embodiments of the invention, software algorithms may improve on the noise rejection, double-counting resolution and crop size/distribution estimation. In addition algorithms may be used to indicate which crops need more or less water/fertilizer by mapping the fields.

In a first step 602, a beam of penetrating radiation is generated. It is to be understood that the source may be temporally modulated, within the scope of any embodiment of the present invention. In process 604, the generated beam is scanned across a living plant. In process 606, detection of Compton scatter is performed using at least one scatter detector. In some embodiments of the present invention, detection is performed using multiple scatter detectors 125 (shown in FIG. 2) or otherwise, such that one signal preferentially registers high-energy scatter, while a second signal preferentially registers low energy scatter. High energy scatter and low energy are terms that are defined with respect to each other, and are used herein to indicate that energy resolution is provided, either by varying the energy distribution of incident X-rays or by energy-resolution of detected scattering, all in accordance with known multiple-energy techniques. Where energy resolution is employed, a ratio of the backscatter signal from the low energy to high energy scatter detection is calculated in process 608. This calculation is further explained in U.S. Pat. No. 8,442,186, incorporated herein by reference. It is to be understood that the term "ratio" as used herein, encompasses weighted or corrected ratios, logarithmic differences, etc. Once the ratio of the low energy to high energy scatter signal has been calculated, it is compared with a threshold value to determine a characteristic of the living plant (608).

In preferred embodiments of the invention, the value of the ratio R between detection at distinct energy spectra is compared with a specified threshold value on a pixel-by-pixel basis in the image, allowing a determination to be made for every pixel in the image. In actual systems used for plant inspection, however, the X-ray intensity is typically insufficient to allow the value of R to be calculated for a single pixel to the required accuracy, due to the limited number of scattered photons that can be detected in the integration time of a single pixel. For this reason, a subregion of the image consisting of many pixels, for example a 10×10 area, can be analyzed, and the value of R calculated from the summed backscatter signals from all the pixels in the subregion.

In further embodiments of the invention, software algorithms may be used for size estimation, process and eliminate double counting, and determine position of crop in 3D. In some embodiments, size estimation algorithms are used to determine features in the scan image.

In some embodiments, software algorithms may be used for size estimation. Backscatter X-rays generate high contrast, isolated scattering features in images. Software algorithms can be used to deconvolve the fruit size using the known aperture response function. Utilizing the de-convolved image, the size of the fruit can be estimated.

Additionally, algorithms can be used to reject features which are not compact and isolated. These features may include branches, stems, or leaves. In further embodiments, image processing software may be combined with position data to eliminate double counting utilizing data from scans on both sides of a row. Embodiments may also use 3D reconstruction algorithms, using both position and orientation information for the conveyance and multiple angle views of X-ray illumination.

In other embodiments of the invention, plant health is determined by monitoring the water content in the trunk of the plant. By varying the energy level of the backscatter source, the water content of the plant can be seen just below the bark of the tree in the cambium layer. By comparing tree to tree, an imaging processing algorithm can figure out which tree has less water and which trees are healthy. Similarly, using higher energy and directing the scans to the root systems, the backscatter can penetrate the less dense soil to determine some root structure, according to embodiments of the invention. The scans can also determine if there soil is damp enough for proper plant growth. The less dense the soil allows the backscatter single to penetrate deeper to allow better examination of the root system.

Furthermore, in other embodiments, algorithms may be used to track root structure and overall plant health. For plants like strawberries, the root system is near the surface and since the roots have more water content than the soil the roots stand out and can be mapped similarly to the branches. The length and thickness of the roots are measured in certain embodiments and compared to a historical reference with respect to plant maturity and determination can be made as to the plant health Further embodiments of the invention may scan for soil moisture content. In some embodiments, the algorithm may have historical reference level with respect to water content for that local vicinity for both wet and dry soil samples. From the image of the soil scan, the water content signal level can be monitored to determine if the ground is moist enough for the plants.

In the precision agriculture industry, it can be important to determine the crop health as the plants grow. To aid in crop health, according to some embodiments, backscatter scanning can be taken along the developmental process.

In some embodiments, scanning can be used post-budding. For apples and citrus crops, post-budding usually occurs when the fruit is a few millimeters in diameter. In this stage the fruit can be culled if diseased (too small or irregular shape) or if the fruit is clustered. If clustered the fruit can be culled to reduce the number of fruit in the cluster, therefore, preventing damaged fruit later in the growth stage. In some embodiments, scanning at post budding stage can be used to determine fruit count and locate clustering.

Scanning can locate the fruit clusters and also count the emerging fruit. In the smaller plants root structure can be scanned to determine the proper development of the plant. Image processing routines can determine if the root is strong and developed enough to bring fruit to maturity.

In other embodiments, scanning can be used mid-growth. Shortly after the post budding stage, the tree tends to cull the fruit as its own survival of the fittest. After this self-culling process the tree usually retains the remaining fruit until maturity. Scanning the crop when the fruit is between 30 to 40 millimeters, such as apples or citrus fruits, will give an accurate yield estimation at maturity for the growers. At this scanning stage the grower can keep and accurate understanding of how much fruit is lost during the culling stages.

In other embodiments, scanning is used to determine crop health. Since the fruit is mostly made of water and has a strong backscatter signal, crop health can be monitored as the fruit grows. Also branch structure can be monitored as another mechanism to determine the tree heath. By varying the energy from a higher energy (e.g. >100 KeV) to a lower energy (e.g. 50 KeV), the canopy can be evaluated since the softer X-rays may cause more signal return for the leaves in other embodiments. Also, in further embodiments, by fusing backscatter with optical imagery and using signal processing the canopy can be evaluated more precisely from a moisture content (scanning with backscatter X-rays) and optical to determine color and size.

Backscatter scans may also be used, in certain embodiments, to determine maturity of the crop. Just prior to maturity (e.g. a few weeks prior to pick) backscatter scans can attain actual crop yield including count and size can be calculated so growers can determine work force to pick (or automated with backscatter), amount of packaging material required, determine market price, and profits and losses can be known prior to pick.

As the fruit ripens the water content of the fruit increases significantly and can get up to 85%-90% of the fruit volume. This excessive water allows the backscatter returned signal to give a much more accurate representation of the fruit. With this newer information the size, shape and count can be more accurately determined to give the grower very accurate information on crop yield (e.g. crop volume).

This volume information allows the grower to accurately plan and determine the labor required for picking the fruit, packaging material required, set market price and profits and losses.

Embodiments of the invention may also advantageously be used for disease detection. Disease is a major issue with growers because it reduces the overall profit of the crop. Disease can also mean parasite or insect damage/infestation. By performing several in season backscatter scans on the crop, the healthy plants will have an adequate amount of water in the fruits and branches. By varying the energy level the canopy can also be examined for water content. Some larvae and insects can be spotted in certain embodiments but they need to be of sufficient size and density for the backscatter to pick up.

Embodiments of the invention can also be used to monitor and track plant development and health. This may include, but is not limited to, branch structure and mapping, foliage mapping, root mapping, and trunk structure.

By using the backscatter scanning, image processing can map the branch growth structure during the season and from year to year in certain embodiments of the invention. This is a good indication of plant health since the branches usually grow during the season at various rates depending on the plant/tree variety. Understanding the growth from year to year can give the grower valuable information to determine if the plant/tree needs replacement or the plants need more or less fertilizer and/or water.

As the plant matures during the season the canopy starts out thin and usually early on in the development for the season the canopy thickens and at approximately mid-season the canopy may be full. During the season the foliage can be mapped, in certain embodiments, through the backscatter scanning to ensure the canopy is growing properly. A plant canopy can be compared to adjacent plants and also other plants in the field to determine any patterns which could be the result of plant disease, insects, parasites, watering issues or fertilizer issues. The backscatter image can be processed for leaf size and water content (signal return amplitude).

The plant root system is critical for the plant health. In some embodiments, by using high energy (e.g. >140 Key) the scanner can scan the ground around the plant such as strawberries and get an image of the near surface root structure. The roots are full of water content and will stand out. By processing the image and giving the grower the root information the grower can then decide if the plant needs to be replaced early on in the development so the plant still has time to bear fruit. Without embodiments of this invention, the grower may have to wait until later in the growing season to determine root health, when it may be too late by noticing stunted plant growth.

The internal portion of the trunk of a plant contains the heartwood, which is dead material from previous xylem growth and does not contain water being transported in the plant. Because the water content and density in the heartwood and xylem are different, imaging of the trunk may distinguish these two layers, in accordance with certain embodiments. The dimensions as well as the relative strength of the backscatter signal in the heartwood and xylem could be used as a gauge of the tree health.

Embodiments of the invention may be used to detect ground water and water uptake. In certain embodiments of the invention, the X-ray backscatter signal is modulated by the water content in the soil. The backscatter signal may also be attenuated by the soil, preventing the system from detecting water content deeper than >3-4". The depth sensitivity of the X-ray backscatter signal will be dependent on the soil composition and density, in accordance with certain embodiments. The backscatter imaging system can map out relative changes in the water content in the soil. The soil with low water will have a weak backscatter signal indicating the area is dry. One example method for measuring water content is as follows: take reference sample scans of soil with varying moisture conditions. The reference scan can be used to construct a correlation or look-up table relating backscatter signal and water content. The reference scans can then be used to gauge relative moisture content where the soil composition remains constant.

Furthermore, in accordance with certain embodiments, the X-ray backscatter signal may be used as a gauge of the water content in plants. For example, the trunk and branches of a plant can be imaged with a backscatter X-ray system to determine if the plant is receiving adequate water and also indicate a diseased condition preventing the uptake of water. Water transport in trees occurs in the sapwood or xylem which is at the outer diameter of the trunk. A drop in the relative scatter strength as well as the size of the xylem could indicate low water conditions or disease. For smaller plants like tomatoes the entire stalk transports the water. For healthier plants this signal level would be higher than plants not receiving as much water thought the trunk.

In other embodiments, algorithms may be used to track trunk and branch water content. In some embodiments, the algorithm may segment and detect the branches and the trunk system of the plant. The algorithm may then examine the sides of the trunk and determine the brightness of the edge to figure out the water content compared to the center part of the trunk. In some embodiments, the algorithm and scanner may work to track consistency around the circumference xylem of the trunk with respect to the water content. Since the center of the trunk image may have a thinner cross section of the xylem than at the edges of the image where the depth of the xylem is deeper due to the curvature of the trunk, the edges may be brighter in signal return in accordance with some embodiments of the invention. This would indicate the moisture level of the trunk. By having a reference trunk images with and without moisture, comparisons can be made to determine the health of the trunk.

Figure 8:
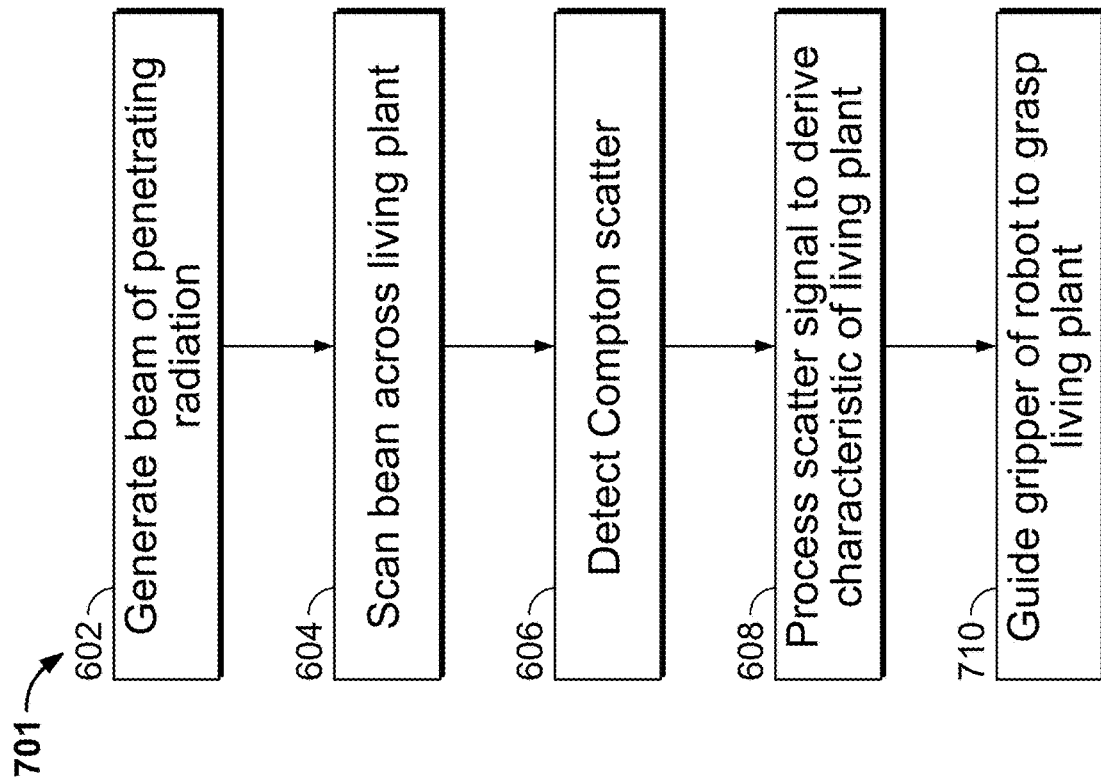
FIG. 8 shows a second flow chart depicting steps of a method for guiding the motion of a robot, in accordance with an embodiment of the present specification.

FIG. 8 depicts a second flow chart 701, with steps of a method for guiding the motion of a robot, in accordance with an embodiment of the present invention. It is a flowchart of a process that parallels that shown in FIG. 3, except that in this case the method uses the processed scatter signal to guide the gripper of the robot to grasp the living plant 710. A beam of penetrating radiation is generated (602) and scanned (604) across a living plant. Compton scatter from the living plant is detected (606) and the resultant scatter signal is processed (608) to derive characteristics of the living plant and, in possible combination with inputs derived from other sensing modalities, is used to guide a gripper of a robot for grasping the plant or a portion thereof.

FIG. 11 provides a table listing exemplary types of specialty crops where backscatter imaging may be applied. The plant height and width are used to estimate the required imaging conditions. The referenced power is the power dissipated in the source, i.e., the product of the electron current to the target (mA) times the potential of the target (kV).

Apple or citrus trees have fruit that can either grow as a single fruit or in a cluster of two or more fruit in a small area. Usually clustering causes inaccurate counting and worst case damages the fruit so they cannot be sold at maturity. In early stages using the backscatter technology, in some embodiments, the growers can accurately locate these clusters and prune or cull them so mature fruits can be harvested. In some embodiments, the exact location can be pinpointed by taking two orthogonal scans of the tree using two synchronized backscatter sources in a stereoscopic mode. In order to use two orthogonal sources and get proper imaging, according to some embodiments, the source scanning is interlaced so when one source is emitting X-rays the other is not emitting. X-ray source interlacing technology is described, for example, in U.S. Pat. No. 7,400,701 ("Backscatter Inspection Portal," to Cason), which is incorporated herein by reference. Each scan line, in some embodiments, creates one image line using a pencil beam source. To produce the scanning pencil beam a precollimator and chopper wheel is used in certain embodiments. Each chopper wheel has multiple slits called spokes and each spoke creates a line of image data, according to certain embodiments. With image processing this allows each system to gather time and spatially synched data for each tree on each source's data. This allows for a more accurate location of the fruit and also allows the system to indicate to the operator, through the user interface and database, where that cluster resides. A robotic picking system can be told exactly where the cluster is and a mechanical picking arm may then cull the non-desired fruit via a closed loop control system in certain embodiments.

For fruit that grows in clusters like grapes, the backscatter system can obtain volume information to allow the grower to determine the volume of the crop versus just the individual fruit count in certain embodiments. This information may assist the grower in knowing the crop yield and better plan for picking, packaging and set the market price.

The backscatter image created by the scanning system, according to certain embodiments, comes back with proportionate fruit size to the signal intensity and size of the fruit image on the display. Through image processing the geometric shape and size can be determined and from this the volume, assuming the fruit is symmetrical. The software, in certain embodiments, may also keep track of the accumulative total for the specific plant, crop location and metrics from year to year.

When the fruit is mature it contains significant water to allow for a strong scatter signal to the scanning system. In the image, the scattered signal shows up as bright orbs. The tree limbs show up dimmer and the canopy return is an inconsequential signal return. Using image processing, the trunk and branches can be segmented out so just the fruit remains. From this image the fruit size, volume and counts can be gathered and stored for reporting the statistics to the grower.

To detect and locate fruit in some embodiments, image processing is required. In certain embodiments, an algorithm may receive images of immature fruit to determine the fruit health and clustering of fruit by using various methods of segmentation to remove branches and foliage. Algorithms, such as cell mapping algorithms can be used to track and segment out the fruit. In some embodiments, the algorithm may focus on the bright circular orbs which are the fruit. The sizes may be monitored for roundness and determine the size to make sure the fruit are within 20% of each other. The algorithm may also note which fruits and locations of the fruit that are in clusters. The algorithm may further report on all issues, such as fruit out of size requirements, misshaped fruit and clustering fruit.

In some embodiments, algorithms may also be used for canopy detection. The canopy detection algorithm, in some embodiments, will use a dual energy method to pull out the canopy from the other parts of the plant. The leaf return level (fluid content), size and shape will be determined along with the density of the canopy. Furthermore, in some embodiments, visual camera can be used to aid in the leaf size, shape and color.

Embodiments of the invention can also be used for robotic guidance 710 (shown in FIG. 8). This may include initial target mapping in 2D or 3D, closed loop feedback guidance, and robotic harvesting. Closed loop feedback guidance may include oscillating beam guidance and image guidance.

To date, two key challenges in robotic harvesting of specialty crops include guidance as well as damage free gripping of the targeted crop. Visual methods of guidance are ineffective due to the visual clutter generated by plant foliage. Visual targeting is especially challenging for crops with the same coloring as the background foliage. Because specialty crops are sold direct to customers, robotic harvesting cannot bruise or damage the fruit. Methods such as shaking trees have been used in the past, but lead to bruising. Optical methods to image the crop for manipulator control are limited by obstructions from foliage.

In embodiments of the invention, backscatter imaging is used to improve both guidance as well as manipulator control. First, an initial 2D image can be generated of the full plant to generate a target map for harvesting. In certain embodiments, a 3D map of the crop can be generated using imaging from multiple views in a manner similar to tomography. Utilizing the 2D or 3D coordinates for the crop on each plant, the system can plan a trajectory for efficiently movement to harvest the crop. Next, in certain embodiments of the invention, a closed loop feedback system can be used to generate rapid guidance to the targeted crop. Finally, a backscatter imaging system can be used to guide an end-effector to grip the fruit for harvest. Embodiments of the invention using backscatter signal for trajectory planning and final guidance would not be distorted by clutter generated by foliage. Data analysis for the backscatter image may be simplified in comparison with analysis of visual images. In addition, embodiments of the invention may be immune to changes in the environment, and may function in day or night lighting, variable temperature conditions, fog, or rain. Backscatter signal generated by moisture on the foliage may increase the uniform background of scatter from the foliage, but would not prevent the generation of a backscatter image.

Embodiments of the invention can be used for initial target mapping, specifically 2D or 3D position detection. Typical crops such as apples, oranges, strawberries for example occur with isolated fruits. As a result, they behave as single isolated point emitters for a backscatter signal. In this case, a 3D map of the crop can be generated prior to or during harvesting by the use of a number of backscatter imaging taken at various perspectives with relation to the plant, in accordance with certain embodiments of the invention. The 3D map can be generated by mounting two or more scanners on a vehicle enabled with a tracking system as previously described. The spatial coordinates of the crop of an individual plant or tree can then be used to generate a targeting map for robotic harvest.

The initial image data can be used to avoid branches, in accordance with certain embodiments. The vehicle can also incorporate a means for robotic manipulation of an end effector appropriate for harvesting the crop. A customized end effector could be tailored to the shape and size each crop requiring harvest. Embodiments of the invention, optionally, could include two or more backscatter imaging systems which are mounted at different angles relative to the crop. In certain embodiments of the invention, the backscatter imaging systems may be at varying angles, with at least 45 degrees between views and preferably 90 degrees in order to generate a 3D perspective of the crop.

Embodiments of the invention may also provide closed loop feedback guidance, including image guidance. In certain embodiments, following the generation of target coordinates, the system may use a closed loop feedback control system using one of two methods in order to position the manipulator in proximity to the fruit. One method employed by some embodiments of the invention may utilize rapid 2D or 3D imaging of the crop. The robotic harvesting system could be used to create a rapid localized backscatter image of the plant from one of multiple views.

Embodiments of the invention may also use oscillating beam guidance to move the robotic manipulator in proximity to the target using 3D position information. In some embodiments, as the arm approaches the target it may be guided in a closed loop feedback system. For rapid and accurate final guidance to a specific selected target, the time required to produce and process an image will be important. The robotic arm may be equipped with an X-ray source with pencil beam collimation or fan beam collimation.

The output beam will strike the target and produce a back-scatter signal in some embodiments of the invention. The position of the beam may be oscillated in a motion shown by changing the position or angle of the collimation to produce a time varying back-scatter signal. The position may be varied in one or more dimensions. The amplitude of the signal generated by the oscillating input beam correlates to the position of the beam on the target.

In some embodiments, in order to maintain the best approach to the target, the backscatter signal amplitude is actively maintained at a maximum by serving the position and orientation of conveyance 108 (shown in FIG. 2) as it approaches the target. In some embodiments, by maintaining the signal at a maximum amplitude, the robotic manipulator will approach to the target in a direct line. Image based as well as stationary pencil beam data can be used in conjunction based on the speed of the robotic motion and proximity to the target. As the picking arm moved in close to the fruit to be picked it could continuously update the positioning and feed the arm with new control data on the arms positon and fruits positon, in accordance with certain embodiments of the invention.

In some embodiments, when the arm is in close proximity to the fruit (almost touching) the backscatter image can be used to control the gripper motion. Based on the shape, size and orientation of the fruit in the backscatter data, it may open the picking mechanism to surround the fruit. Once the fruit is picked the robot may gently place the fruit in a container as to not damage the fruit. A sensing mechanism, such as sound or IR range sensors, may tell the robot how deep the fruit is in the container so it can be gently place in without dropping it and hitting other fruit.

Utilizing the 3D coordinate mapping in some embodiments, the system may be adapted to selectively harvest only the side of the plant closest to robot, in order to prevent plant damage caused by the manipulator reaching through the plant. That is achieved based on determining the position of a central stem of the plant, and harvesting only product that is disposed a distance relative to the robot that is shorter than the distance to the central stem at each specific elevation. Plants may advantageously be harvested sequentially down the row without interruption using the 3D coordinate mapping. The system may advantageously be capable of continuous operation, scanning 24 hours a day 7 days a week, advantageously requiring only minor operator intervention or supervision. Cameras may advantageously be located on the robot to allow operators to monitor progress and intervene if issues are encountered.

FIG. 9 shows a fan beam scanning apparatus using fan beam illumination, designated generally by numeral 901, for accelerated acquisition of yield estimates and other crop characterization. In some embodiments of the present invention, backscatter imaging may be limited in speed by the flux emitted from the pencil beam collimation. In certain embodiments, to increase the flux illuminating the object, a back-scatter imaging system may advantageously use fan-beam illumination. In some embodiments, scanning apparatus 901 may estimate the total volume of crop 112 in the field. In certain embodiments, the illumination fan beam 910 is advantageously positioned in a vertical orientation and scanned across an object under inspection. The total X-ray backscatter from along the line of illumination (which is a cross-section of the fan beam) is detected at once and generates a scatter signal. Resulting data from the scanning may be a 1D plot of total backscatter position vs. signal, along the path of conveyance 108 in accordance with certain embodiments.

Figure 10:
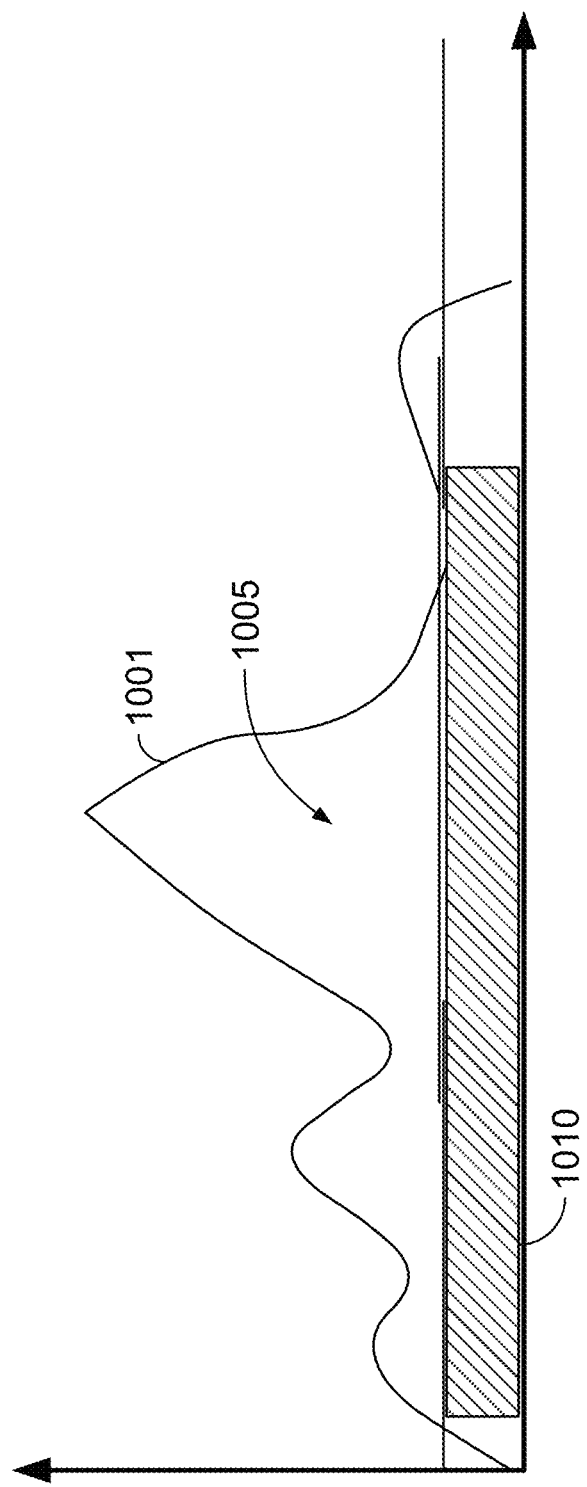
FIG. 10 shows a plot illustrating the use of volume information from the scanning process to quantify fruit, in accordance with an embodiment of the present specification.

FIG. 10 shows a plot 1001 illustrating the use of volume information from the scanning process to quantify fruit. Volume information may be inferred from the 1D plot 1001 of backscatter signal vs. position through integrating the area 1005 under the curve 1001 and comparing it with a tunable threshold 1010 for detecting fruit 112 (shown in FIG. 2). The volume derived from area 1005 may correlate with the total mass of fruit in accordance with certain embodiments. The tunable threshold 1010 may, in certain embodiments, advantageously reject object such as trunk, canopy, and branch signal.

In embodiments, the present specification provides a method for quantitative measurement of the weight of a portion of a crop, such as hanging fruit, positioned on at least one plant, branch, and/or vine. While the embodiments described herein are with reference to a hanging fruit, it should be noted that the present specification is not limited to such embodiments and that any crop member may be weighed using the methods provided herein. In embodiments, a backscatter X-ray scanning system, such as described above may be used to scan plants, or any portion thereof, such as branches and/or vines, to obtain scan images, which may be analyzed to determine a weight of the hanging fruits in a field of the plants, branches, and/or vines. In various embodiments, the backscatter signal generated from a hanging fruit is proportional to the mass of the fruit as well as the distance of the fruit from the scanning system. The backscatter signal generated by a fruit illuminated by incident X-rays, is approximately proportional to the square of the distance of the fruit from the scanning system. In an embodiment, the backscatter signal intensity is integrated across the fruit being imaged as a measurement of a total mass of the fruit. In embodiments, weights of fruit such as, but not limited to grapes, berries, citrus fruits, apples, melons, and tomatoes may be estimated by using the method of the present specification. In embodiments, the method of the present specification may be used to determine the weights of any trellised fruits or vine fruits, which may be scanned on two sides. In embodiments, the method of the present specification may be used to determine the weights of any non-trellised fruits or vine fruits, which may be scanned on two sides.

The description below interchangeably describes both methods for gathering crop data and image processing tasks that are used to analyze the data, said image processing tasks being executed by a controller coupled with one or more X-ray scanners which are used for gathering the crop data by irradiating said crop with X-rays from multiple directions and obtaining scan images.

In various embodiments, a controller is a computing device including an input/output unit, at least one communications interface and a system memory. The system memory includes at least one random access memory (RAM) and at least one read-only memory (ROM). These elements are in communication with a central processing unit (CPU) to enable operation of the controller. In various embodiments, the controller may be a conventional stand-alone computer or alternatively, the functions of the controller may be distributed across a network of multiple computer systems and architectures.

In some embodiments, execution of a plurality of sequences of programmatic instructions for quantitative measurement of the weight of a portion of a crop enable or cause the CPU of the controller to perform various functions and processes such as, for example, performing tomographic image reconstruction for display on a screen. In alternate embodiments, hard-wired circuitry may be used in place of, or in combination with, software instructions for implementation of the processes of systems and methods described in this application. Thus, the systems and methods described are not limited to any specific combination of hardware and software.

In an embodiment, the present specification provides a method for performing dual-view data acquisition by scanning the plants, branches, vines and/or fruits from two different sides of the crop using two X-ray scanners simultaneously. In another embodiment, dual view data acquisition may be performed by scanning the fruits on two different sides using a single X-ray scanner which is operated to acquire multiple scans. More specifically, X-ray scanners are positioned outside of a fruiting region of a field (areas of the crop where fruit is growing or expected to grow), on opposite sides of a row of plants. In an embodiment, scan data from each view point (X-ray scanner location) is registered by using position sensors or supplementary camera views. Since the backscatter signal generated from a hanging fruit is proportional to the mass of the fruit as well as the distance of the fruit from the scanning system, it is useful to know the position of the X-ray scanner at any given time. The orientation and position of the scanner may be recorded to preserve the relative illumination angle and position of the X-ray source with respect to the fruit. In embodiments, once the scan images of the fruits are collected, said images may be analyzed by using a distance normalization process at a pixel or feature level. In an embodiment, identical pixels from two images may be compared and be used to correct for variations in distance. In another embodiment, where feature level distance correction is performed, the scanned fruits may be integrated with intensity and then distance corrected.

Figure 12A:
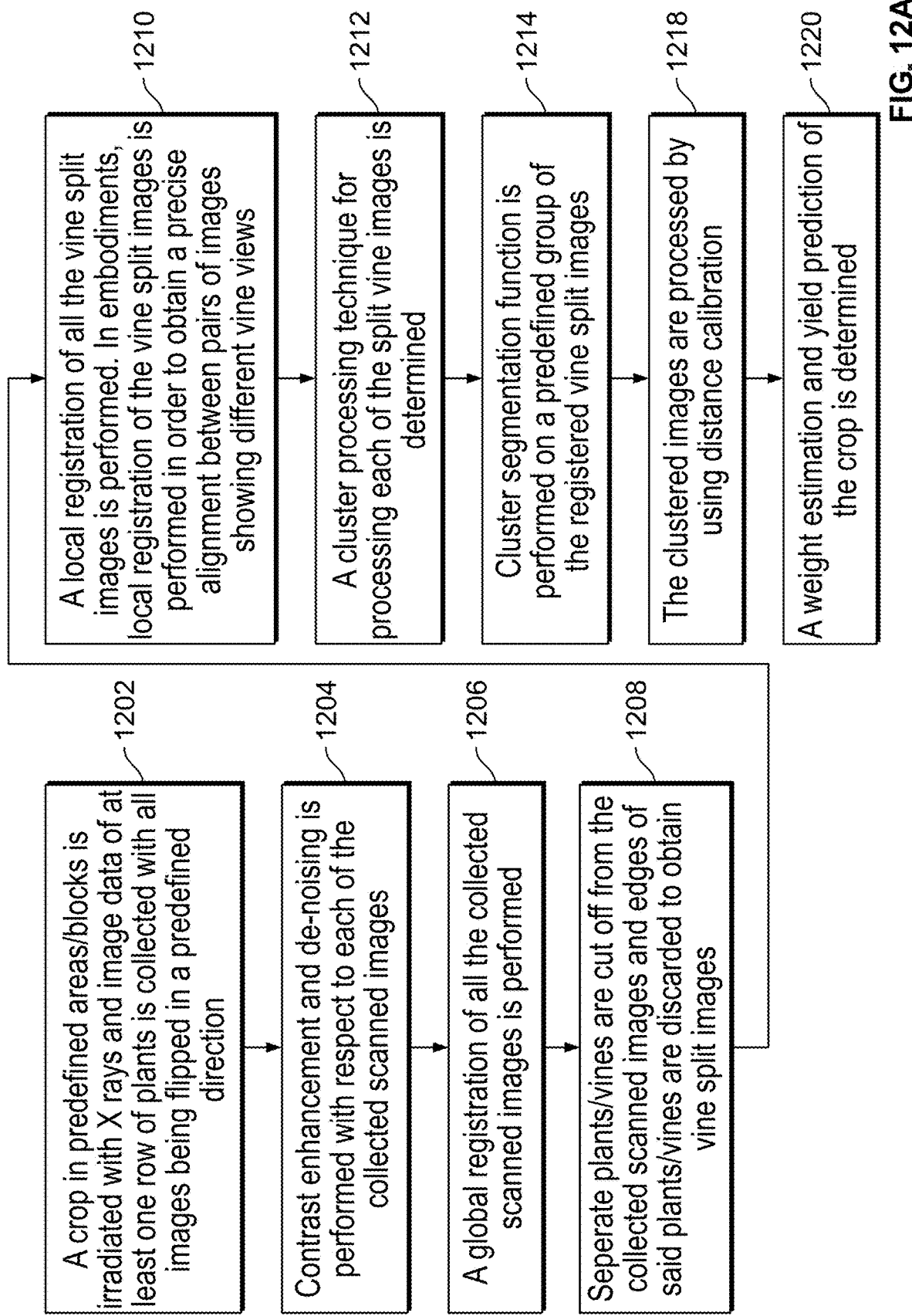
FIG. 12A is a flowchart illustrating a method for estimating weight and predicting the yield of a crop, in accordance with an embodiment of the present specification.

In various embodiments, the scanned fruit data is analyzed by using image segmentation for estimating weight and predicting yield of the fruit in a field. FIG. 12A is a flowchart illustrating a method for estimating weight and predicting the yield of a crop, in accordance with an embodiment of the present specification. At step 1202, a crop in predefined areas/blocks is irradiated with X-rays and image data of at least one row of plants is collected with all images being flipped in a predefined direction. In an embodiment, the crop is a fruit crop comprising vines with fruit growing on said vines, such as grapes. FIG. 12A will be described with reference to subsequent figures. In an embodiment, data, such as but not limited to image data, GPS coordinate data, scanning speed data, and/or tilt/inclinometer data is stored in a raw data file.

Figure 12B:
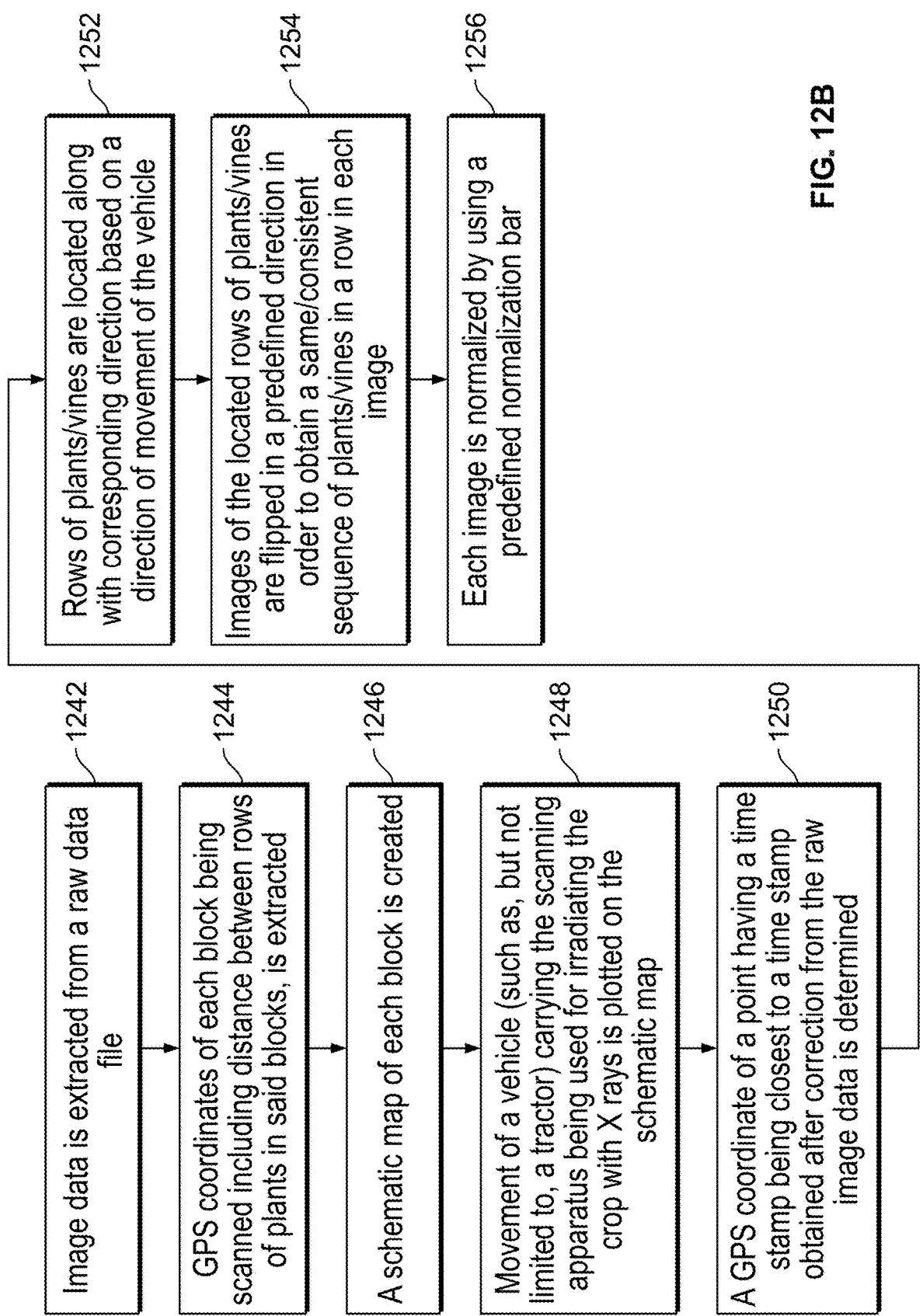
FIG. 12B is a flowchart illustrating the steps of collecting image data of a row of plants, in accordance with an embodiment of the present specification.

FIG. 12B is a flowchart illustrating the steps of collecting image data for a row of plants, in accordance with an embodiment of the present specification. At step 1242, image data is extracted from a raw data file. At step 1244, GPS coordinates of each block being scanned including a distance between rows of plants in said blocks, is extracted from the raw data file. At step 1246 a schematic map of each block is created. At step 1248 the movement or conveyance of a vehicle (such as, but not limited to, a tractor) carrying the scanning apparatus being used for irradiating the crop with X-rays is plotted on the schematic map. At step 1250, a GPS coordinate of a point having a time stamp that is closest to an image time stamp obtained after distance correction from the raw image data is determined. Mores specifically, a GPS coordinate of a point on the schematic map is determined by correlating at least one timestamp of one or more GPS coordinates with at least one timestamp of when points on the schematic map were captured.

In embodiments, once the scan images of the fruits are collected, said images may be analyzed by using distance normalization process at a pixel or feature level. In an embodiment, identical pixels from two images may be compared and be used to correct for variations in distance. In another embodiment, where feature level distance correction is performed, the scanned fruits may be integrated with intensity and then distance corrected. In embodiments, feature level distance correction allows for changes for matching both the registration and the magnification of the individual features of said images; whereas pixel level distance correction does not allow for changes in perspective, registration, or magnification of said images. In an embodiment, for performing a feature level distance correction, predefined features are segmented from the images, and the segmented features are matched with respect to drive directions, registration, and magnification of said images, thereby resulting in a pixel by pixel distance correction of said images.

Figure 12C:
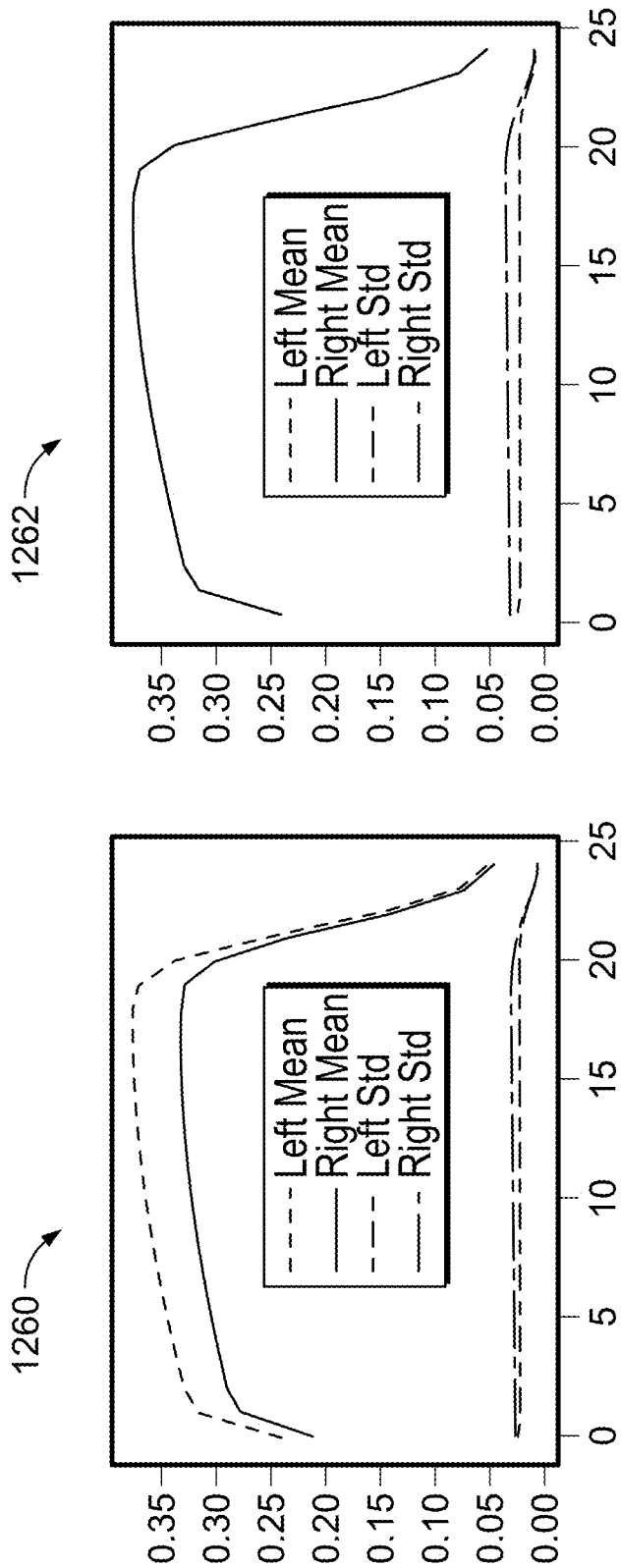
FIG. 12C illustrates plots of the image data before and after normalization, in accordance with an embodiment of the present specification.
Figure 21B:
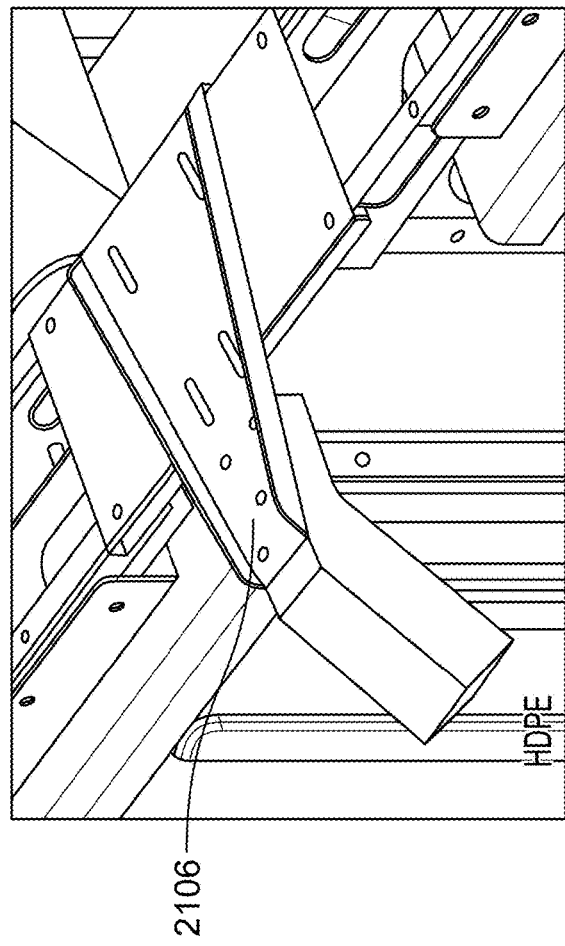
FIG. 21B illustrates a contrast block employed in the scanning system of FIG. 22A, in accordance with an embodiment of the present specification.
Figure 21D:
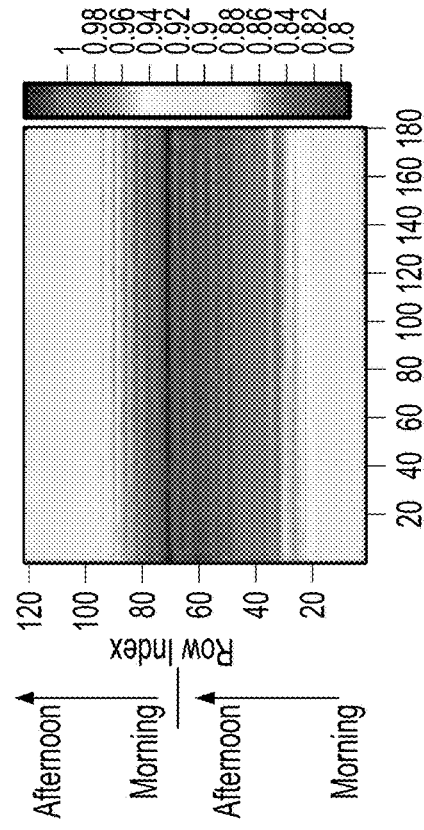
FIG. 21D illustrates a graph showing contrast block variation across field with respect to different times of the day, in accordance with an embodiment of the present specification.
Figure 21A:
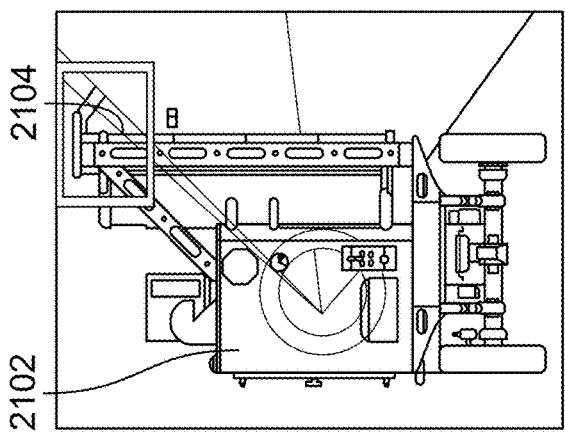
FIG. 21A illustrates a scanning system for scanning crops for predicting the weight of hanging fruit, in accordance with an embodiment of the present specification.
Figure 21C:
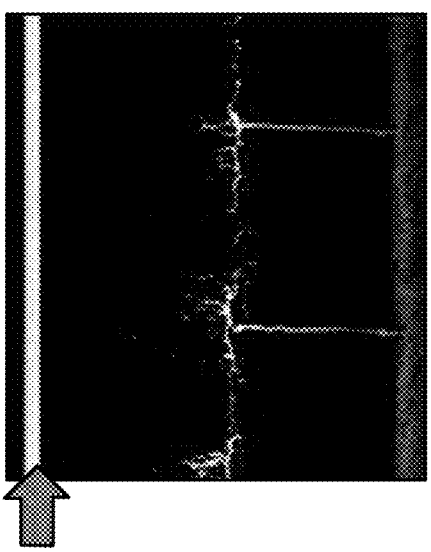
FIG. 21C illustrates a scan image obtained by using a contrast block, in accordance with an embodiment of the present specification.

At step 1252, rows of plants/vines are located along with a corresponding direction based on a direction of movement of the vehicle. At step 1254, images of the located rows of plants/branches/vines are flipped in a predefined direction in order to obtain a same/consistent sequence of plants/branches/vines in a row in each image. At step 1256, each image is normalized by using a predefined normalization bar. In an embodiment, a piece of HDPE plastic (plastic member) is located at a top of the field of view of the scanner, such that the X-ray scanning beam strikes the plastic piece and yields a signal which is used for calibration/normalization of each image. In embodiments, the HDPE plastic member may be a contrast block as shown in FIGS. 21A-21B and described below. FIG. 12C illustrates plots of the image data before and after normalization, in accordance with an embodiment of the present specification. Plots 1260 and 1262 show measured intensity data of the scan image corresponding to each pixel row of the image before and after normalization, wherein said normalization is carried out to correct for any changes that may occur with respect to the source intensity or detector response of the scanner.

Referring back to FIG. 12A, at step 1204 contrast enhancement and de-noising is performed with respect to each of the collected scan images in order to enable better registration and segmentation. In embodiments, the images are processed to enhance the image contrast by using any of the commonly known contrast enhancement techniques. In an embodiment, contrast enhancement of the images is carried out by using one or more of known image processing techniques, such as, but not limited to histogram equalization wherein the contrast of images is enhanced by transforming the values in an intensity image so that the histogram of the output image approximately matches a specified histogram. In another embodiment, a contrast-limited adaptive histogram equalization technique may be employed wherein contrast of small data regions (tiles) of an image is enhanced so that the histogram of each output region approximately matches the specified histogram. The contrast enhancement can be limited in order to avoid amplifying the noise which might be present in the images. In embodiments, the specified histogram is a final data histogram of all the pixels in the full image.

Figure 13A:
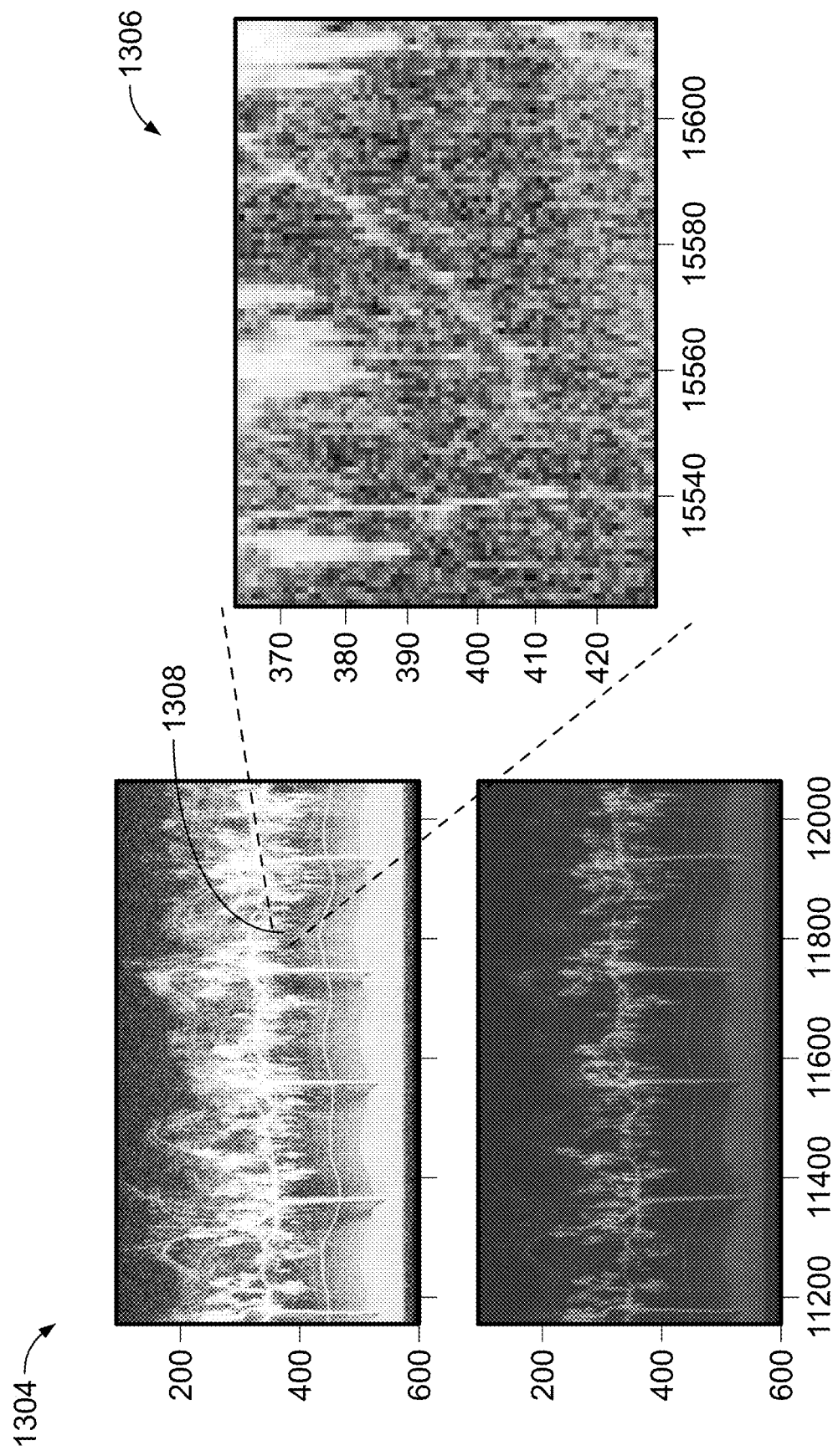
FIG. 13A is a scan image before and after contrast enhancement, in accordance with an embodiment of the present specification.

FIG. 13A illustrates a scan image before and after contrast enhancement, in accordance with an embodiment of the present specification. A contrast enhanced image 1304 is obtained upon processing the scan image 1302 with contrast enhancement algorithms. As can be seen from exploded image 1306 of a portion 1308 of the image 1304, noise in the image is also enhanced along with an enhancement in the contrast level. In embodiments, the noise in the contrast enhanced images is eliminated by removing all image pixels lying below a predefined threshold value. In an embodiment, all image pixels having less than three neighboring pixels that are greater than the threshold value are also removed. In embodiments the de-noising threshold value is selected to include relevant features in the image such as, but not limited to the leaves, clusters, and cordon.

Figure 13B:
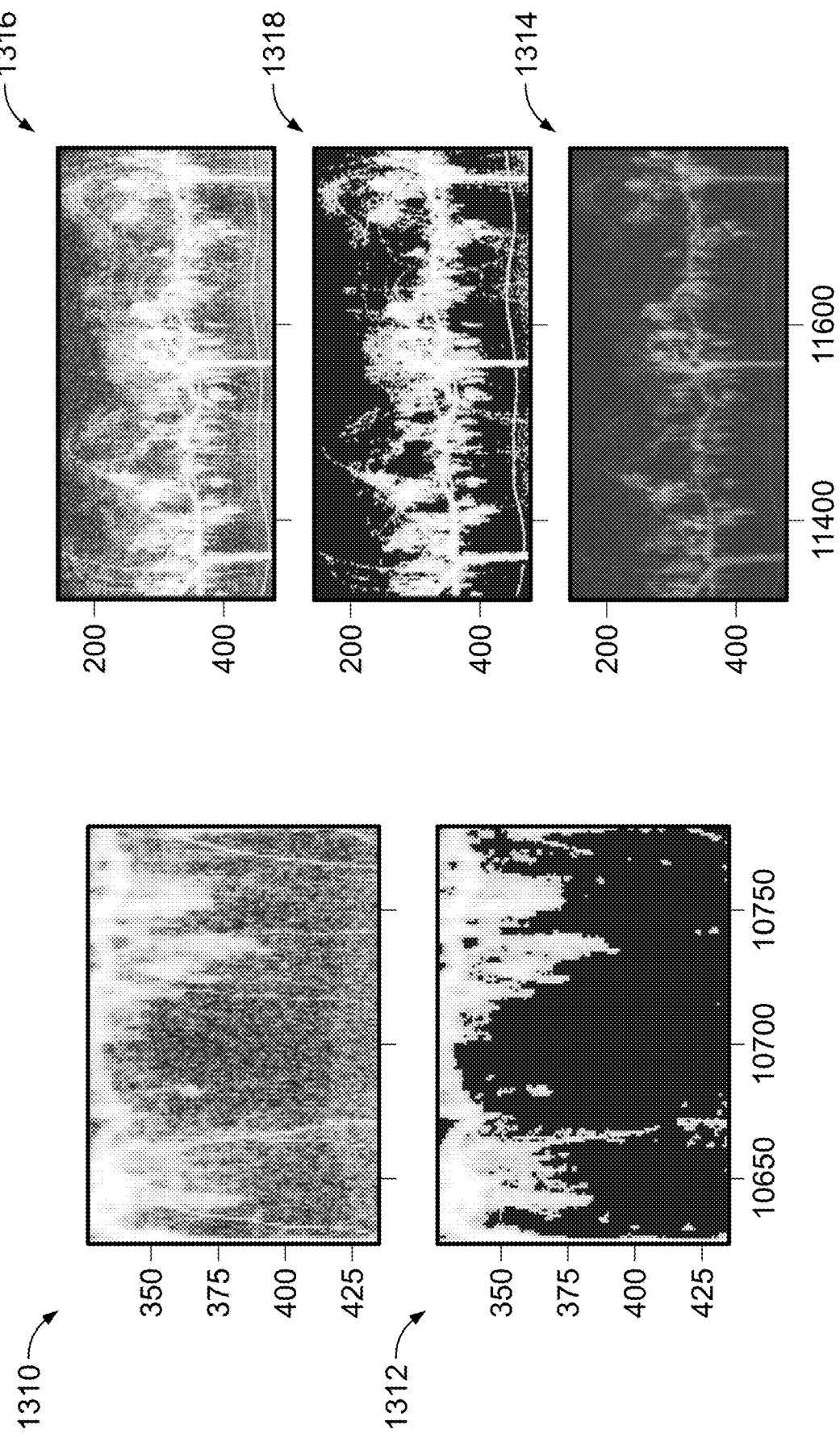
FIG. 13B is a contrast enhanced image before and after de-noising, in accordance with an embodiment of the present specification.

FIG. 13B illustrates a contrast enhanced image before and after de-noising, in accordance with an embodiment of the present specification. Image 1310 is a contrast enhanced image which is de-noised to obtain image 1312. Also shown in FIG. 13B is an image 1314 before contrast enhancement and de-noising. After applying contrast enhancement techniques on image 1314, contrast enhanced image 1316 is obtained, which when de-noised results in image 1318.

Figure 14A:
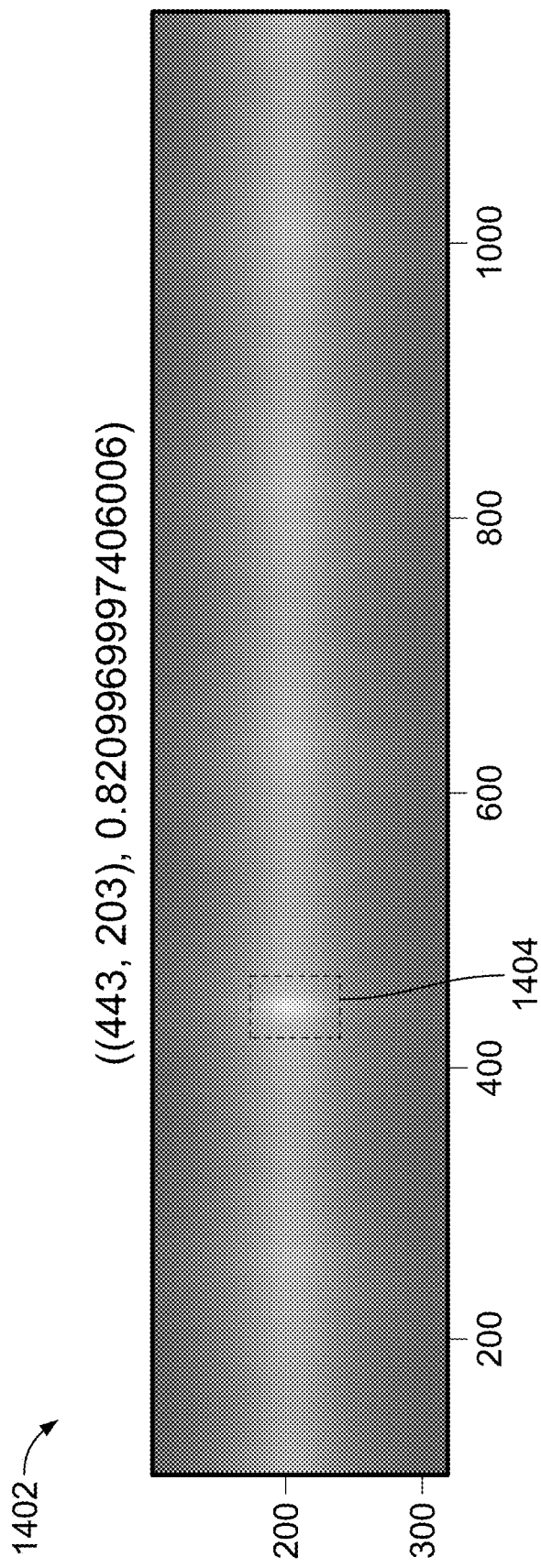
FIG. 14A is an image upon which global registration is performed.

Referring back to FIG. 12A, at step 1206, a global registration of all the collected scan images is performed. In an embodiment, global registration of each image is performed by selecting a predefined section from a first image and finding an optimal correlation of the section in a second image. In an embodiment, the optimal correlation is the location which provides a desired registration between the two images, and may be obtained by using a technique such as, but not limited to, least square fitting. In an embodiment, a horizontal scaling of the images is corrected during the global registration process. FIG. 14A illustrates an image upon which global registration has been performed. In an embodiment, a left section of the image 1402 was selected and correlated with a second image which was obtained by flipping the image 1402. Point or area 1404 represents a point or area at which the two images have the best or optimal overlap. The figure shows the quality of the registration of the two images with the application of horizontal and vertical shifting.

Figure 14B:
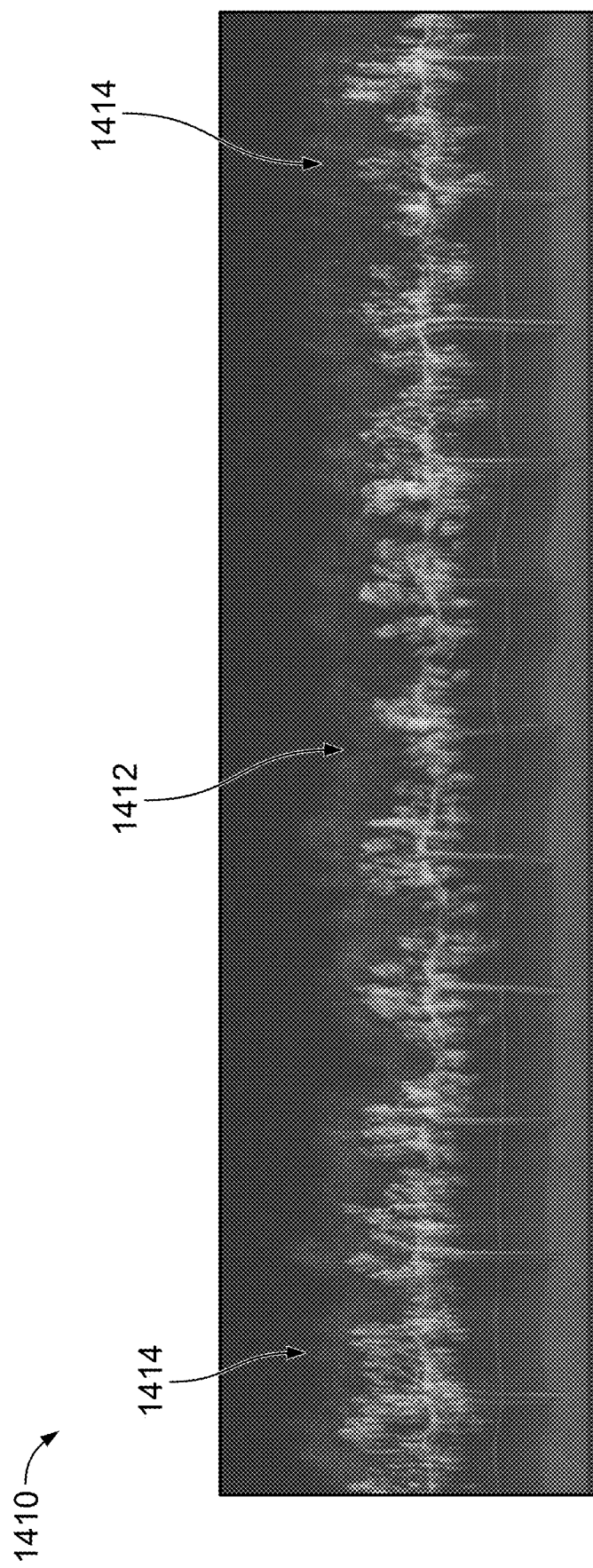
FIG. 14B illustrates an image showing global registration results, in accordance with an embodiment of the present specification.

In some embodiments, the step of global registration 1106 is not performed. FIG. 14B illustrates an image 1410 showing global registration results, in accordance with an embodiment of the present specification. In some embodiments, global registration provides desirable results in the middle region 1412 of an image 1410, however, the edges/sides 1414 of said image show accumulation of offset data. Hence, in some embodiments, a process of local registration is performed. In embodiments, global registration is performed on an entire row of images (comprising multiple plants, branches, and/or vines) at the same time; whereas local registration is performed on each plant, branch or vine one at a time after segmenting. In embodiments, global registration is performed on an entire row of images (comprising multiple vines) at the same time; whereas local registration is performed on each vine one at a time after segmenting. Hence, local registration is more accurate since it allows for changes in speed, as is shown in FIG. 14B.

Referring back to FIG. 12A, at step 1208 separate plants/branches/vines are cut off from the collected scan images and edges of said plants/branches/vines are discarded to obtain split images. In embodiments, such as in the area of viticulture, for example, splitting is performed as data is collected for ground truth vines individually. In embodiments, individual plants/vines/branches from the at least one row of plants are separated by using features such as stems or trunks. For example, vines may be identified by the presence of the trunk of each plant. In embodiments, false positives may be eliminated by enforcing a minimum distance between vines. In embodiments, known methods of plant/branch/vine splitting such as, but not limited to, identifying a vertical column of pixels and applying various available filters for the same does not produce desired results. This is due to a plurality of reasons such as: poles and stakes as well as long overhanging clusters in images being identified as stems, slanting stems in images not being identified, missing vines in images not being identified every time and large variations in ground topology and vertical magnification in the images. In various embodiments, manual identification of starting point of plants/branches/vines in images, extensive manual checking and making corrections when a distance between plants, such as, but not limited to vines was greater or smaller than predefined values, produces desired results. In an embodiment, a benchmark for a desired result is the actual distance between the plants/branches/vines, which is known from a time of crop plantation (and, in an example, vine plantation). Hence, the measured or determined distance between the plants/branches/vines cannot be less than the actual distance at the time of crop plantation. Thus, in the case of viticulture, the measured or determined distance between the vines cannot be less than the actual distance at the time of vine plantation. FIG. 15A illustrates a successful vine split image 1510, in accordance with an embodiment of the present specification. FIG. 15B illustrates a vine split image 1520 showing false positives, in accordance with an embodiment of the present specification.

Referring back to FIG. 12A, at step 1210, a local registration of all the split images is performed (and, in an example, of the vine split images). In embodiments, local registration of the split images is performed in order to obtain a precise alignment between pairs of images showing different plant views. This is achieved by enabling distance calibration using images showing opposite plant views, subtracting cordon using a corresponding image taken previously during pre-bloom season, and helping cluster segmentation using images showing plant views from earlier in the season. Said subtraction removes any intense background due to the cordon from the registered images. In various embodiments, a predefined registration algorithm (comprising steps for one or more of: image shifting and magnification) is used for said local registration of the split images in order to obtain results without distortion.

Figure 16A:
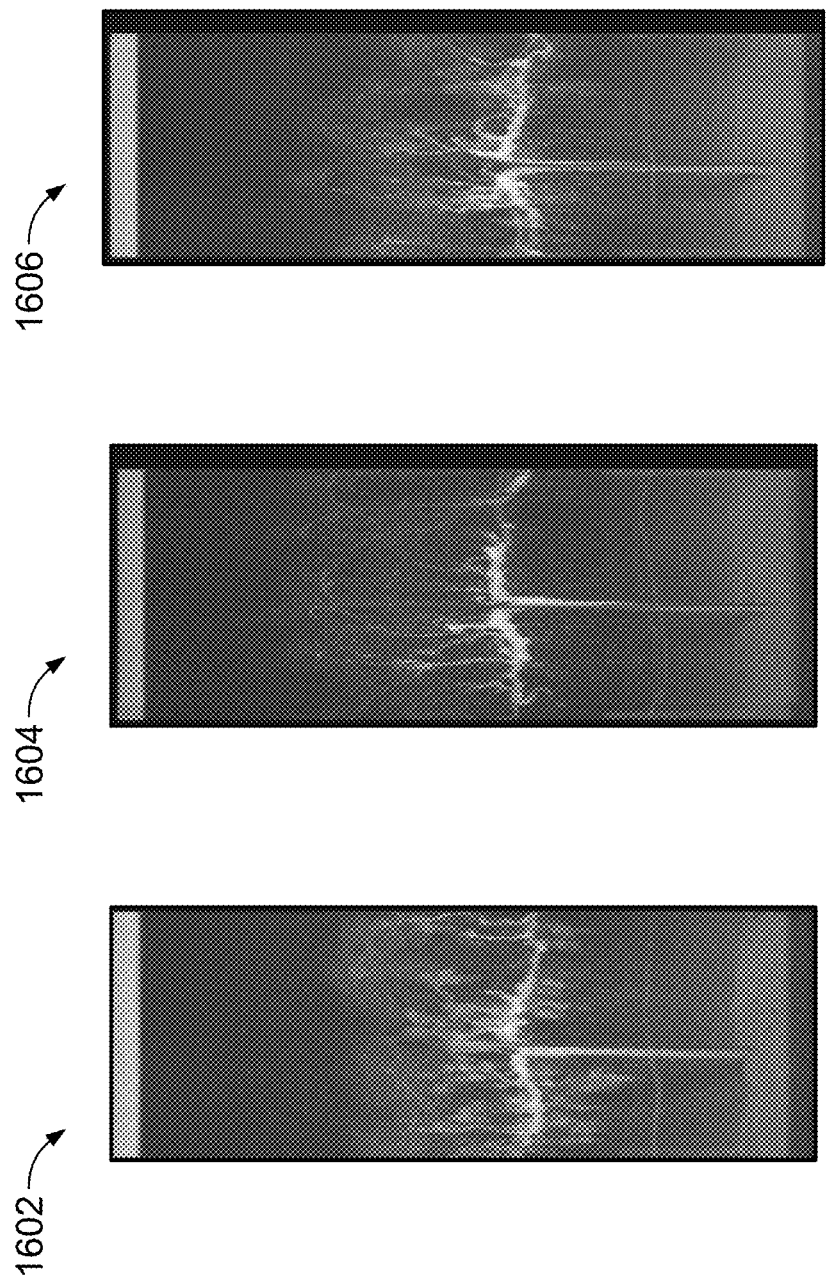
FIG. 16A illustrates split images after application local registration, in accordance with an embodiment of the present specification.

FIG. 16A illustrates split images (such as vine split images) after applying local registration, in accordance with an embodiment of the present specification. Image 1602 illustrates local registration applied on pre and post-harvest images. Image 1604 illustrates local registration applied on pre-bloom and post-harvest images. Image 1606 illustrates local registration applied on a fruit set and a post-harvest image.

Figure 16B:
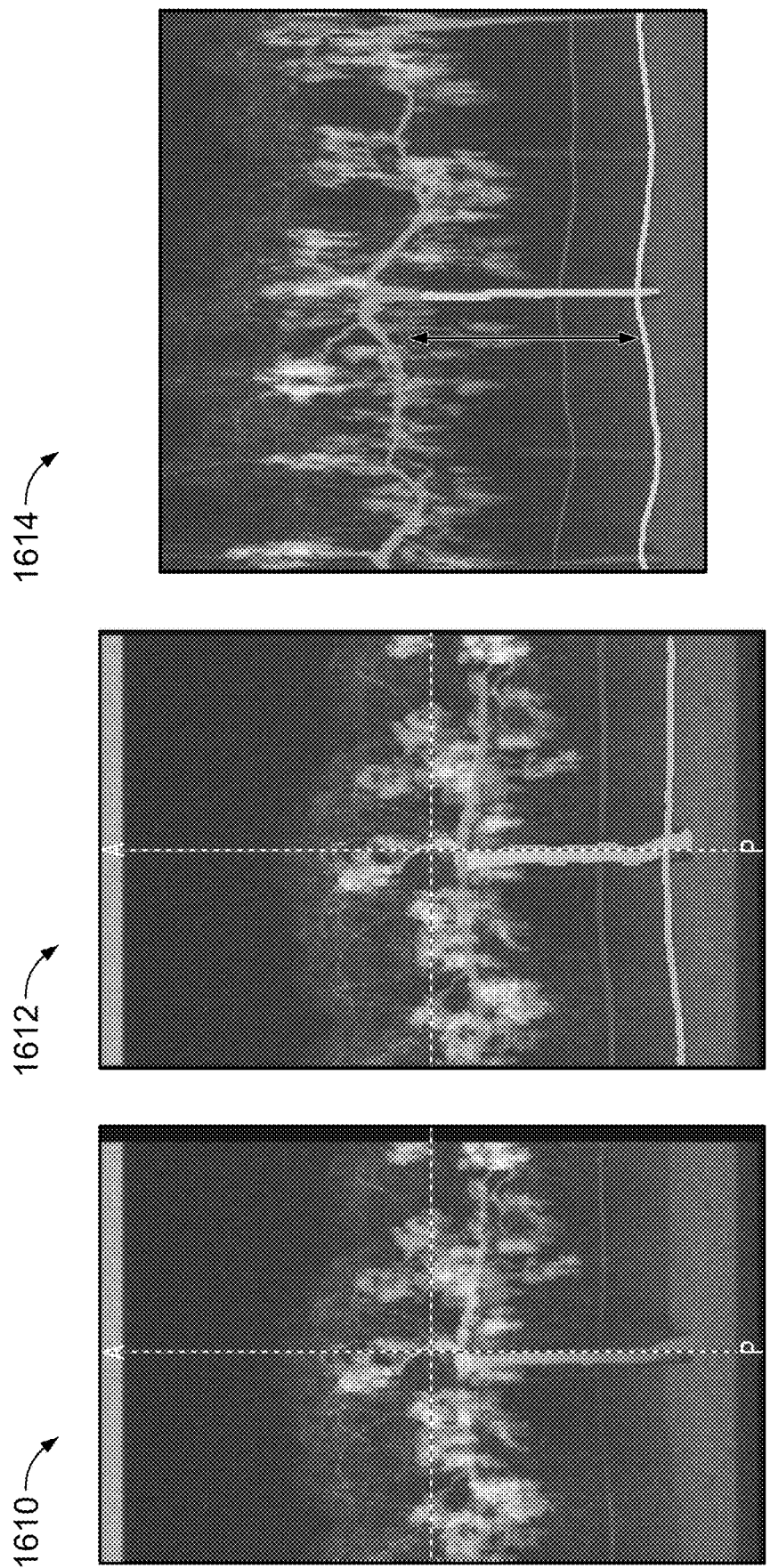
FIG. 16B illustrates coarse feature annotation on split images, in accordance with an embodiment of the present specification.

In an embodiment, instead of registering pairs of images, all images are modified such that they are uniform in order to create a uniform vertical scaling for performing data analysis, for improving efficiency of the image registration process. In an embodiment, a "Coarse Annotation" method is used, which employs manually annotating cordon, stem, ground border and water pipe and may comprise straightening cordons, aligning images horizontally using stem, aligning images vertically using a straightened cordon, and vertical scaling of images by keeping distance between cordon and ground constant. FIG. 16B illustrates coarse feature annotation on split images (such as a vine split image), in accordance with an embodiment of the present specification. Image 1610 illustrates a vine split image with a trunk identified, before application of coarse feature annotation. Image 1612 illustrates the same vine split image after application of coarse feature annotation. Image 1614 illustrates the same vine split image being registered by using coarse feature annotation, wherein a height of a cordon has been identified. FIG. 16C illustrates registration of vine split images by using coarse feature annotation, in accordance with an embodiment of the present specification. Images 1616 and 1618 demonstrate regularization of a vine which has flattened the cordon. FIG. 16D illustrates a close-up view of sides of vine split images by using coarse feature annotation, in accordance with an embodiment of the present specification. Images 1620 and 1622 illustrate a close up view of a vine cluster from a first direction/side and a second opposing direction/side respectively.

Referring back to FIG. 12A, at step 1212 a cluster processing technique for processing each of the split images is determined. At step 1214, a cluster segmentation function is performed on a predefined group of the registered split images. In an embodiment, a classical cluster segmentation function is performed on a predefined group of the registered split images. In an alternative embodiment, a deep learning cluster segmentation function is performed on a predefined group of the registered split images. In an embodiment, a classical cluster segmentation algorithm based on a set of predefined rules is used to process the predefined group of the registered split images. In embodiments, the split images are clustered in order to enable cluster-based data analysis and also to train neural networks to identify clusters during data analysis. In an embodiment, at least one cluster of plants within a predefined distance are identified and annotated. In an embodiment, at least one cluster of vines within a predefined distance are identified and annotated.

In an embodiment, when a deep learning cluster segmentation function is used, the identification and annotation is performed by a deep learning algorithm, trained to identify desired features in manually selected clusters. FIG. 17A illustrates a cluster annotated image, in accordance with an embodiment of the present specification. Image 1710 is processed using a cluster segmentation function to produce a cluster annotated image 1720. The different shadings shown in image 1720 are representative of various manual annotations.

Figure 17D:
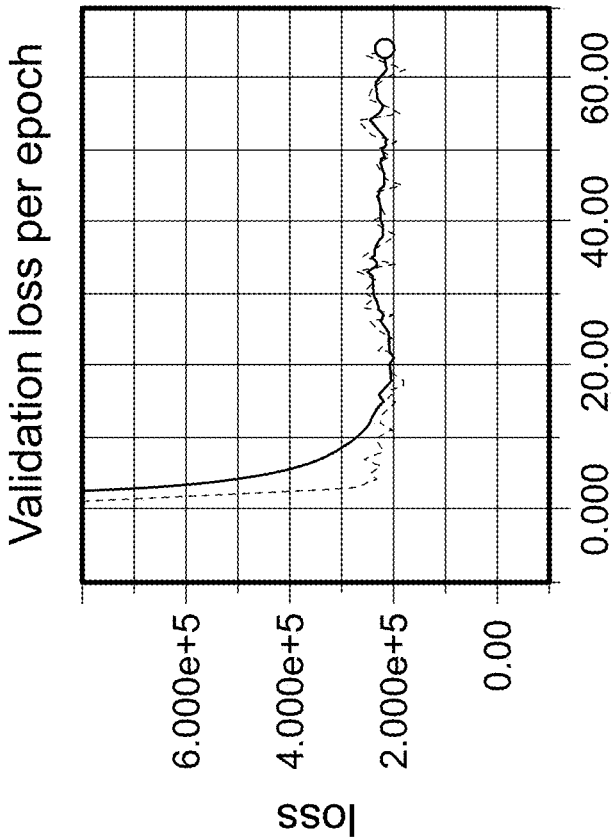
FIG. 17D illustrates a graph showing validation loss per epoch in a coarse segmentation network when training is performed on 50 pre-harvest data images having 5 validation sets.
Figure 17C:
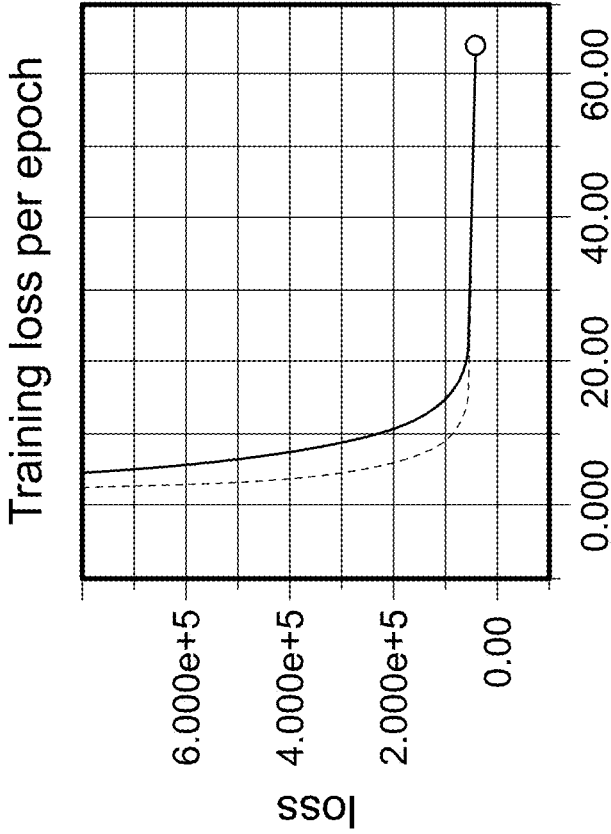
FIG. 17C illustrates a graph showing training loss per epoch in a coarse segmentation network when training is performed on 50 pre-harvest data images.

In an embodiment, the split images (such as vine split images) are processed by using a 'coarse segment analysis' method in which a coarse segment network is used to perform the coarse segment analysis of images. FIG. 17B illustrates a coarse segment network, in accordance with an embodiment of the present specification. Image 1730 is an input scan image of a vine in a field, while image 1732 depicts a desired output image comprising predefined multiclass segments. In an embodiment, examples of segmentation classes include post, cordon ground line, pipe and background. Image 1734 depicts segmentation classes applied on the image 1730. FIG. 17C illustrates a graph showing training loss per epoch in a coarse segmentation network when training is performed on 50 pre-harvest data vine images. FIG. 17D illustrates a graph showing validation loss per epoch in a coarse segmentation network when training is performed on 50 pre-harvest data vine images having 5 validation sets. In various embodiments, coarse segmentation identifies major features of a field of fruit vines such as, but not limited to: ground, trunk, cordon, and/or water pipes. The graphs depicted in FIGS. 17C and 17D demonstrate that the method of the present specification allows for identification of such features.

Referring back to FIG. 12A, at step 1218 the clustered images are processed using distance calibration. At step 1220, a weight estimation and yield prediction of the crop is determined. In an embodiment, individual pixel intensity of the clustered images is measured from a scan of the crop feature from two sides. FIG. 17E is a block diagram illustrating distance calibration being applied to images obtained by scanning an object from two opposing sides, in accordance with an embodiment of the present specification. As shown in the figure, a first X-ray system 1750 scans a crop cluster 1752 from a first side while a second X-ray system 1754 scans the crop cluster 1752 from a second opposing side. A distance of the scanning systems 1750, 1754 from a center of the crop cluster 1752 is the same and is labeled as 'L' in FIG. 17E. A distance of the first scanning system 1750 from a first side 1756 of the cluster 1752 is labeled as 'd' in the figure. After measuring individual pixel intensity of the clustered images by using the scan of the cluster 1752 from two sides, a correction is applied based on the ratio of the intensities $I_1$ measured from the first side and $I_2$ measured from the second side. In embodiments:

$$I_1 = I_0/(d/L)^2 \qquad (1)$$

$$I_2 = I_0/((2L-d)/L)^2 \qquad (2)$$

$$I_0 = (4I_1 I_2)/(\sqrt{I_1} + \sqrt{I_2})^2 \qquad (3)$$

In an embodiment, where $I_1 > I_2$, a distance correction factor 'C' is determined as:

$$C = I_0/I_1 = 4/(1+\sqrt{R})^2 \qquad (4)$$

wherein 'R' represents intensity ratio and is equal to $I_1/I_2$.

Figure 17F:
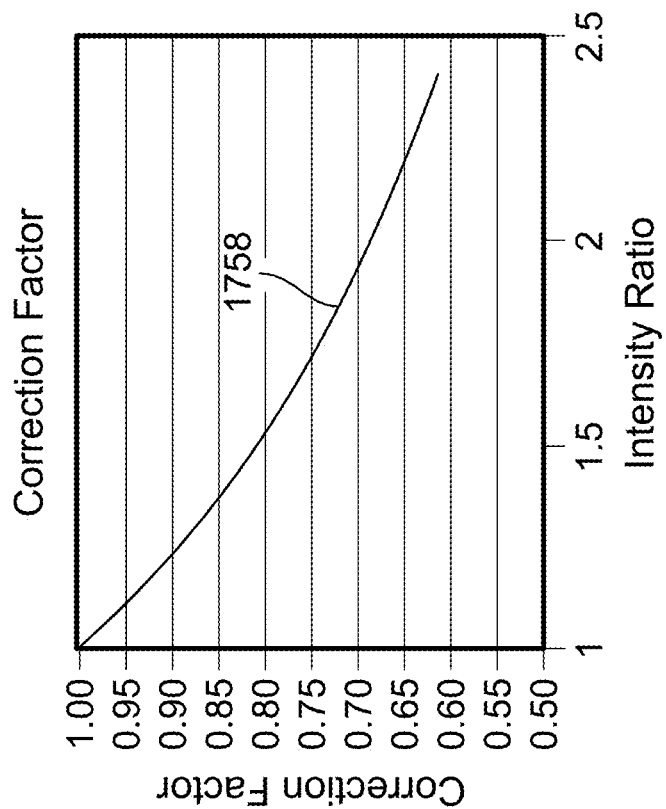
FIG. 17F illustrates a plot of the correction factor C against intensity ratio, in accordance with an embodiment of the present specification.
Figure 17E:
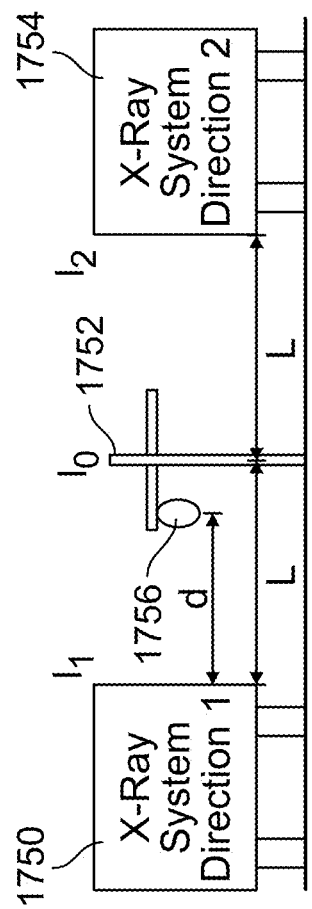
FIG. 17E is a block diagram illustrating the application of distance calibration to images obtained by scanning an object from two opposing sides, in accordance with an embodiment of the present specification.

FIG. 17F illustrates a plot of the correction factor C against intensity ratio, in accordance with an embodiment of the present specification. As can be seen in FIG. 17F, plot 1758 of the correction factor C decreases with an increase in the intensity ratio.

In an embodiment, an estimation of a weight of fruit hanging from vines in a field is achieved by determining a change in the X-ray signal backscattered by the fruit over a predetermined period of time, such as over a pre-bloom season (i.e. from late April) to a harvest season (i.e. late October) of any given year for any given crop. The time-based comparison of crop images enables crop yield prediction. Accurate measurement of the mass of fruits/vegetables growing on plants/branches/vines, which is often referred to as hanging weight, in the early season (pre-harvest) enables a prediction of the harvest yield. In various embodiments, yield estimation is performed by using the measurement of early season hanging weight and also the growth rate.

Figure 18A:
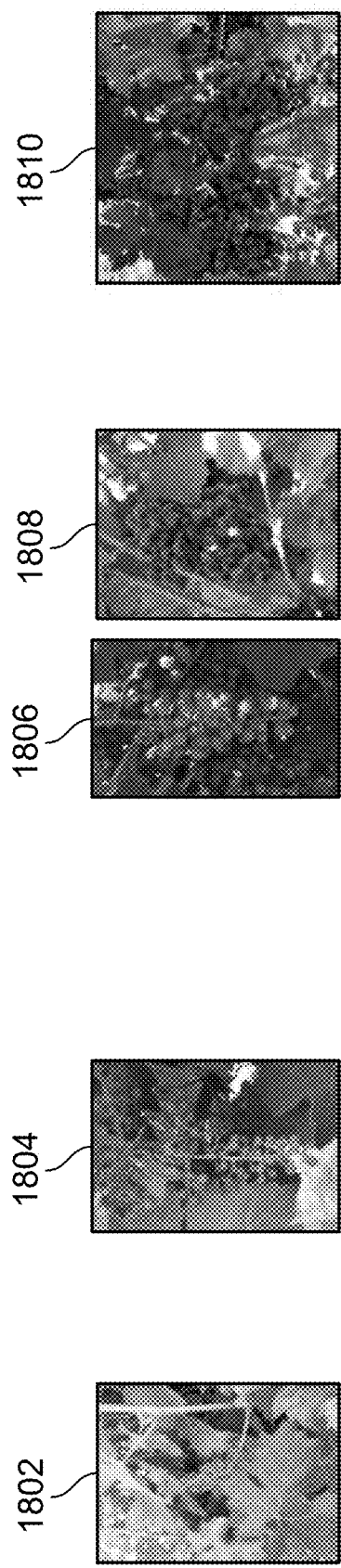
FIG. 18A illustrates photographs of fruit over a pre-bloom season to a harvest season along with corresponding X-ray backscatter images of the fruit, in accordance with an embodiment of the present specification.
Figure 18B:
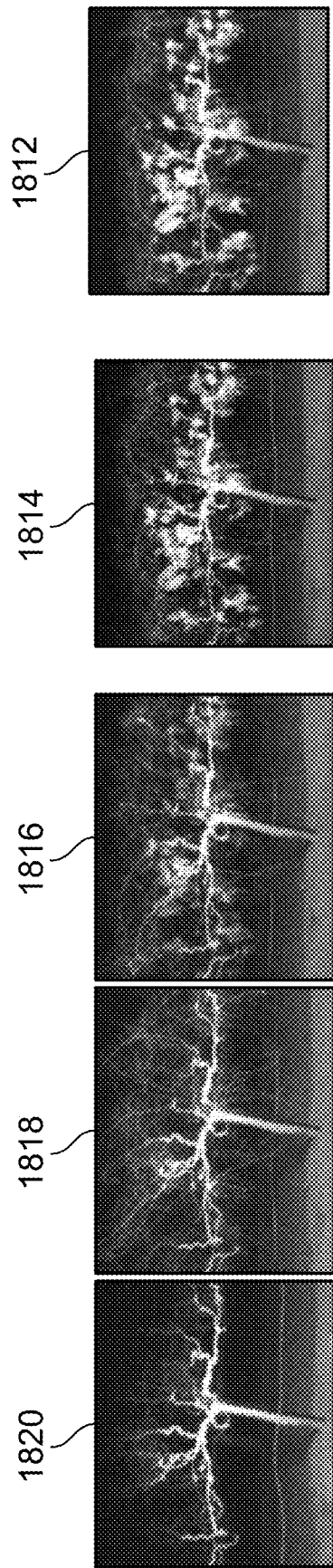
FIG. 18B illustrates backscatter X-ray scan images corresponding to the photographs of fruit shown in FIG. 18A, in accordance with an embodiment of the present specification.

FIG. 18A are photographs of fruit over a pre-bloom season (i.e. late April) to a harvest season (i.e. late October) along with corresponding X-ray backscatter images of the fruit, in accordance with an embodiment of the present specification. Photograph 1802 shows a pre-bloom view of fruit clusters taken in late April; photograph 1804 shows the fruit clusters in late May while photograph 1806 shows the fruit clusters four weeks later; photograph 1808 shows the fruit clusters in late July; and photograph 1810 shows the fruit clusters near harvest time in late October. Corresponding backscatter X-ray scan images are shown in FIG. 18B, wherein image 1812 corresponds to fruit clusters shown in photograph 1810; image 1814 corresponds to fruit clusters shown in photograph 1808; image 1816 corresponds to fruit clusters shown in photograph 1806; image 1818 corresponds to fruit clusters shown in photograph 1804; and image 1820 corresponds to fruit clusters shown in photograph 1802. In an embodiment, an exemplary correlation between the images and corresponding fruit clusters ranges from 80% between scan image 1812 and the fruit clusters shown in photograph 1810 to 64% between scan image 1818 and the fruit clusters shown in photograph 1804.

Figures 18C, 18D, 18E:
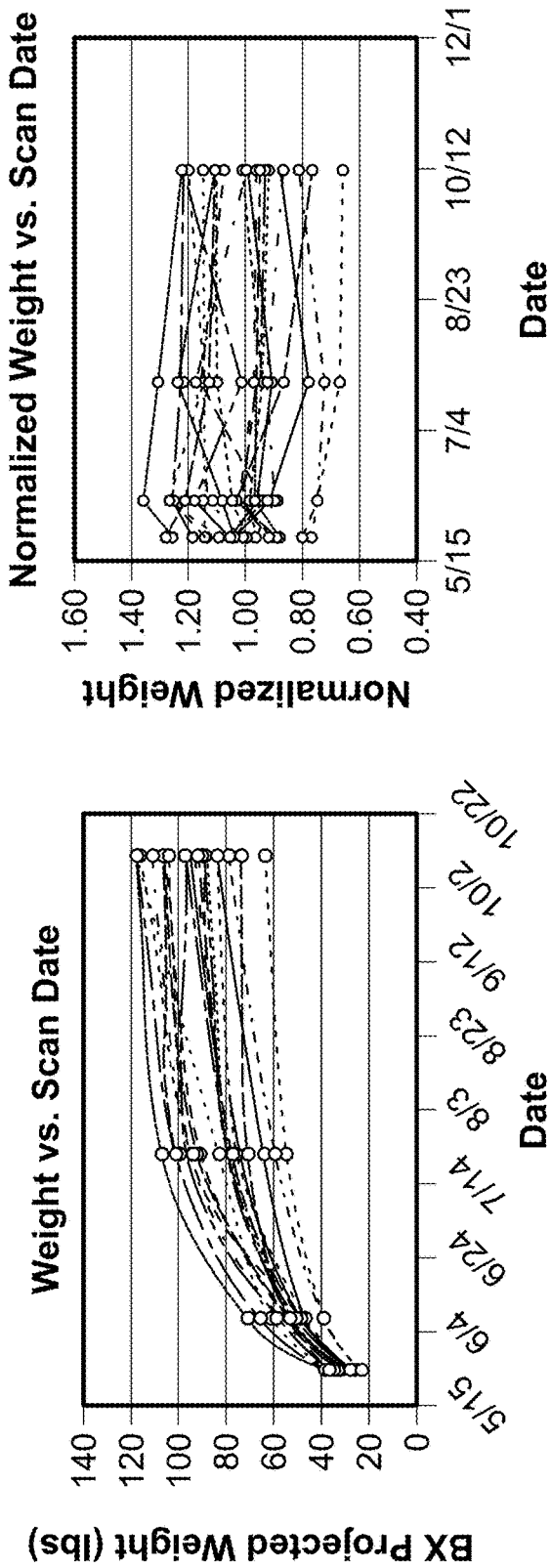
FIG. 18C is a table for tracking weight of individual fruit vines along with corresponding scan image correlation, over a predefined period of time, in accordance with an embodiment of the present specification.
FIG. 18D illustrates plots of vine weight versus scan data corresponding to a plurality of fruit vines over a time period, in accordance with an embodiment of the present specification.
FIG. 18E illustrates normalized plots of vine weight versus scan data corresponding to the plots shown in FIG. 18D, in accordance with an embodiment of the present specification.

FIG. 18C is a table tracking a weight of individual fruit vines along with corresponding scan image correlation, over a predefined period of time, in accordance with an embodiment of the present specification. Table 1830 comprises a column 1832 for recording dates on which weight and scan images of a fruit vine/cluster is obtained; a column 1834 for recording a stage of harvest of the fruit vine/cluster; column 1836 for recording corresponding average weights of the fruit vine/cluster; and a column 1838 for recording corresponding scan image correlations with the fruit vine/cluster. As can be observed from the table 1830, the fruit vine/cluster increases in weight from May to July after which there is little change in the weight until harvest in November. Further, the correlation between corresponding scan images and the fruit vine/cluster is maintained between May and final harvest in November. FIG. 18D illustrates plots of vine weight versus scan data corresponding to a plurality of fruit vines over a period ranging from May to October, in accordance with an embodiment of the present specification. FIG. 18E illustrates normalized plots of vine weight versus scan data corresponding to the plots shown in FIG. 18D, in accordance with an embodiment of the present specification.

Persons of ordinary skill in the art should appreciate that, in some embodiments, data corresponding to the X-ray scan images of the crop such as, but not limited to precipitation, time of year, temperature, geographical coordinates, wind speed, and sun exposure, is stored in a database coupled with the controller and is used to determine weight of hanging fruit and/or an on-going prediction of the crop yield at different times/months of the year, by employing processing techniques such as (for example) artificial intelligence and big data analytics. In an embodiment, backscattered signal increases with an increase in cluster size of fruit being scanned. FIG. 19A is a graph illustrating a relationship between scatter intensity and cluster size, in accordance with an embodiment of the present specification. As seen in image 1910, plot 1912 depicts an increase in scatter intensity plotted on y-axis 1914 with an increase in thickness of a cluster of fruit being scanned which is plotted on x-axis 1916.

In an embodiment, a backscattered signal decreases with an increase in distance between the X-ray scanner and the cluster of fruit being scanned. FIG. 19B is a graph illustrating a relationship between scatter signal and distance between scanner and fruit, in accordance with an embodiment of the present specification. As seen in image 1920, plot 1922 depicts a decrease in scatter signal intensity plotted on y-axis 1924 with an increase in distance between the X-ray scanner and the cluster of fruit being scanned which is plotted on x-axis 1926. It can be seen in image 1920 that the scatter signal intensity falls to approximately 10% of a maximum intensity while scanning a fruit cluster at a farthest distance, which is approximately 3 feet from the scanner. It is observed that, distance from the scanner as well as cluster size of fruit being scanned adds noise to the backscattered signal. In various embodiments, assuming a random distribution of fruit cluster sizes in an area being scanned, averaging the cluster size enables elimination of noise in the backscattered signal due to increase in distance between the scanner and the clusters. In various embodiments, harvest yield data corresponding to a crop cluster is based on a total intensity of the backscatter signal from the cluster. In embodiments, harvest yield data plotted against said backscatter intensity varies with crop since the composition of fruit clusters varies with crop, as the backscatter signal intensity is different when the X-rays are backscattered by water as compared to other material in fruit.

In embodiments, since backscattered signal intensity decreases with an increase in distance between scanner and fruit, and signal intensity does not have a strong correlation with weight of the fruit, an alternate image feature having an improved correlation with fruit weight is used over a predefined number of ground truth vines. In embodiments, a row of vines comprises approximately 120 vines. Ground truth vines are the vines which are monitored over a predefined period of time, and these vines are imaged before and after harvesting and weighing. In an embodiment a region analysis method is used for providing feature size, number shape and orientation. FIG. 20A illustrates a region analysis method, in accordance with an embodiment of the present specification. In an embodiment as shown in FIG. 20A, image 2010 is acquired prior to ground truth harvest; image 2012 is acquired after ground truth harvest; image 2014 is obtained after performing an image normalization of image 2012 and image 2010 and then subtracting normalized image 2012 from normalized image 2010; image 2016 depicts threshold features and image 2018 depicts results of region of interest analysis on features such as, but not limited to, area, perimeter, orientation, intensity, and number.

Figure 20B:
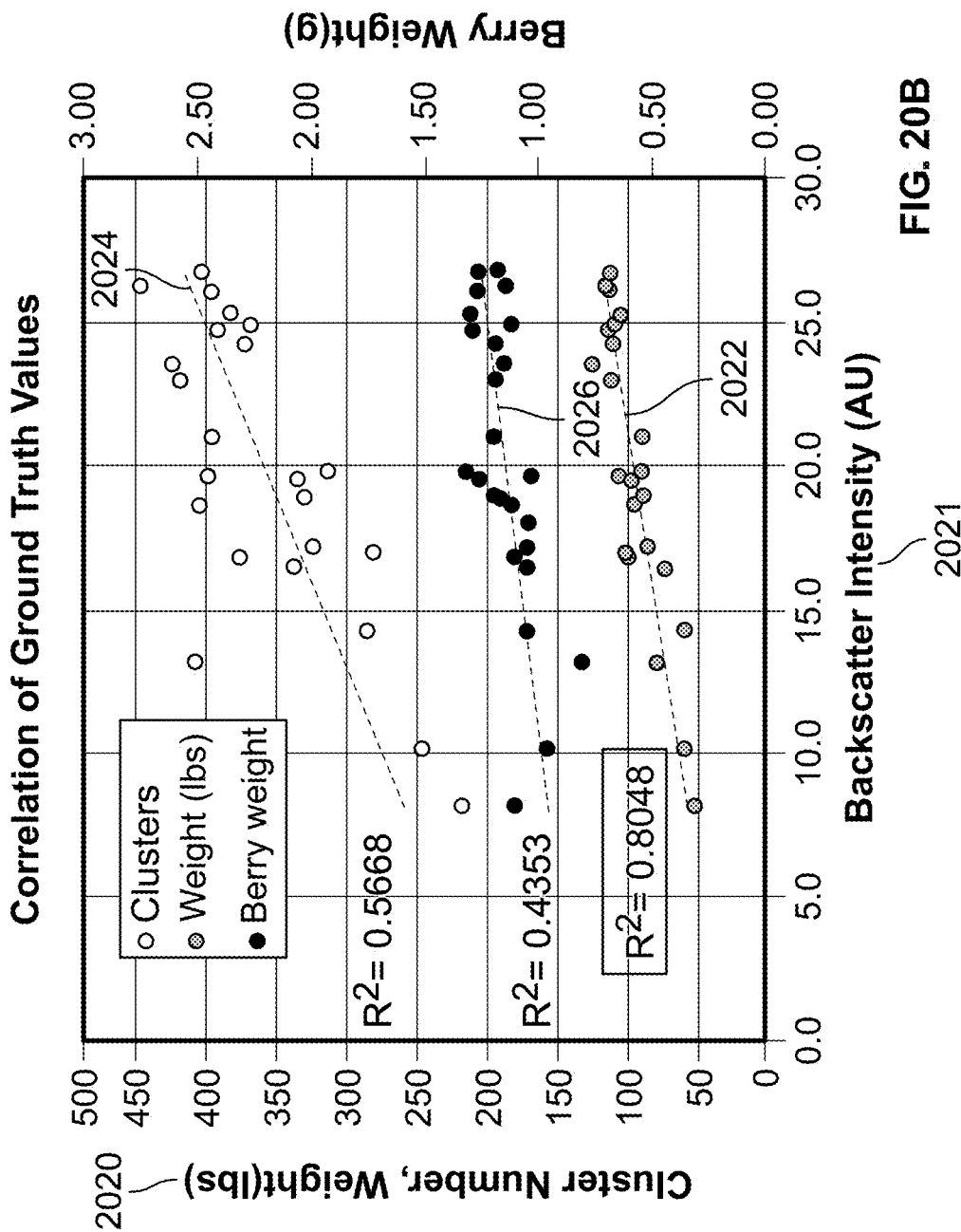
FIG. 20B is a graph illustrating a correlation between ground truth cluster weights plotted on y-axis 2020 and X-ray backscatter intensities plotted on x-axis 2021 at different values of applied correction factor, in accordance with an embodiment of the present specification.

FIG. 20B illustrates a graph showing correlation between ground truth cluster weights plotted on y-axis 2020 and X-ray backscatter intensities plotted on x-axis 2021 at different values of correction factor applied, in accordance with an embodiment of the present specification. As can be seen, plot 2022 exhibits the best correlation at a correction factor 'R'=0.8048. Plot 2204 exhibits the worst correlation at a correction factor 'R'=0.5668 while plot 2206 exhibits a mid-level correlation at a correction factor 'R'=0.4353. In various embodiments, processing variations involving steps such as, but not limited to, pre-bloom image subtraction, intensity correction corresponding to a given magnification factor, fulling the cordon area using simple interpolation from below and above, multiplying pixel rows with a factor based on distance from cordon, and raising intensity of each pixel to a power, produce less than desired correlation results.

FIG. 21A illustrates a scanning system for scanning crops to predict the weight of hanging fruit, in accordance with an embodiment of the present specification. In some embodiments, it is observed that approximately 20% variation in signal intensity occurs when using a scanning system 2102 such as shown in FIG. 21A. Since, performance of an X-ray scanning system changes with changes in the operating temperature, in an embodiment, a contrast block is inserted in a region 2104 of scanning system 2102 as the contrast block enables correction of the X-ray beam output intensity and detector sensitivity with temperature of the X-ray scanning system. FIG. 21B illustrates a contrast block employed in the scanning system of FIG. 21A, in accordance with an embodiment of the present specification. In an embodiment, contrast block 2106 is a plastic (HDPE) block which is inserted in a field of view of the scanning system 2102. FIG. 22C illustrates a scan image obtained by using a contrast block, in accordance with an embodiment of the present specification. FIG. 21D illustrates a graph showing variation in the intensity of contrast block region across field with respect to different times of the day, in accordance with an embodiment of the present specification.

Figure 22:
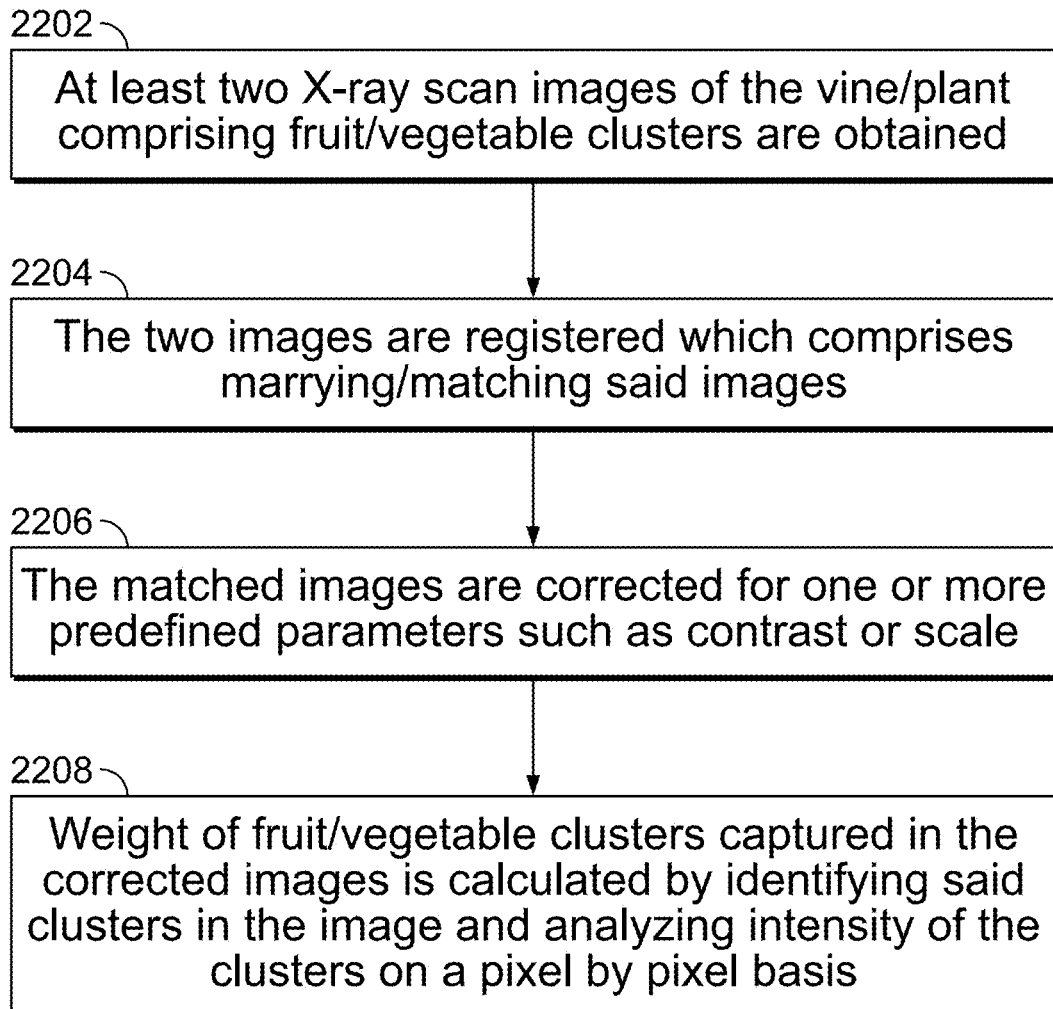
FIG. 22 is a flowchart illustrating a method for determining the hanging weight of fruits/vegetables on plants/vines/branches, in accordance with an embodiment of the present specification.

In various embodiments, the present specification provides a method to accurately assess the mass of fruits/vegetables growing on plants/branches/vines, which is often referred to as a hanging weight. FIG. 22 is a flowchart illustrating a method for determining the hanging weight of fruits/vegetables on plants/branches/vines, in accordance with an embodiment of the present specification.

At step 2202 at least two X-ray scan images of the plant/branch/vine comprising fruit/vegetable clusters are obtained. In embodiments, said images are obtained from at least two opposing sides/directions, as is shown in FIG. 17E. In an embodiment, the present specification provides a method for performing dual-view data acquisition by scanning the clusters using two X-ray scanners simultaneously. In another embodiment, dual view data acquisition may be performed by scanning the clusters using a single X-ray scanner with multiple acquisitions In embodiments, the two obtained scan images are offset from each other by an angle ranging from 90 to 270 degrees, which may be achieved by taking a first image from a first side or plane and a second image from a second side or plane. In an embodiment, a preferred offset between said images is 180 degrees, such that the sides from which the images are taken are essentially parallel to each other.

At step 2204 the two images are registered which comprises marrying/matching said images. In an embodiment, the two images are registered by flipping and translating one image relative to the other, as is described with reference to FIG. 12A above. The method of registration of the images described in the present specification is performed under the assumption that the two obtained images are parallel to each other. In embodiments, where the obtained scan images corresponding to two sides of the clusters are not parallel to each other, various different registration methods may be employed to match the images correctly.

At step 2206, the matched images are corrected for one or more predefined parameters such as contrast or scale. Conventional backscatter X-ray scanning applications are employed for detection of hidden threat elements such as, but not limited to guns and other weapons. In such cases scan images are required to be clear enough to approximate a shape of said weapons. However, in the present specification, the scan images are required to be clearer than conventional applications as precise calculation of the hanging weight of the clusters is dependent upon the clarity of said images. Hence, the registered images are corrected at least for contrast, brightness, intensity, and scale. In embodiments, feature level correction and distance correction is performed on said matched images, as is described with reference to FIGS. 12A and 12B.

At step 2208, weight of fruit/vegetable clusters captured in the corrected images is calculated by identifying said clusters in the image and analyzing intensity of the clusters on a pixel by pixel basis. The analyzed intensity is summed over a predefined period of time and correlated to obtain the weight. In an embodiment, an estimation of the weight of the fruit/vegetable clusters is achieved by determining a change in X-ray signal backscattered by the cluster over a predetermined period of time, such as over a pre-bloom season from late April to a harvest season in late October of any given year, as is described with reference to FIGS. 12A, 18A-18D. Performing volumetric estimation of the imaged clusters often leads to inaccurate results as the fruit/vegetable may overlap with each other, making it difficult to determine volume. Hence, in accordance with the method of the present specification mass/weight of the imaged fruit/vegetable clusters is determined by using pixel intensity of the images.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A method for estimating weight of plants, wherein the plants are organized in at least one row and wherein the plants comprise at least one fruit bearing portion, the method comprising:
   irradiating the plants with X-rays from a first side and a second side, wherein the first side opposes the second side;
   obtaining a first scan image of the plants from the first side and a second scan image of the plants from the second side;
   correlating a portion of the first scan image with a portion of the second scan image to obtain an area of overlap between the first scan image and the second scan image;
   based on said correlation, isolating the at least one fruit bearing portion from first scan image and second scan image to generate a second set of images;
   aligning a first of the second set of images with a second of the second set of images based on whether the first of the second set of images and the second of the second set of images show different views of a same one of the at least one fruit bearing portion; and
   estimating a weight of a portion of the plants by using the aligned images.

2. The method of claim 1, further comprising, prior to said correlation, enhancing contrast of the first scan image and the second scan image.

3. The method of claim 1, further comprising, prior to said correlation, de-noising the first scan image and the second scan image.

4. The method of claim 1, further comprising, prior to said weight estimation, processing the aligned images, wherein the processing comprises applying a correction based on a ratio of a first intensity measured from the first scan image and a second intensity measured from the second scan image.

5. The method of claim 1, further comprising flipping a visual shown in at least one of the first scan image or the second scan image.

6. The method of claim 1, wherein isolating the at least one fruit bearing portion comprises separating a vine and/or a branch from said first scan image and said second scan image by discarding edges of the vine and/or edges of the branch.

7. The method of claim 1, further comprising determining GPS coordinates of points on a map by correlating at least one timestamp of one or more GPS coordinates with at least one timestamp of when the points on the map were captured.

8. The method of claim 7, wherein the GPS coordinates are correlated with image data.

9. The method of claim 7, further comprising locating rows of plants along with a corresponding direction based on a direction of movement of the vehicle and transforming the located rows of plants in a predefined direction to obtain a consistent sequence of plants in each of the first scan image and the second scan image.

10. The method of claim 1, further comprising normalizing the first scan image and the second scan image.

11. The method of claim 7, further comprising scanning GPS coordinates to determine one or more distances between rows of plants.

12. The method of claim 1, further comprising determining a cluster processing method to process the second set of images.

13. The method of claim 12, further comprising processing the second set of images by using a coarse cluster segmentation method.

14. The method of claim 1, wherein said weight of the portion of the plants is equivalent to the weight of fruit hanging from the plants and is a function of a change in an X-ray backscatter signal over a predefined period of time.

15. The method of claim 14, wherein the fruit comprises at least one of grapes, berries, citrus fruits, apples, melons, or tomatoes.

16. The method of claim 14, wherein the X-ray backscatter signal is proportional to a mass of the fruit and a distance of the fruit a source of the X-rays.

17. The method of claim 14, wherein the X-ray backscatter signal from the fruit is proportional to a square of the distance of the fruit from the source of the X-rays.

18. The method of claim 14, wherein a mass of the fruit is determined by integrating a signal intensity of the X-ray backscatter signal from the fruit.

19. The method of claim 14, further comprising performing dual view data acquisition by simultaneously scanning the fruit using two sources of X-rays.

20. The method of claim 14, further comprising performing dual view data acquisition by scanning the fruit using one source of X-rays multiple times.

21. The method of claim 1, further comprising analyzing said first scan image and/or second scan image by using a distance normalization process at a pixel level or feature level.

22. The method of claim 1, further comprising processing the second set of images to identify at least one cluster.

23. The method of claim 22, further comprising annotating the identified at least one cluster.

24. The method of claim 23, further comprising using a deep learning algorithm to identify the at least one cluster and annotate the identified at least one cluster.

25. The method of claim 1, wherein the first scan image is obtained along a first plane relative to the plants and the second scan image is obtained along a second plane relative to the plants and wherein the first plane is angularly displaced relative to the second plane.

26. The method of claim 25, wherein the first plane is angularly displaced relative to the second plane by an angle ranging between 90 degrees and 270 degrees.

27. The method of claim 25, wherein the first plane and the second plane are parallel to each other.

28. The method of claim 1, further comprising obtaining the first scan image and the second scan image using two X-ray scanners simultaneously.

29. The method of claim 1, further comprising obtaining the first scan image and the second scan image by scanning the plants using one X-ray scanner.

30. The method of claim 4, wherein applying the correction comprises correcting each of said first scan image and second scan image for at least one of contrast, brightness, intensity, or scale.

31. The method of claim 1, wherein estimating the weight of the portion of the plants comprises identifying one or more clusters of fruit in the aligned images and analyzing an intensity of the one or more clusters on a pixel by pixel basis.

32. The method of claim 31, further comprising summing and correlating the analyzed intensity of the one or more clusters over a predefined period of time.

\* \* \* \* \*